(12) United States Patent
Maness

(10) Patent No.: US 8,534,459 B2
(45) Date of Patent: Sep. 17, 2013

(54) CANCELLATION FEATURE FOR PHARMACEUTICAL WASTE DISPOSAL ASSEMBLY

(75) Inventor: David A. Maness, Mt. Pleasant, SC (US)

(73) Assignee: Cactus, LLC, Charleston, SC (US)

( * ) Notice: Subject to any disclaimer, the term of this patent is extended or adjusted under 35 U.S.C. 154(b) by 233 days.

(21) Appl. No.: 12/981,281

(22) Filed: Dec. 29, 2010

(65) Prior Publication Data
US 2012/0168443 A1 Jul. 5, 2012

(51) Int. Cl.
*B65D 85/24* (2006.01)

(52) U.S. Cl.
USPC ............................................. 206/366; 206/370

(58) Field of Classification Search
USPC .................. 206/363–366, 1.5, 807; 604/110, 604/192; 70/1, 57, 57.1, 61–63, 77
See application file for complete search history.

(56) References Cited

U.S. PATENT DOCUMENTS

| | | | |
|---|---|---|---|
| 3,643,266 A | 2/1972 | Black | |
| 4,576,281 A * | 3/1986 | Kirksey | 206/366 |
| 4,738,361 A * | 4/1988 | Ackeret | 206/308.1 |
| 4,801,034 A | 1/1989 | Sandomeno | |
| 4,816,307 A | 3/1989 | Honeycutt | |
| 4,981,476 A * | 1/1991 | Aichlmayr et al. | 604/192 |
| 5,022,548 A | 6/1991 | Stakis | |
| 5,038,929 A | 8/1991 | Kubofcik | |
| 5,111,958 A | 5/1992 | Witthoeft | |
| 5,167,193 A | 12/1992 | Withers et al. | |
| 5,245,117 A | 9/1993 | Withers et al. | |
| 5,273,161 A | 12/1993 | Sagstetter | |
| 5,279,413 A * | 1/1994 | Nehl et al. | 206/495 |
| 5,323,719 A | 6/1994 | Withers et al. | |
| 5,385,105 A | 1/1995 | Withers et al. | |
| 5,458,072 A | 10/1995 | Hughes et al. | |
| 5,483,999 A | 1/1996 | Lampropoulos et al. | |
| 5,495,941 A | 3/1996 | Leonard | |
| 5,595,711 A | 1/1997 | Wilson et al. | |
| 5,641,947 A | 6/1997 | Riddle, Jr. | |
| 5,707,173 A | 1/1998 | Cottone et al. | |
| 5,735,834 A | 4/1998 | Hemstreet et al. | |
| 5,792,126 A | 8/1998 | Tribastone et al. | |
| 5,931,031 A * | 8/1999 | Bouan | 70/57.1 |
| 5,947,285 A | 9/1999 | Gaba et al. | |
| 6,010,444 A | 1/2000 | Honeycutt et al. | |

(Continued)

FOREIGN PATENT DOCUMENTS

WO WO2009141583 11/2009

*Primary Examiner* — Luan K Bui

(74) *Attorney, Agent, or Firm* — Roeder & Broder LLP; James P. Broder

(57) ABSTRACT

A cancellation feature (2203) for a pharmaceutical waste disposal assembly (10) having a first surface (2201) and a second surface (2202) can include a first cancellation member (2204) that is secured to the first surface (2204) and a second cancellation member (2205) that is secured to the second surface (2205). The second cancellation member (2205) automatically moves from a pre-engaged configuration that allows engagement with the first cancellation member (2204) to a post-engaged configuration that inhibits engagement with the first cancellation member (2204). The automatic movement occurs after engagement and/or during disengagement between the second cancellation member (2205) and the first cancellation member (2204). The first surface (2201) can form a portion of a receiver that receives pharmaceutical waste, and the second surface (2202) can form a portion of a receiver retainer that retains the receiver. Conversely, the second surface (2202) can form a portion of the receiver and the first surface (2201) can form a portion of the receiver retainer.

20 Claims, 30 Drawing Sheets

(56) References Cited

U.S. PATENT DOCUMENTS

| | | | |
|---|---|---|---|
| 6,053,314 | A | 4/2000 | Pittman |
| 6,062,419 | A * | 5/2000 | Kruger et al. ............ 220/711 |
| 6,090,572 | A | 7/2000 | Crosby |
| 6,733,481 | B2 | 5/2004 | Ow |
| 6,797,857 | B2 | 9/2004 | Tanhehco |
| 7,119,689 | B2 | 10/2006 | Mallett et al. |
| 7,123,150 | B2 | 10/2006 | Mallett et al. |
| 7,126,480 | B2 | 10/2006 | Mallett et al. |
| 7,138,918 | B2 | 11/2006 | Mallett et al. |
| 7,258,711 | B2 | 8/2007 | Dunn et al. |
| 7,275,645 | B2 | 10/2007 | Mallett et al. |
| 7,296,688 | B2 | 11/2007 | Mallett et al. |
| 7,303,080 | B2 | 12/2007 | Mallett et al. |
| 7,303,081 | B2 | 12/2007 | Mallett et al. |
| 7,303,082 | B2 | 12/2007 | Mallett et al. |
| 7,311,207 | B2 | 12/2007 | Mallett et al. |
| 7,341,147 | B2 | 3/2008 | Mallett et al. |
| 7,383,195 | B2 | 6/2008 | Mallett et al. |
| 7,454,358 | B2 | 11/2008 | Mallett et al. |
| 7,483,837 | B2 | 1/2009 | Mallett et al. |
| 7,487,100 | B2 | 2/2009 | Mallett et al. |
| 7,490,722 | B2 | 2/2009 | Mayda et al. |
| 7,533,028 | B2 | 5/2009 | Mallett et al. |
| 7,533,029 | B2 | 5/2009 | Mallett et al. |
| 7,562,025 | B2 | 7/2009 | Mallett et al. |
| 7,565,299 | B2 | 7/2009 | Mallett et al. |
| 7,600,638 | B2 * | 10/2009 | Finnestad et al. ............ 206/366 |
| 7,617,113 | B2 | 11/2009 | Mallett et al. |
| 7,620,559 | B2 | 11/2009 | Mallett et al. |
| 7,660,724 | B2 | 2/2010 | Mallett et al. |
| 2002/0095125 | A1 | 7/2002 | Parker |
| 2003/0164600 | A1 | 9/2003 | Dunn et al. |
| 2004/0144682 | A1 | 7/2004 | Altmayer |
| 2004/0236292 | A1 | 11/2004 | Tazoe et al. |
| 2005/0103662 | A1 | 5/2005 | Iske et al. |
| 2005/0106087 | A1 | 5/2005 | Tanhehco |
| 2005/0267425 | A1 | 12/2005 | Castora et al. |
| 2006/0212306 | A1 | 9/2006 | Mallett et al. |
| 2007/0224077 | A1 | 9/2007 | Cox et al. |
| 2008/0058736 | A1 | 3/2008 | Reshamwala |
| 2010/0076244 | A1 | 3/2010 | Parrott |

* cited by examiner

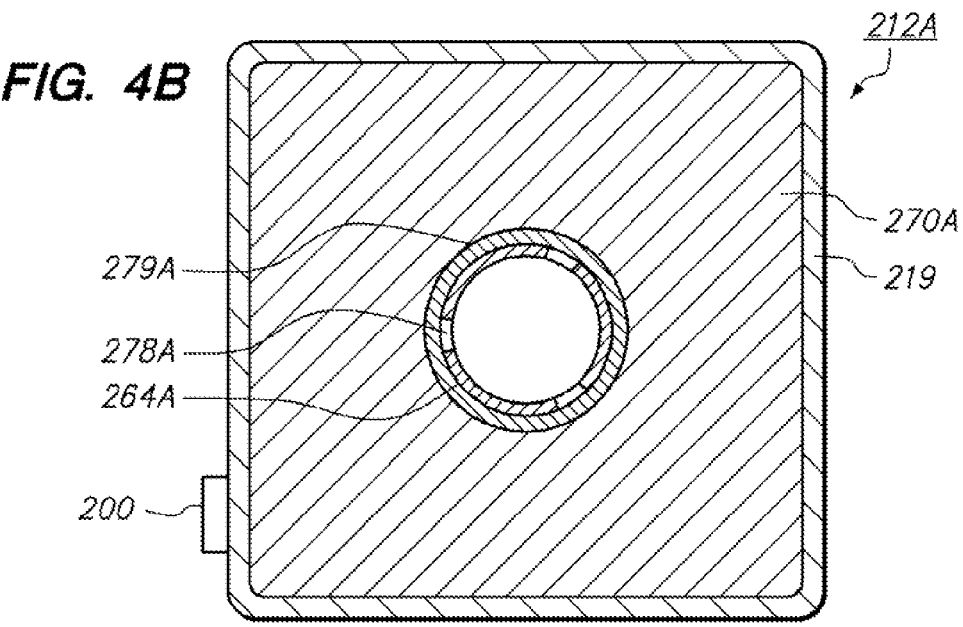
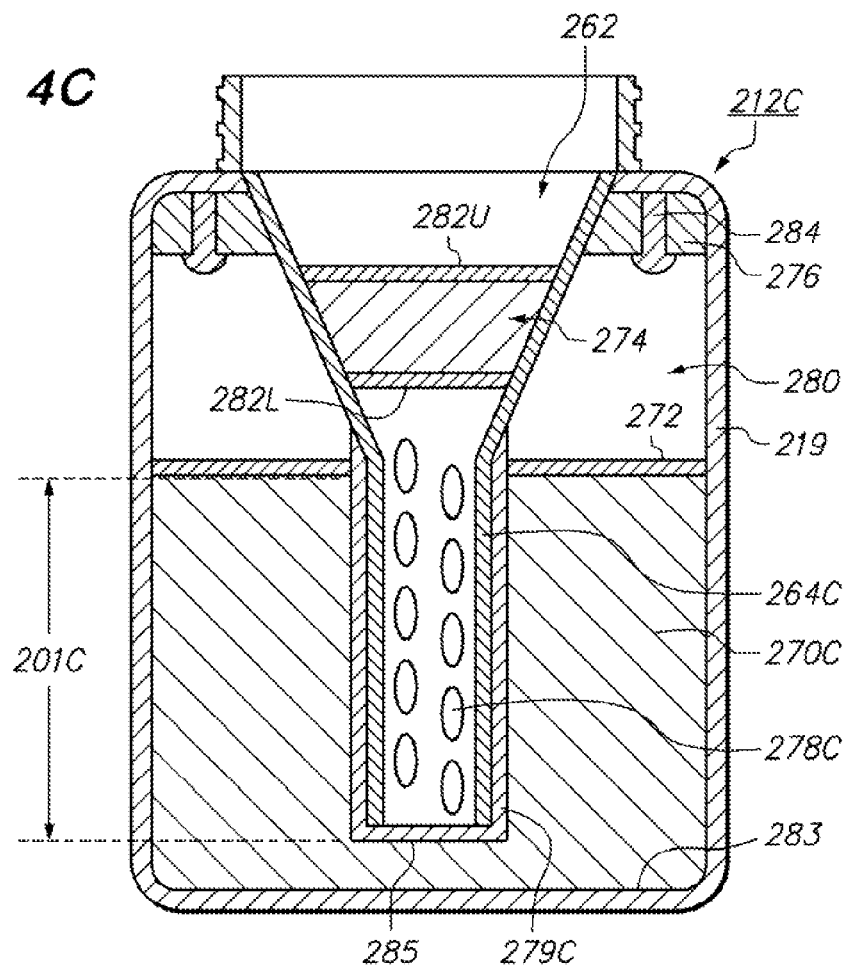

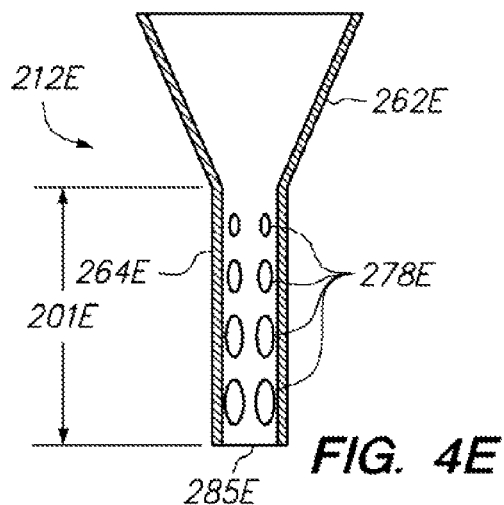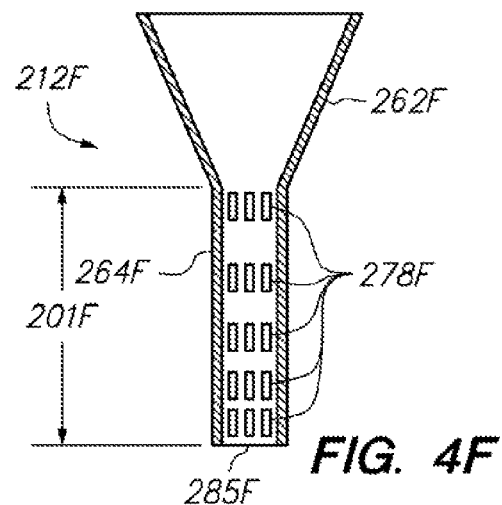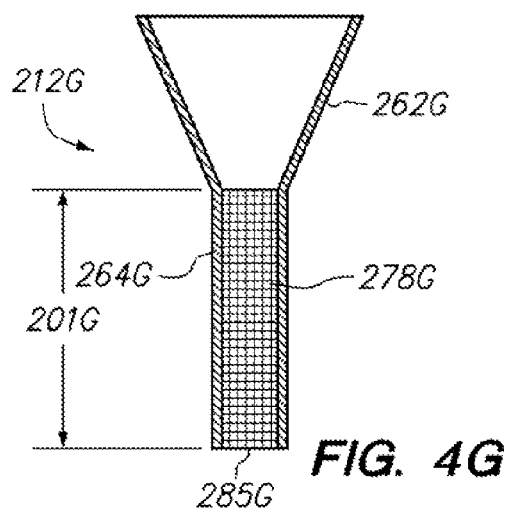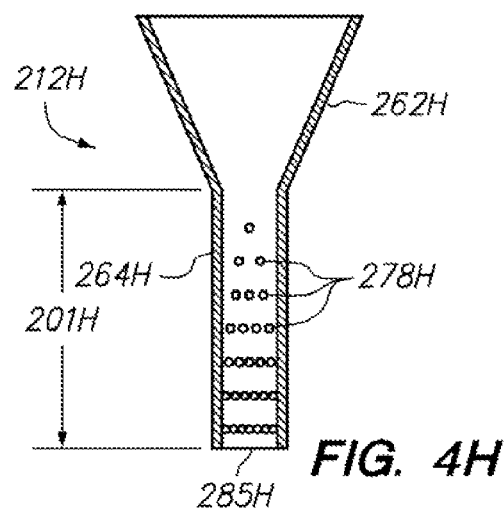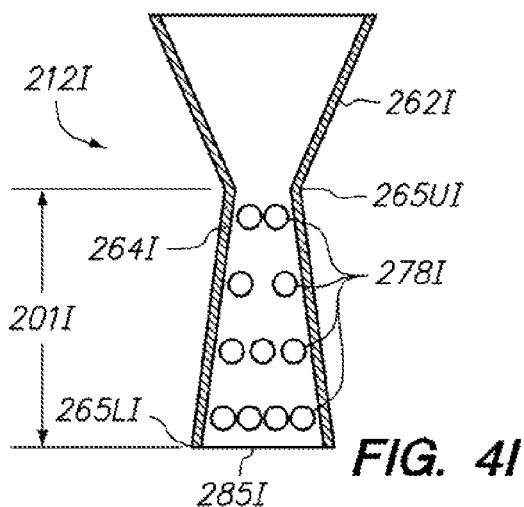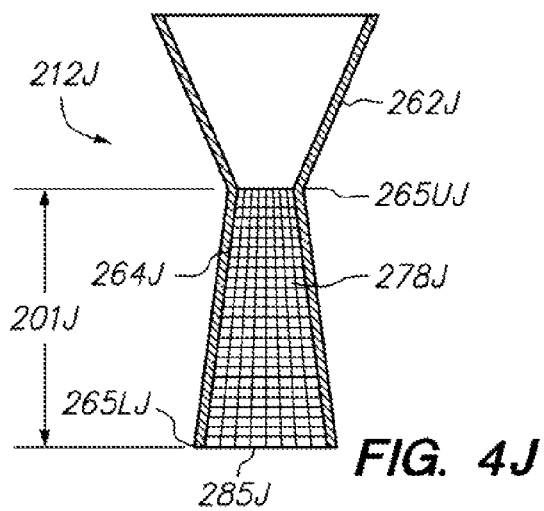

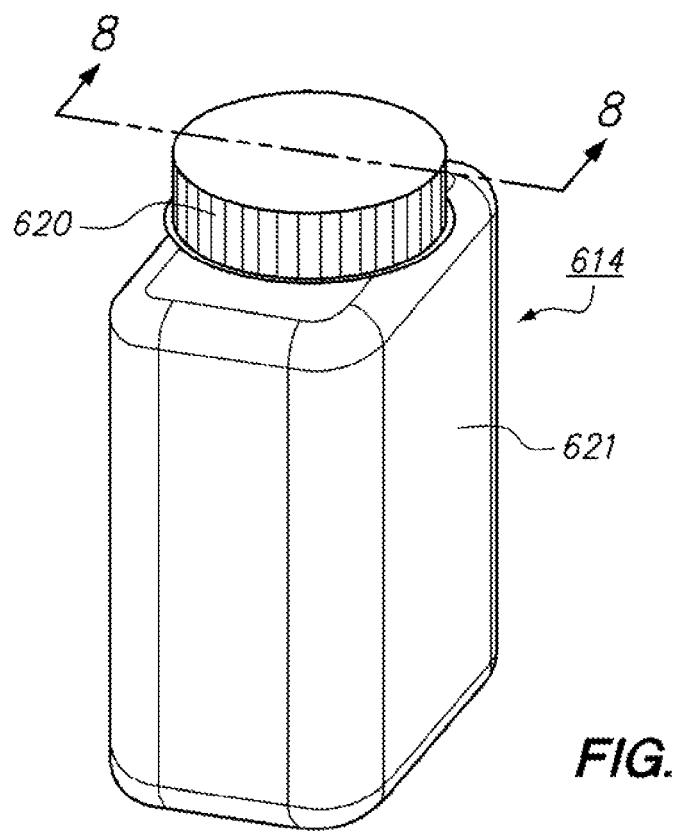
FIG. 6
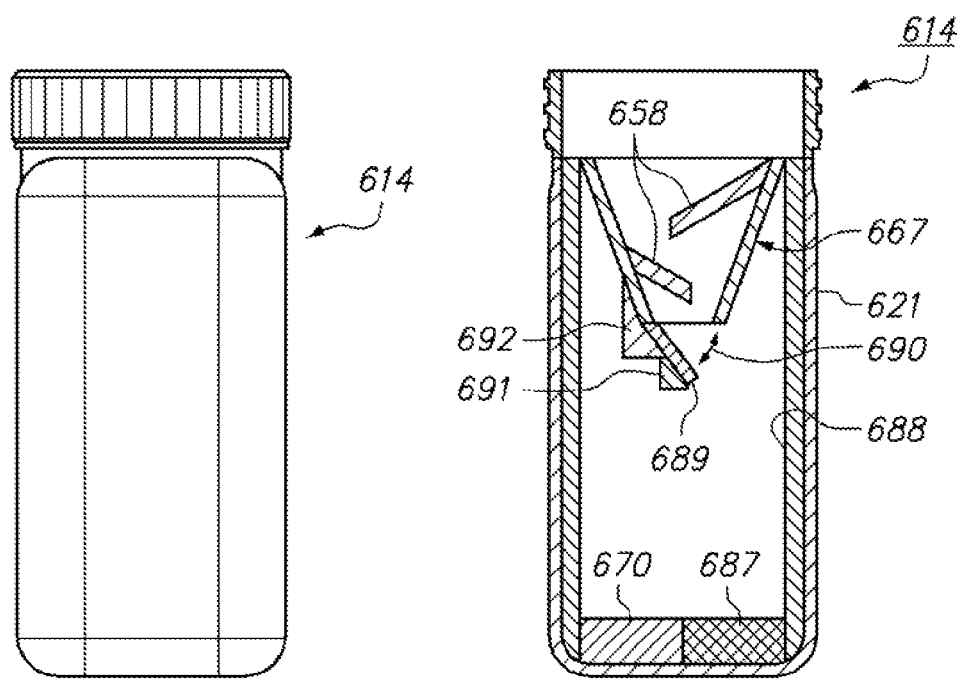
FIG. 7
FIG. 8

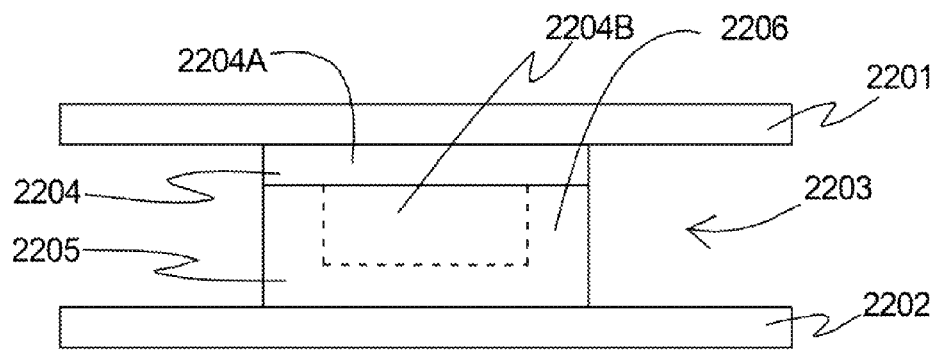
Fig. 22B
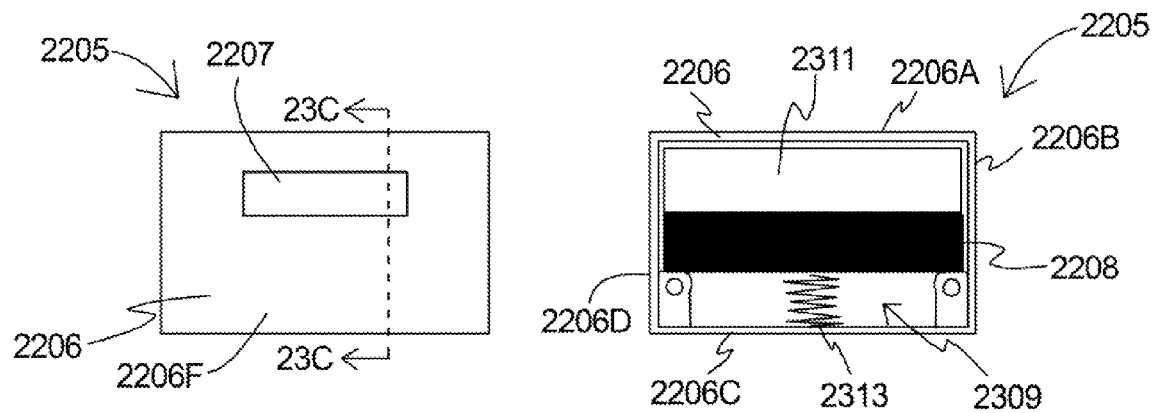
Fig. 23A
Fig. 23B
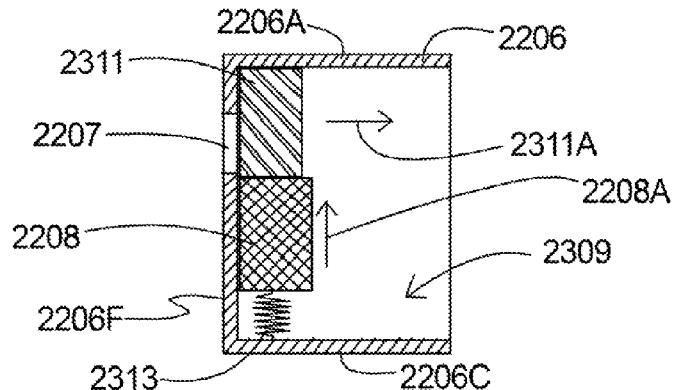
Fig. 23C

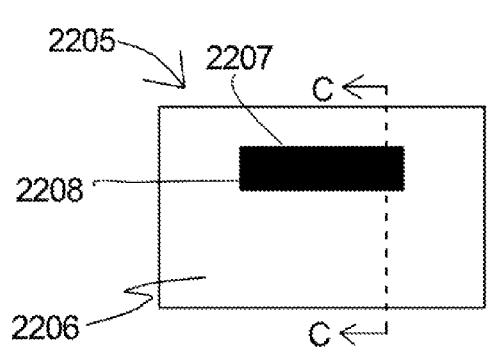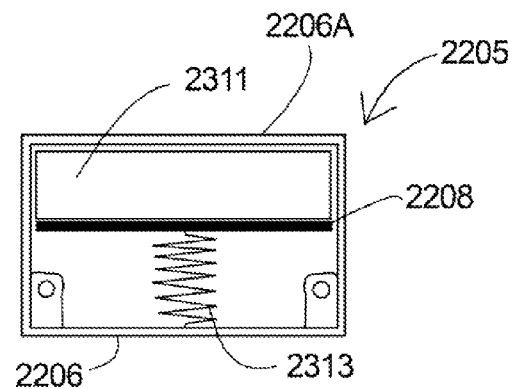
Fig. 24A    Fig. 24B
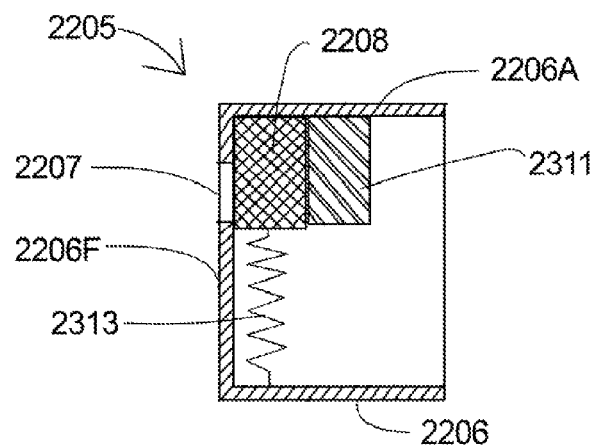
Fig. 24C

CANCELLATION FEATURE FOR PHARMACEUTICAL WASTE DISPOSAL ASSEMBLY

BACKGROUND

The disposal of pharmaceutical waste has long been a concern of those in the medical care industry. Pharmaceutical waste can include both liquids and solids, such as expired medicines, partially filled vials, compounded IV's, broken or spilled materials, undispensed compounded products, discontinued indated items, unused unit dosed items, unused IV's, patients' personal medications, and certain hazardous waste materials, to name a few. Further, pharmaceutical waste can be "raw", such that the waste does not include any sort of container or packaging, or the waste can be contained in a container such as a bottle, vial, bag, dispenser, syringe, or any other type of packaging. By way of example and not of limitation, raw waste can include various liquids such as the fluid from a syringe, bag or bottle, or solids such as pills, capsules, powders, patches, etc. Ensuring that such waste does not wind up in the hands of unauthorized personnel, migrate to our waterways or bodies of water, or that illegal diversion does not occur, has been of primary importance not only in the pharmaceutical/medical industry, but in the environmental field as well. Currently, the Resource Conservation Recovery Act (RCRA) provides strict mandates for waste disposal and/or management. In fact, failure to comply with these RCRA regulations can result in the imposition of sizable monetary fines.

Hazardous waste, which includes chemicals or formulations deemed to be so detrimental to the environment that they must be segregated for special waste management, cannot legally be sewered or landfilled. Importantly, a number of relatively common drug entities and pharmaceutical formulations meet the definition of hazardous waste. As non-exclusive examples, drugs such as epinephrine, nitroglycerin, warfarin, nicotine and various chemotherapy agents fall into this hazardous waste category. The Environmental Protection Agency (EPA) defines characteristics of hazardous waste, including ignitability, toxicity, corrosivity and reactivity. Under conventional disposal methods, the acceptable means by which pharmaceutical waste may be disposed and treated are dependent upon the specific type of waste.

Historically, pharmaceutical waste has been disposed of by a variety of means including disposal in waste regions, sharps containers, sewering or incineration, to name a few. However, hospital incinerators are becoming much less preferred, and shipment of the waste to outside waste disposal firms may be required. Unfortunately, a substantial amount of solid or liquid pharmaceutical waste in a hospital setting is wrongfully deposited into biohazardous sharps containers, which are designed for receiving used/contaminated syringes and/or hypodermic needles. Alternatively, pharmaceutical waste is simply thrown in the trash or dumped down a drain, rather than utilizing a dedicated pharmaceutical waste system.

Attempts to address these issues have not been altogether satisfactory. For example, some relatively expensive waste receiver systems require that the waste drug remain in its original bar-coded container, which may be impractical in certain situations, such as raw waste. Additionally, utilizing dozens or even hundreds of these types of waste disposal systems in a hospital can be cost-prohibitive. Further, the size of these types of waste disposal systems may make providing such a system at each point of use around a health care facility unfeasible. Moreover, such systems can be relatively heavy and difficult to move, and can take up a substantial amount of valuable floor space in a hospital, for example.

Still further, in an attempt to save money, some people may endeavor to reuse pharmaceutical waste containers. Unfortunately, such attempts may be undertaken without the proper and necessary thorough cleaning of the pharmaceutical waste containers to remove all prior remnants of pharmaceutical waste. This can lead to the improper and potentially dangerous mixing of pharmaceutical wastes.

SUMMARY

The present invention is directed toward a cancellation feature for a pharmaceutical waste disposal assembly, the pharmaceutical waste disposal assembly having a first surface and a second surface. In certain embodiments, the cancellation feature comprises a first cancellation member and a second cancellation member. The first cancellation member is secured to the first surface. The second cancellation member is secured to the second surface. Additionally, the second cancellation member automatically moves from (i) a pre-engaged configuration that allows engagement with the first cancellation member to (ii) a post-engaged configuration that inhibits engagement with the first cancellation member. The automatic movement occurs after engagement between the second cancellation member and the first cancellation member.

In some embodiments, the first cancellation member includes a first member node that cantilevers away from the first surface. In some such embodiments, the second cancellation member includes a second member body having a second member aperture that receives the first member node.

Additionally, in certain embodiments, the second member body can form a body recess. In such embodiments, when the second cancellation member is in the pre-engaged configuration, the first member node can extend fully through the second member aperture and into the body recess. Further, in such embodiments, when the second cancellation member is in the post-engaged configuration, the first member node is inhibited from extending fully through the second member aperture and into the body recess.

In one embodiment, the second cancellation member further includes a blocker and a valve. In such embodiment, when the second cancellation member is in the pre-engaged configuration the blocker is positioned adjacent to the second member aperture. Further, in such embodiment, when the second cancellation member is in the post-engaged configuration the valve is positioned adjacent to the second member aperture.

Moreover, in one embodiment, when the second cancellation member is in the pre-engaged configuration, the first member node can extend fully through the second member aperture and into the body recess. In such embodiment, when the first member node extends fully through the second member aperture and into the body recess, the first member node contacts the blocker and moves the blocker away from the second member aperture. Additionally, the second cancellation member can further include a resilient member. In one embodiment, the resilient member moves the valve to be positioned adjacent to the second member aperture subsequent to the first member node moving the blocker away from the second member aperture.

In one embodiment, the first surface forms a portion of a receiver or a receiver assembly that receives pharmaceutical waste. In such embodiment, the second surface can form a portion of a receiver retainer that retains the receiver or receiver assembly.

Conversely, in one embodiment, the second surface forms a portion of a receiver or a receiver assembly that receives pharmaceutical waste. In such embodiment, the first surface can form a portion of a receiver retainer that retains the receiver or receiver assembly.

Additionally, the present invention is directed toward a pharmaceutical waste disposal assembly comprising a receiver or receiver assembly that receives pharmaceutical waste, a receiver retainer that retains the receiver or receiver assembly, and the cancellation feature as describe above.

Further, the present invention is directed toward a method for inhibiting reuse of a portion of a pharmaceutical waste disposal assembly.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4B is a cross-sectional view of the fluid waste receiver taken on line 4B-4B in FIG. 2;

FIG. 4C is a cross-sectional view of a portion of another embodiment of the fluid waste receiver;

FIGS. 4E-4J are various cross-sectional views of non-exclusive alternative embodiments of a portion of the fluid waste receiver;

FIG. 6 is a perspective view of one embodiment of the solid waste receiver having features of the present invention;

FIG. 7 is a front elevation of the solid waste receiver illustrated in FIG. 6;

FIG. 8 is a cross-sectional view of a portion of the solid waste receiver taken on line 8-8 in FIG. 6;

FIG. 22B is a side view of the first surface, the second surface and the cancellation feature illustrated in FIG. 22A, with a portion of the cancellation feature illustrated in phantom;

FIG. 23A is a front elevation view of the second cancellation member illustrated in FIG. 22A, with the second cancellation member shown in a pre-engaged configuration;

FIG. 23B is a rear elevation view of the second cancellation member illustrated in FIG. 22A, with the second cancellation member shown in the pre-engaged configuration;

FIG. 23C is a cross-sectional view of the second cancellation member taken on line 23C-23C in FIG. 23A;

FIG. 24A is a front elevation view of the second cancellation member illustrated in FIG. 22A, with the second cancellation member shown in a post-engaged configuration;

FIG. 24B is a rear elevation view of the second cancellation member illustrated in FIG. 22A, with the second cancellation member shown in the post-engaged configuration; and FIG. 24C is a cross-sectional view of the second cancellation member taken from line C-C in FIG. 24A.

DESCRIPTION

Figure 1A:
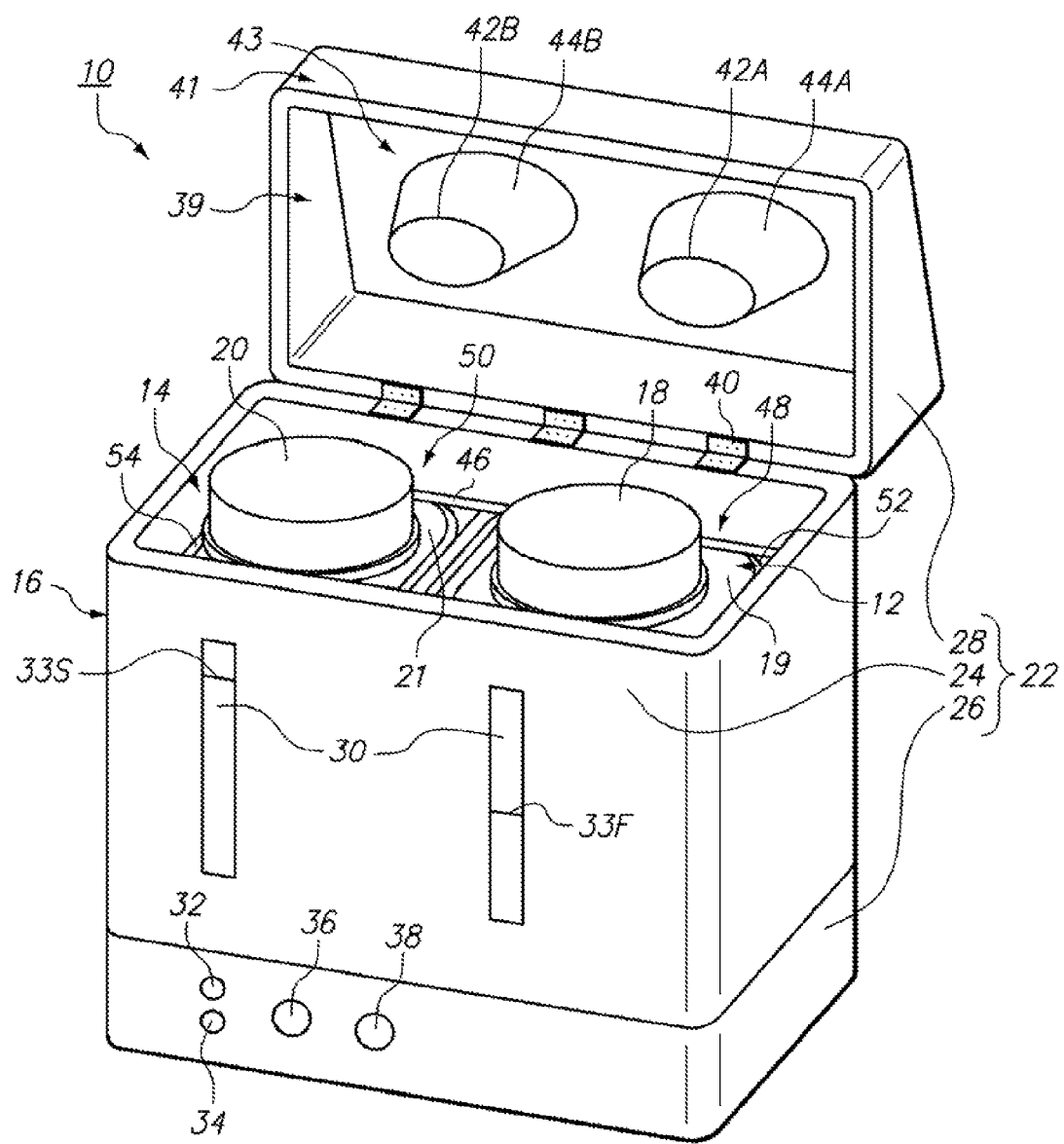
FIG. 1A is a perspective view of one embodiment of a pharmaceutical waste disposal assembly having features of the present invention, illustrated in an open position, including a fluid waste receiver, a solid waste receiver and a receiver retainer.

FIG. 1A is a perspective view of one embodiment of a pharmaceutical waste disposal assembly 10 (also sometimes referred to herein as a "disposal assembly"), shown in an open position. In one embodiment, the disposal assembly 10 provides a means for disposing of fluid and/or solid pharmaceutical and/or medical waste (generically referred to herein as "waste") which can ultimately be incinerated or otherwise treated and/or permanently disposed of. The design of the disposal assembly 10 can vary depending upon the specific application and/or location of the disposal assembly 10. In the embodiment illustrated in FIG. 1A, the disposal assembly 10 includes a fluid waste receiver 12, a solid waste receiver 14 and a receiver retainer 16.

In this embodiment, the fluid waste receiver 12 can receive waste in a liquid and/or a gaseous phase of matter. The design of the fluid waste receiver 12, including the size, volume, shape and specific materials that form the fluid waste receiver 12, can vary depending upon the design requirements of the disposal assembly 10. In the embodiment illustrated in FIG. 1A, the fluid waste receiver 12 includes a fluid receiver cap 18 and a fluid receiver body 19 (also sometimes referred to herein as "receiver body"). The fluid receiver cap 18 covers a fluid receiver opening (not illustrated in FIG. 1A) which provides access into an interior of the fluid waste receiver 12. In one embodiment, the fluid receiver cap 18 can be a tamper-resistant, locking cap that is positioned on the fluid waste receiver 12 once the fluid waste receiver 12 has reached a predetermined capacity or weight of fluid waste, has been in use for a predetermined duration of time, or is otherwise determined to be no longer suitable for receiving fluid waste. For example, the fluid receiver cap 18 can include a one-way ratchet ring that interlocks with the fluid receiver body 19.

The fluid receiver body 19 is configured to receive fluid waste that is deposited into the fluid waste receiver 12. The fluid receiver body 19 can be formed from any suitably durable materials. In one embodiment, the fluid receiver body 19 can be formed from a durable injection-molded plastic material. Alternatively, the fluid receiver body 19 can be formed from fiberglass, glass, ceramic, various metals, a composite material, or a combination thereof, as non-exclusive examples. In one embodiment, the material that forms the fluid receiver body 19 can be clear or otherwise see-through to allow a user to observe the level of waste within the fluid waste receiver 12. Alternatively, the material that forms the fluid receiver body 19 can be opaque or otherwise non-see-through.

In one embodiment, the fluid waste receiver 12 can have a capacity of approximately 2.0 liters. Alternatively, the fluid waste receiver 12 can have a capacity of greater than or less than 2.0 liters. It is recognized that the capacity of the fluid waste receiver 12 can be commensurate with the purpose and/or location of the disposal assembly 10. For example, the disposal assembly 10 that is used inside of a patient's room can have a fluid waste receiver 12 with a relatively small capacity. Conversely, the disposal assembly 10 that is used in a pharmacy may have a fluid waste receiver 12 with a relatively large capacity.

The solid waste receiver 14 receives waste in a solid phase of matter. The design of the solid waste receiver 14, including the size, volume, shape and specific materials that form the solid waste receiver 14, can vary depending upon the design requirements of the disposal assembly 10. In the embodiment illustrated in FIG. 1A, the solid waste receiver 14 includes a solid receiver cap 20 that can be substantially similar to the fluid receiver cap 18 previously described. In one embodiment, the solid receiver cap 20 can be a tamper-resistant, locking cap that is positioned on the solid waste receiver 14 once the solid waste receiver 14 has reached a predetermined capacity or weight of solid waste, has been in use for a predetermined duration of time, or is otherwise determined to be no longer suitable for receiving solid waste.

In one embodiment, the solid waste receiver 14 can have a capacity of approximately 1.0 liter. Alternatively, the solid waste receiver 14 can have a capacity of greater than or less than 1.0 liter. Somewhat similar to the fluid waste receiver 12, it is recognized that the capacity of the solid waste receiver 14 can be commensurate with the purpose and/or location of the disposal assembly 10. For example, the disposal assembly 10 that is used inside of a patient's room can have a solid waste receiver 14 with a relatively small capacity. Conversely, the disposal assembly 10 that is used in a pharmacy may have a solid waste receiver 14 with a relatively large capacity.

The solid waste receiver 14 includes a solid receiver body 21 that contains the solid waste. The solid receiver body 21 can be formed from any suitably durable materials. In one embodiment, the solid receiver body 21 can be formed from a durable plastic material. Alternatively, the solid receiver body 21 can be formed from glass, ceramic, various metals, or a composite material, as non-exclusive examples. In one embodiment, the material that forms the solid receiver body 21 can be clear or otherwise see-through to allow a user to observe the level of waste within the solid waste receiver 14. Alternatively, the material that forms the solid receiver body 21 can be opaque or otherwise non-see-through.

In one embodiment, the solid waste receiver 14 is a separate structure from the fluid waste receiver 12. In an alternative embodiment, the solid waste receiver 14 and the fluid waste receiver 12 can be integrated and formed as a unitary structure.

In the embodiment illustrated in FIG. 1A, the receiver retainer 16 retains the fluid waste receiver 12 and the solid waste receiver 14. In an alternative embodiment (not shown), the receiver retainer 16 can retain either the fluid waste receiver 12 or the solid waste receiver 14. In the embodiment illustrated in FIG. 1A, the receiver retainer 16 includes a retainer housing 22 including one or more retainer side walls 24, a retainer base 26 and a retainer lid 28. In one embodiment, the retainer housing 22 includes four retainer side walls 24, although it is recognized that the retainer housing 22 can include any suitable number of retainer side walls 24. Further, although the retainer housing 22 illustrated in FIG. 1A has a rectangular configuration, it is understood that the retainer housing 22 can have another suitable configuration, such as cylindrical, triangular, pyramidal, rhomboidal or any other suitable three-dimensional polygonal configuration.

In the embodiment illustrated in FIG. 1A, one or more of the retainer side walls 24 can include one or more viewing windows 30 to allow a user to view a fluid waste level 33F and/or a solid waste level 33S in the corresponding waste receiver 12, 14. This design provides an alternative or backup means for determining whether the particular waste receiver 12, 14 needs to be removed and replaced based on the amount of waste in the waste receiver 12, 14.

In the embodiment illustrated in FIG. 1A, the retainer base 26 can include various indicator devices to inform the user of certain useful information. For example, in one embodiment, the retainer base 26 can include a charged battery indicator 32 and/or a low battery indicator 34. These indicators 32, 34 can be in the form of lights, audible indicators, digital readouts, gauges, or any other suitable type of indicator. These indicators 32, 34 automatically activate depending upon the charge status of a electrochemical cell structure 68 e.g., battery (illustrated in FIG. 1C).

The retainer base 26 may also include one or more fluid waste receiver indicators 36 (only one fluid receiver indicator 36 is illustrated in FIG. 1A) and/or one or more solid waste receiver indicators 38 (only one solid receiver indicator 38 is illustrated in FIG. 1A). The purpose for and number of the waste receiver indicators 36, 38 can vary. For example, the waste receiver indicators 36, 38 can alert the user that a predetermined capacity and/or weight of one or both of the waste receivers 12, 14 has been reached or exceeded. Alternatively, or in addition, the indicators 36, 38 can alert the user that a predetermined date and/or time has arrived, which can signal a requirement or recommendation for immediate or imminent removal and/or replacement of one or both of the waste receivers 12, 14. The indicators 36, 38 can be in the form of one or more lights, audible alerts, digital readouts, gauges, or any other suitable type of indicator for providing a user with certain useful information pertaining to one or more of the waste receivers 12, 14 and/or their contents. Additionally, although two indicators 36, 38 are illustrated in FIG. 1A, additional waste receiver indicators can be included.

As one non-exclusive example, in the event that the maximum time the fluid waste receiver 12 can be utilized is 90 days, one of the indicators 36, 38 can be activated a predetermined number of days before expiration of the 90 day period, i.e. 15 days prior, in order to provide sufficient time for the fluid waste receiver 12 to be removed, capped and shipped to the appropriate location for incineration or other permanent disposal. It is recognized that this example is provided for ease of understanding only, and is not intended to limit in any manner the time frames pertaining to usage of the indicators 36, 38. For instance, the maximum time can be greater or less than 90 days. Furthermore, activation of one of the indicators 36, 38 can occur greater than or less than 15 days prior to such expiration.

In certain embodiments, the disposal assembly 10 can include a controller 31 (illustrated in FIG. 1C) that can be retained in the retainer base 26. The controller 31 controls and or monitors various functions of the disposal assembly 10, including the activation of the indicators 32, 34 and/or the indicators 36, 38, as non-exclusive examples. In various non-exclusive embodiments, the controller 31 can include one or more types of electronics, printed circuit boards, integrated circuits, time-keeping devices and weight detection and/or monitoring devices, as described in greater detail herein. In addition, or in the alternative, the controller 31 can include one or more power supplies, such as electrochemical cell structures (not illustrated in FIG. 1A) that may be useful in providing power to the disposal assembly 10.

Figure 1B:
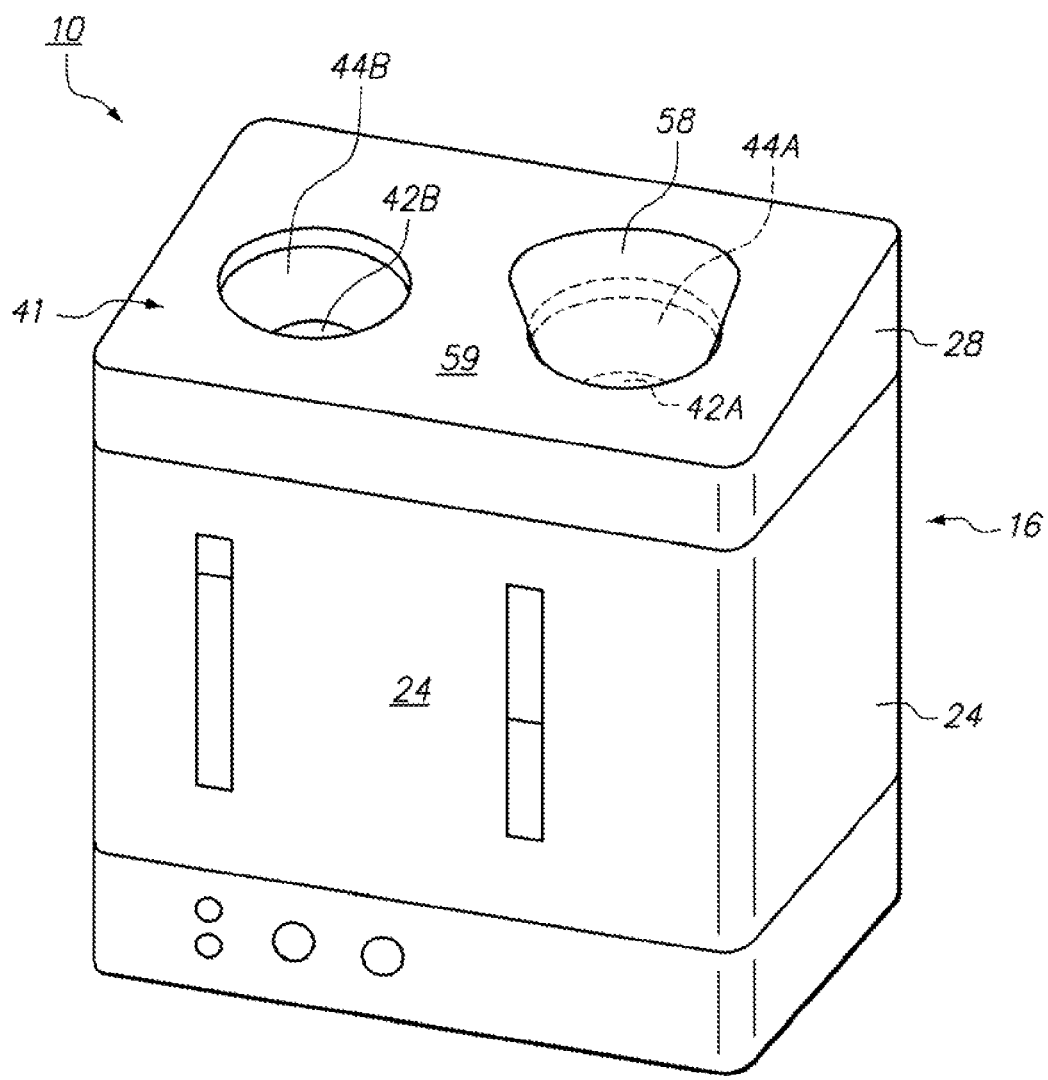
FIG. 1B is a perspective view of the pharmaceutical waste disposal assembly shown in FIG. 1A, illustrated in a closed position.

In one embodiment, the retainer lid 28 is movably secured to one of the retainer side walls 24, and can protect the contents of the retainer housing 22. Further, the retainer lid 28 selectively inhibits tampering or removal of the contents of the retainer housing 22. The retainer lid 28 can selectively be moved from the open position as illustrated in FIG. 1A to a closed position, as illustrated in FIG. 1B. The receiver retainer 16 can include a locking mechanism 1456 (illustrated in FIG. 14, for example) that allows the retainer lid 28 to be locked in place in the closed position. The retainer lid 28 can be hinged to one of the retainer side walls 24 with one or more hinges 40 (three hinges 40 are illustrated in FIG. 1A). Alternatively, other suitable structures known to those skilled in the art can movably secure the retainer lid 28 to one of the retainer side walls 24. Still alternatively, the retainer lid 28 can be completely removable from the retainer housing 22 such that the retainer lid 28 is not permanently secured to one of the retainer side walls 24.

In the embodiment illustrated in FIG. 1A, the retainer lid 28 includes an inner surface 39 and an opposing outer surface 41. The inner surface 39 is only visible when the receiver retainer 16 is in the open position, as illustrated in FIG. 1A. In this embodiment, the retainer lid 28 includes a lid top 43 and one or more lid apertures (two lid apertures 42A, 42B, are illustrated in FIG. 1A). The lid apertures 42A, 42B, allow fluid waste and/or solid waste to be deposited into one of the waste receivers 12, 14, from outside of the disposal assembly 10. In this embodiment, the lid apertures 42A, 42B, are positioned in, and extend through, the lid top 43. Alternatively, the lid apertures 42A, 42B, can be positioned on another surface of the retainer lid 28.

In one embodiment, one or more of the lid apertures 42A, 42B, can each include a waste guide 44A, 44B that assists in directing the specific phase of waste (solid, liquid or gas) to the appropriate waste receiver 12, 14. In non-exclusive embodiments, the waste guide 44A, 44B, can include a standard funnel-type device, a spiral funnel, or a series of diverters that guide the waste to the appropriate waste receiver 12, 14. The waste guides 44A, 44B, can further inhibit or prevent wrongful, illegal or unwanted extraction of waste from inside the receiver retainer 16 and/or the waste receivers 12, 14 by inhibiting or impeding hands or other objects from entering the interior of the retainer housing 22 and/or the waste receivers 12, 14 when the receiver retainer 16 is in the closed position.

The retainer housing 22 can also include one or more dividers 46 that compartmentalize the interior of the receiver retainer 16 for holding the waste receivers 12, 14, the receiver caps 18, 20, or other structures within the retainer housing 22. In the embodiment illustrated in FIG. 1A, the dividers 46 can divide the interior of the receiver retainer 16 into compartments including a fluid cap compartment 48 and a solid cap compartment 50. The receiver caps 18, 20 can be placed into their respective compartments 48, 50, in an untethered manner, or the receiver caps 18, 20, can be tethered to their respective waste receiver 12, 14, so that the receiver caps 18, 20, are not lost or otherwise inadvertently (and permanently) separated from their respective waste receivers 12, 14. Once one of the waste receivers 12, 14, is deemed to have expired, has reached a predetermined fill level, or otherwise needs to be removed from the receiver retainer 16, the corresponding receiver cap 18, 20, is positioned on the waste receiver 12, 14, for transport and/or further processing, such as by incineration as one non-exclusive example.

In the embodiment illustrated in FIG. 1A, the receiver retainer 16 also includes one or more waste receiver liners 52, 54. In this embodiment, the fluid waste receiver 12 can be positioned within a fluid waste receiver liner 52, and the solid waste receiver 14 can be positioned within a solid waste receiver liner 54. The waste receiver liners 52, 54 inhibit waste that may have been inadvertently spilled, or overflow waste, from coming into contact with the retainer housing 22, the controller 31, or other structures that may potentially be damaged by direct contact with the waste. One or more of the waste receiver liners 52, 54 can be fixedly in position within the retainer housing 22. Alternatively, one or more of the waste receiver liners 52, 54 can be removable from the retainer housing 22. Still alternatively, the waste receiver liners 52, 54 can be omitted from the receiver retainer 16.

It is important to note that in FIG. 1A and many of the other Figures, various structures are not necessarily shown to scale so that all structures may be adequately represented and visualized.

FIG. 1B is a perspective view of the pharmaceutical waste disposal assembly 10 illustrated in FIG. 1A, illustrated in a closed position. In this embodiment, the outer surface 41 of the retainer lid 28 is visible, but the inner surface 39 (illustrated in FIG. 1A) is within the interior of the receiver retainer 16. Further, in this embodiment, the lid apertures 42A, 42B, and the waste guides 44A, 44B, are likewise visible and accessible from the exterior of the receiver retainer 16. In the embodiment illustrated in FIG. 1B, the receiver retainer 16 includes a fluid waste diverter 58 that diverts waste through one of the lid apertures 42A, 42B, which may otherwise not have been properly aimed at or into one of the lid apertures 42A, 42B. In this embodiment, the waste diverter 58 is positioned at least partially around the lid aperture 42A, which is designed to receive fluid waste. However, it is understood that the fluid waste diverter 58 could have also or alternatively been positioned at least partially around the lid aperture 42B to guard against errant solid waste not being received by the lid aperture 42B.

In the embodiment illustrated in FIG. 1B, the retainer lid 28 includes a top surface 59 that is substantially planar. In one embodiment, the top surface 59 can be angled toward the user to allow easier deposition of fluids and solids into the disposal assembly 10. Alternatively, the top surface 59 can be flat, i.e. perpendicular to one or more of the retainer side walls 24 (two side walls 24 are illustrated in FIG. 1B). Still alternatively, the top surface 59 can be angled away from a user, or can be angled to one side or another. In another embodiment, the top surface 59 can have a non-planar configuration, i.e. curved, multi-faceted, etc.

Figure 1C:
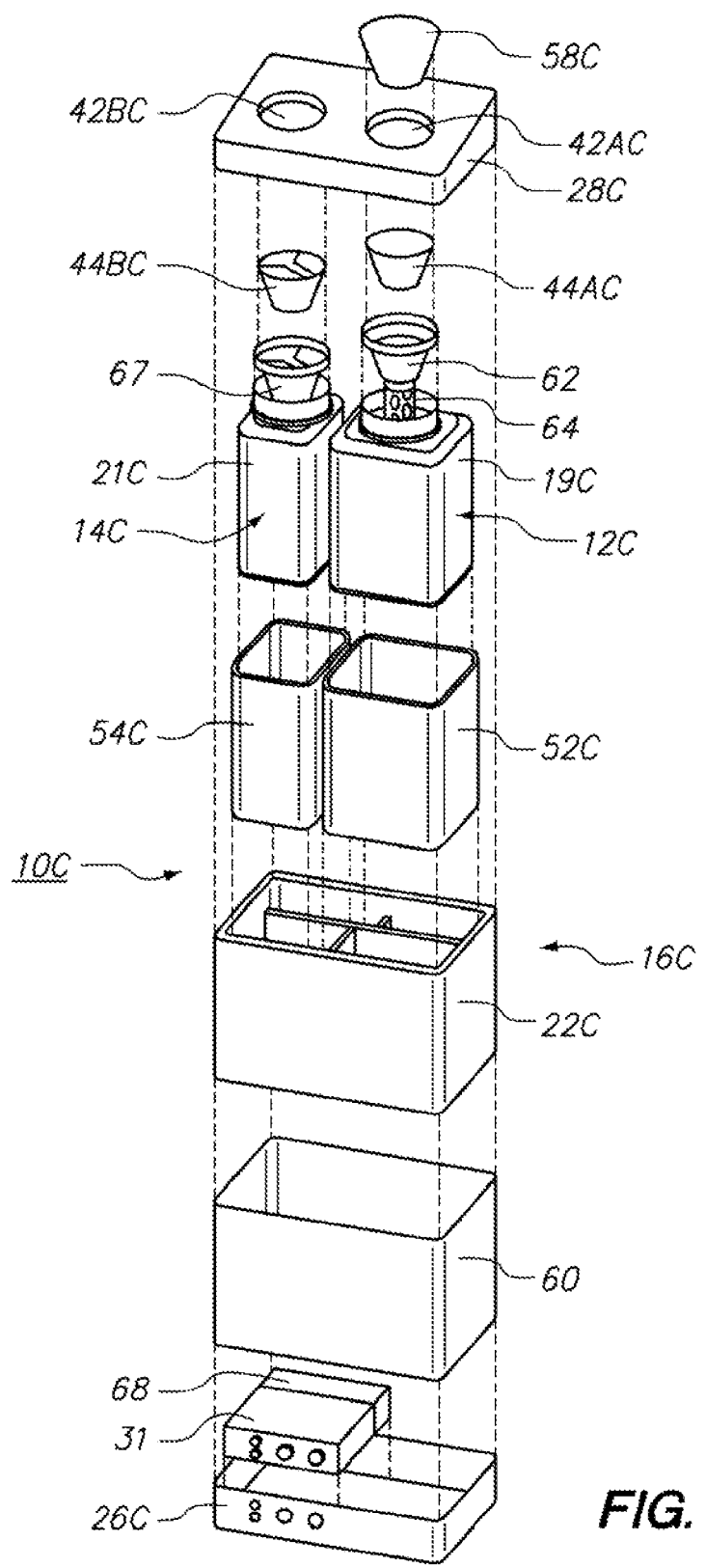
FIG. 1C is an exploded view of the pharmaceutical waste disposal assembly illustrated in FIG. 1A.

FIG. 1C is an exploded view of one embodiment of a disposal assembly 10C. In this embodiment, the disposal assembly 10C includes a fluid waste receiver 12C, a solid waste receiver 14C and a receiver retainer 16C. The positioning of the fluid waste receiver 12C and the solid waste receiver 14C relative to the receiver retainer 16C can vary from that shown in FIG. 1C. In this embodiment, the fluid waste receiver 12C includes a fluid receiver guide 62 (also sometimes referred to herein as "receiver guide") that guides the fluid waste into the fluid receiver body 19C. The fluid receiver guide 62 can include a standard funnel-type device, a spiral funnel, or a series of diverters. The fluid receiver guide 62 can further inhibit or prevent wrongful, illegal or unwanted extraction of waste from inside the fluid waste receiver 12C by inhibiting or impeding hands or other objects from entering the fluid receiver body 19C. In the embodiment illustrated in FIG. 1C, the fluid receiver guide 62 can include a fluid distributor 64 that directly distributes and/or disperses fluid to different levels within the fluid waste receiver 12C, as described in greater detail herein. Alternatively, the fluid receiver guide 62 and the fluid distributor 64 can be separate and/or spaced-apart structures within the fluid waste receiver 12C.

The solid waste receiver 14C includes a solid receiver guide 67 that guides the fluid waste into the solid receiver body 21C. The solid receiver guide 67 can include a standard funnel-type device, a spiral funnel, or a series of diverters. The solid receiver guide 67 can further inhibit or prevent wrongful, illegal or unwanted extraction of waste from inside the solid waste receiver 14C by inhibiting or impeding hands or other objects, from entering the solid receiver body 21C.

The receiver retainer 16C includes a retainer housing 22C, a retainer base 26C, and a retainer lid 28C having a waste diverter 58C, which are substantially similar to those previously described. The disposal assembly 10C also includes a controller 31 which can control and/or monitor various functions of the disposal assembly 10C, including the activation of the indicators 32, 34 (illustrated in FIG. 1A) and/or the indicators 36, 38 (illustrated in FIG. 1A), as non-exclusive examples. In various non-exclusive embodiments, the controller 31 can include one or more types of electronics, printed circuit boards, integrated circuits, time-keeping devices and weight detection and/or monitoring devices, as described in greater detail herein. In addition, or in the alternative, the controller 31 can include one or more power supplies, such as electrochemical cell structures 68 that may be useful in providing power to the disposal assembly 10C. In one embodiment, the controller 31 can be a separate, removable structure that can be removed in the event of a malfunction, for the purpose of upgrading/updating the controller 31, to service the controller 31, or once the controller 31 reaches the end of its useful life.

In this embodiment, the retainer lid 28C includes one or more lid apertures (two lid apertures 42AC, 42BC, are illustrated in FIG. 1C). The lid apertures 42AC, 42BC function substantially in the same manner as those previously described herein, allowing fluid waste and/or solid waste to be deposited into one of the waste receivers 12C, 14C, from outside of the disposal assembly 10C. In this embodiment, the lid apertures 42AC, 42BC, are positioned in, and extend through, the lid top 43.

In the embodiment illustrated in FIG. 1C, the lid apertures 42AC, 42BC, each includes a corresponding waste guide 44AC, 44BC that assists in directing the specific phase of waste (solid, liquid or gas) to the appropriate waste receiver 12C, 14C. The waste guides 44AC, 44BC can include a standard funnel-type device, a spiral funnel, or a series of diverters that guide the waste to the appropriate waste receiver 12C, 14C, in a manner substantially similar or identical to that previously described herein.

In the embodiment illustrated in FIG. 1C, the receiver retainer 16C also includes one or more waste receiver liners 52C, 54C, described previously herein. Further, in this embodiment, the disposal assembly 10C can also include a retainer sleeve 60 that encircles at least a portion of the retainer housing 22C. The retainer sleeve 60 can be formed from various plastic materials or other synthetic materials, metal, various composites, or any other suitable materials. The sleeve can provide added sheer strength to the disposal assembly 10C and/or can provide a decorative surface that is aesthetically pleasing in a hospital or health care facility setting.

Figure 2:
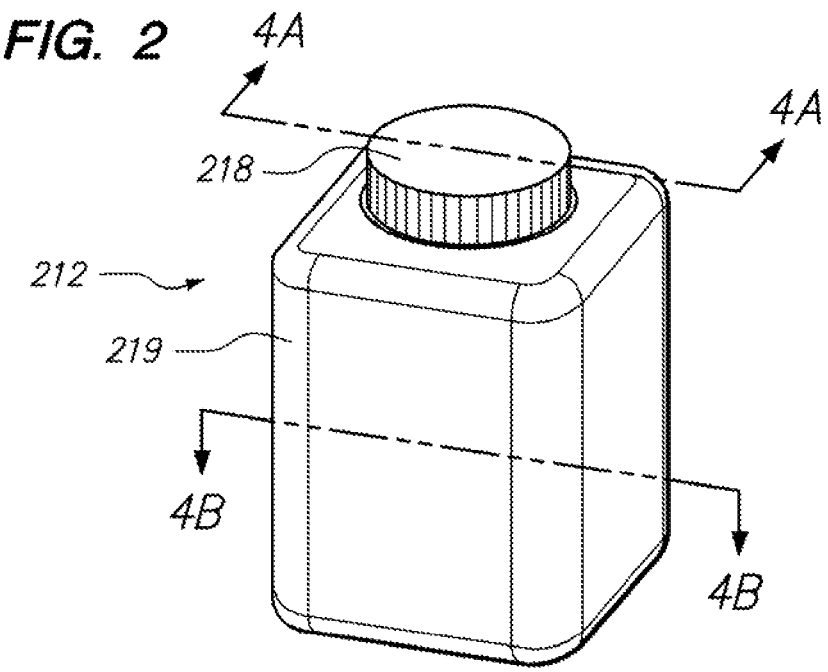
FIG. 2 is a perspective view of one embodiment of the fluid waste receiver having features of the present invention.

FIG. 2 is a perspective view of one embodiment of a fluid waste receiver 212 including the fluid receiver cap 218 and the fluid receiver body 219. The specific configuration of the fluid receiver body 219 of the fluid waste receiver 212 can vary depending upon the design requirements of the disposal assembly 10. In the embodiment illustrated in FIG. 2, the fluid receiver body 219 has a somewhat rectangular shape. Alternatively, the fluid receiver body 219 can be conical, frusto-conical, cubical, spherical, pyramidal, or can have any other suitable shape.

Figure 3:
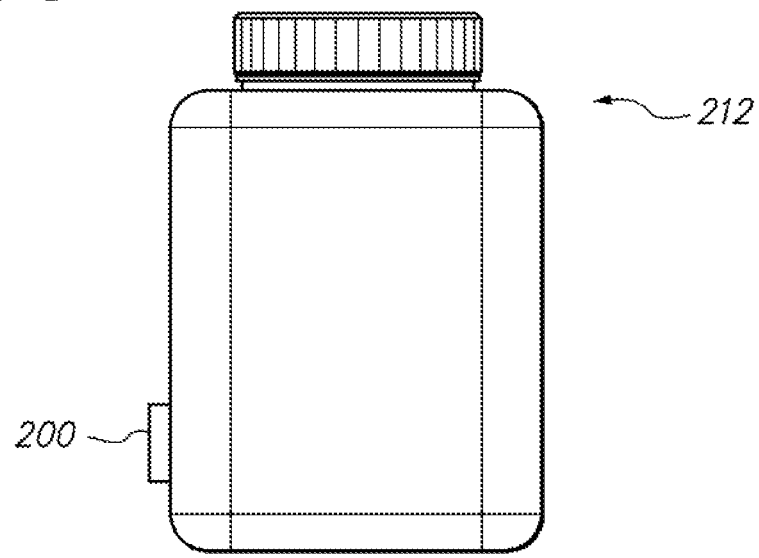
FIG. 3 is a front elevation view of the fluid waste receiver illustrated in FIG. 2.

FIG. 3 is a front elevation view of the fluid waste receiver 212 illustrated in FIG. 2. In FIG. 3, the fluid waste receiver 212 has curved, e.g., radiused, corners and edges. Additionally, in this embodiment, the fluid waste receiver 212 includes an identification tag 200. In one embodiment, the identification tag 200 can be used in conjunction with an identification reader 1500 (illustrated in FIG. 15) that is positioned on another structure of the disposal assembly 1510, such as the receiver retainer 1516 (illustrated in FIG. 15, for example), as set forth in greater detail below. In one embodiment, the identification tag 200 can be a radio frequency identification ("RFID") tag. In addition, or in the alternative, the identification tag 200 can include a barcode label, a printed serial number, an integrated circuit, and/or any other suitable type of identifier of the particular fluid waste receiver 212. In another embodiment, the identification tag 200 can be used independently of any type of identification reader such that the identification tag 200 is used as a "stand alone" identifier of the fluid waste receiver 212.

The identification tag 200 can include an active RFID tag, which can contain a battery and can transmit signals autonomously. Alternatively, the identification tag 200 can include a passive RFID tag, which can have no battery and can require an external source to provoke signal transmission. Still alternatively, the identification tag 200 can include a battery assisted passive (BAP) RFID tag, which can require an external source to wake up but have significant higher forward link capability providing greater range.

Figure 4A:
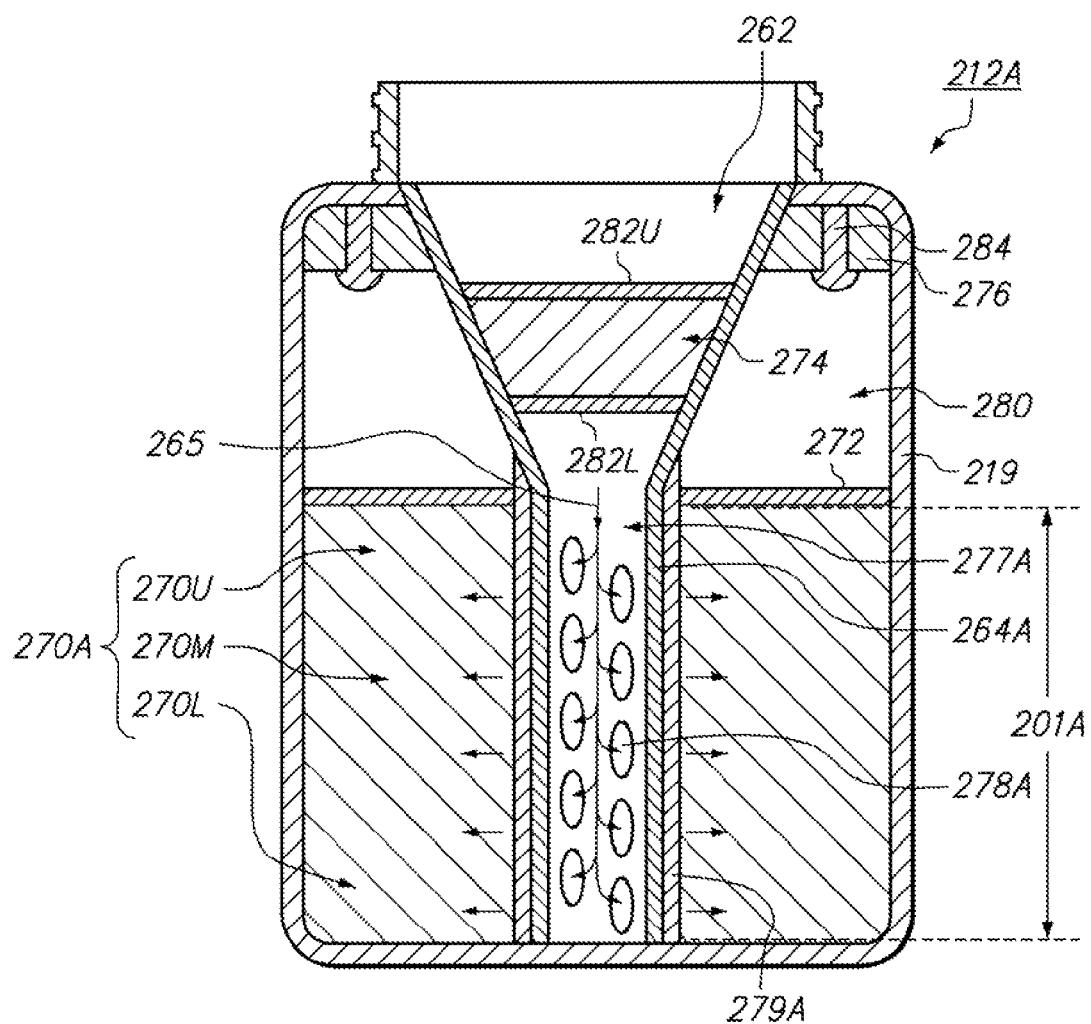
FIG. 4A is a cross-sectional view of a portion of the fluid waste receiver taken on line 4A-4A in FIG. 2.

FIG. 4A is a cross-sectional view of the fluid waste receiver 212A taken on line 4A-4A in FIG. 2, with the fluid receiver cap 218 (illustrated in FIG. 2) removed for clarity. In the embodiment illustrated in FIG. 4A, the fluid waste receiver 212A includes the identification tag 200 (illustrated in FIG. 4B), a fluid receiver body 219, a fluid receiver guide 262, a fluid distributor 264A, a fluid absorber 270A, an absorber retainer 272, a fluid processor 274 and a fluid deodorizer 276. The fluid receiver guide 262 is substantially similar or identical to the fluid receiver guide 62 previous described herein.

In certain embodiments, the fluid distributor 264A receives fluid waste via the fluid receiver guide 262 and can directly distribute and/or allow the fluid waste to flow to one or more levels 270L, 270M, 270U of the fluid absorber 270A in a more even (e.g., non-random) manner, as illustrated by arrows 265. As used herein, the term "directly distribute" means that migration of the fluid waste from one level 270L, 270M, 270U to another is not necessary because due to its design, the fluid distributor 264A allows the fluid waste to initially enter the fluid absorber 270A at each of the levels 270L, 270M, 270U, rather than at one single level. With this design, the fluid waste can more rapidly be absorbed by the fluid absorber 270A, which inhibits puddling or ponding of fluid waste within the fluid waste receiver 212A.

The shape and positioning of the fluid distributor 264A relative to the fluid waste receiver 212A can vary depending upon the design requirements of the fluid waste receiver 212A. In one embodiment, the fluid distributor 264A can have a substantially tubular shape with a circular cross-section, as illustrated in FIG. 4B. Alternatively, the fluid distributor 264A can have a different shape and/or a different cross-section. In alternative non-exclusive embodiments, for example, the fluid distributor 264A can have a conical, frustoconical, pyramidal, hourglass or other suitable shape. Further, in alternative non-exclusive embodiments, the fluid distributor 264A can have an elliptical, triangular, square, hexagonal, or any other suitable polygonal or irregular cross-sectional shape in order to accomplish the desired fluid distribution of the fluid waste to the fluid absorber 270A. In one embodiment, the fluid distributor 264A can be formed from a durable plastic material. Alternatively, the fluid distributor 264A can be formed from another suitable material, such as metal, various composite materials, glass, fiberglass, ceramic, or any other relatively durable materials.

In addition, the extent to which the fluid distributor 264A extends into the fluid waste receiver 212A can vary. For example, the fluid distributor 264A need not extend all the way to a bottom of the fluid waste receiver 212A as illustrated in FIG. 4A. Stated another way, the fluid distributor 264A has a length 201A that can be varied to suit the design requirements of the fluid waste receiver 212A. In one embodiment, the fluid distributor 264A can have a shorter length 201A relative to the fluid waste receiver 212A than that illustrated in FIG. 4A.

In one embodiment, the fluid distributor 264A can include a plurality of distributor apertures 278A that enable the fluid waste to directly flow in accordance with the arrows 265 into the fluid absorber 270A at various vertical levels within the fluid waste receiver 212A. With this design, the fluid distributor 264A acts as a temporary reservoir until the fluid waste moves through the distributor apertures 278A and is at least partially or fully absorbed by the fluid absorber 270A. Further, the fluid distributor 264A can more evenly and directly distribute the fluid waste to various levels 270L, 270M, 270U of the fluid absorber 270A, i.e. a lower level 270L, a middle level 270M and an upper level 270U of the fluid absorber 270A. Stated another way, the fluid distributor 264A inhibits any one level 270L, 270M, 270U within the fluid absorber 270A from having to absorb substantially more fluid waste than any other level 270L, 270M, 270U. Further, the fluid distributor 264A can inhibit the fluid waste from simply collecting on the upper level 270U of the fluid absorber 270A. Because the fluid distributor 264A extends through at least a portion of the fluid absorber 270A, the fluid waste does not need to diffuse through the upper level 270U to reach the middle and lower levels 270M, 270L, resulting in more rapid absorption of the fluid waste by the fluid absorber 270A.

As used herein, the term "levels" of the fluid absorber 270A refers to vertical levels that have relative positioning within the fluid receiver body 219. For example, the lower level 270L is positioned adjacent to and/or near a receiver bottom 283 (illustrated in FIG. 4C). The upper level 270U is positioned furthest away from the receiver bottom 283, e.g., in one embodiment, adjacent to or near the absorber retainer 272. The middle level 270M is positioned between the lower level 270L and the upper level 270U. In the embodiment illustrated in FIG. 4A, the fluid distributor 264A extends downwardly from the fluid receiver guide 262 at least partially, if not fully, through the various levels 270L, 270M, 270U of the fluid absorber 270A.

The size, shape, density and number of distributor apertures 278A can vary depending upon the requirements of the fluid waste receiver 212A and/or the shape and/or size of the fluid absorber 270A, and/or the material used to form the fluid absorber 270A. In one embodiment, all of the distributor apertures 278A are substantially similar in size and/or shape. In another embodiment, the sizes of the distributor apertures 278A can be different depending upon their location on the fluid distributor 264A. In still another embodiment, the density of distributor apertures 278A can be substantially similar over the length 201A of the fluid distributor 264A. Alternatively, the density of distributor apertures 278A can vary over the length 201A of the fluid distributor 264A. The foregoing embodiments are provided as examples only, and are not intended to be limiting in any manner. For example, in another embodiment, one fluid distributor 264A can combine varying sizes, shapes and densities of distributor apertures 278A.

In one embodiment, the fluid distributor 264A can include a distributor sleeve 279A that inhibits any portion of the fluid absorber 270A from entering into the fluid distributor 264A through any of the distributor apertures 278A. The distributor sleeve 279A can include a fluid-permeable material that wraps partially or fully around the fluid distributor 264A to act as a fluid-permeable barrier between a distributor interior 277A of the fluid distributor 264A and the portion of the fluid receiver body 219 that contains the fluid absorber 270A. Importantly, the distributor sleeve 279A does not unduly impede fluid flow from the distributor interior 277A of the fluid distributor 264A out through the distributor apertures 278A and into the fluid absorber 270A. In one embodiment, the distributor sleeve 279A can be formed from a material such as a durable fabric-type material. Alternatively, the distributor sleeve 279A can be formed from a plastic material, or any other suitably durable, yet fluid-permeable, material.

The fluid absorber 270A absorbs fluid waste that enters the fluid distributor 264A. In one embodiment, the fluid absorber 270A includes a solid material such as a super absorbent polymer (SAP), which can also be combined with additional fluff or fibrous materials, for example. Alternatively, the fluid absorber 270A can include other suitable, relatively absorbent materials. The material that forms the fluid absorber 270A can also include antibacterial, antimicrobial, and/or anti-odor characteristics. In one embodiment, the fluid absorber 270A can be impregnated with a silver or copper type of antibacterial and/or antimicrobial agent to reduce or eliminate the possibility of bacterial or fungal growth. In one embodiment, the fluid absorber 270A can convert the fluid waste to a gelatinous or solid material that is less likely to spill or leak from the fluid waste receiver 212A.

The absorber retainer 272 maintains the positioning of the fluid absorber 270A within the fluid waste receiver 212A. In one embodiment, the absorber retainer 272 can include a fluid-permeable screen, such as a plastic or wire mesh screen. Alternatively, the absorber retainer 272 can be a substantially fluid-impermeable layer. By maintaining the position of the fluid absorber 270A, the absorber retainer 272 also maintains a gap region 280 within the fluid waste receiver 212A, and acts as a fluid permeable barrier between the fluid absorber 270A and the gap region 280. Additionally, the gap region 280 acts as an overflow reservoir that holds unabsorbed fluid waste, if necessary, until the fluid waste can be absorbed by the fluid absorber 270A.

The fluid processor 274 can process the fluid waste in one or more ways. For example, the fluid processor 274 can include a deodorizer, an antimicrobial agent, an antibacterial agent and/or an antifungal agent. The fluid processor 274 can also include an upper solid waste filter 282U and/or a lower solid waste filter 282L that inhibit or prevent solid waste, such as pills, capsules, syringes, needles, etc., or portions thereof, or particles from the fluid processor 274 from entering into the fluid distributor 264A. Further, in certain embodiments, the solid waste filters 282U, 282L can act as an additional barrier to inhibit or prevent portions of the fluid absorber 270A from exiting the fluid waste receiver 212 in the event the fluid waste receiver is inverted. The solid waste filters 282U, 282L can include a screen or mesh material, or another suitable fluid-permeable structure.

The fluid deodorizer 276 deodorizes the fluid waste that enters the fluid waste receiver 212A. In the embodiment illustrated in FIG. 4A, the fluid deodorizer 276 is secured to an upper portion of the fluid receiver body 219 with one or more deodorizer fasteners 284. The fasteners 284 can include pins, screws, or any other suitable fasteners. It is understood that in other embodiments, the fluid deodorizer 276 can be positioned in other locations within the fluid waste receiver 212A, and that the example provided in FIG. 4A is only provided as one workable position for the fluid deodorizer 276, and is not intended to limit the invention in any manner. In one embodiment, the fluid deodorizer 276 can be somewhat similar to the material that forms the fluid processor 274. In non-exclusive alternative embodiments, the fluid deodorizer 276 can include a carbon-based filter, a scented deodorizer, or another suitable structure that performs the intended function of deodorizing the interior of the fluid receiver body 219.

FIG. 4B is a cross-sectional view of the fluid waste receiver 212A taken on line 4B-4B in FIG. 2. In this embodiment, the fluid distributor 264A is substantially centrally positioned within the fluid receiver body 219. In an alternative embodiment, the fluid distributor 264A can be positioned off-center within the fluid receiver body 219. Still alternatively, the fluid distributor 264 can include greater than one tubular (or other shaped) section that extends into the fluid absorber 270A. Stated another way, the fluid distributor 264A can have a plurality of distributor branches (such as those illustrated in FIG. 4K, for example) that extend into the fluid absorber 270A. In the embodiment illustrated in FIG. 4B, the fluid absorber 270A encircles or surrounds the fluid distributor 264A to substantially fill a space between the fluid receiver body 219 and the distributor sleeve 279A of the fluid distributor 264A. In an alternative embodiment, there may be voids or gaps between the fluid absorber 270A and the fluid receiver body 219. In the embodiment illustrated in FIG. 4B, the distributor apertures 278A are positioned at various points around the circumference of the fluid distributor 264A. It is understood, however, that the positioning of distributor apertures 278A can vary from that illustrated in FIG. 4B.

FIG. 4C is a cross-sectional view of a portion of another embodiment of the fluid waste receiver 212C. In this embodiment, the fluid waste receiver 212C is substantially similar to the fluid waste receiver 212A illustrated in FIG. 4A, except for certain modifications noted herein. So as not to obscure the features described relative to FIG. 4C, many of the features of the fluid waste receiver 212A illustrated in FIG. 4A have been omitted from FIG. 4C.

In the embodiment illustrated in FIG. 4C, the fluid receiver 212C includes a receiver bottom 283 that supports the fluid absorber 270C. In this embodiment, the fluid distributor 264C extends from the fluid receiver guide 262 to a point above the receiver bottom 283. Stated another way, the fluid distributor 264C does not extend all the way to the receiver bottom 283, but stops short of the receiver bottom 283. With this design, fluid waste can not only migrate out of the distributor apertures 278C into the fluid absorber 270C, but the fluid waste can also migrate out of the fluid distributor 264C through a distributor bottom 285 of the fluid distributor 264C. In one embodiment, the distributor bottom 285 can be partially or completely open, with the exception of the distributor sleeve 279C which may cover some or the entire distributor bottom 285 in a fluid-permeable manner. Therefore, in one embodiment, the distributor sleeve 279C can inhibit or prevent the material that forms the fluid absorber 270C from migrating in an upwardly direction into the fluid distributor 264C.

Figure 4D:
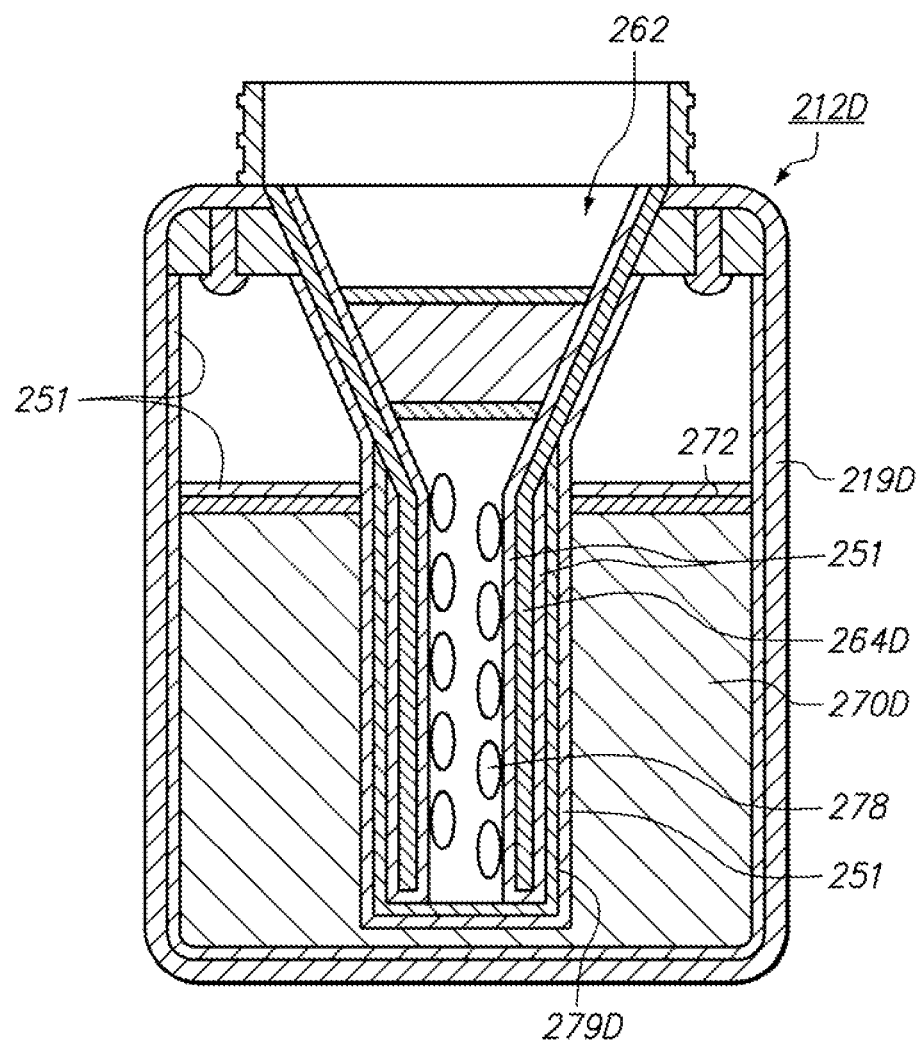
FIG. 4D is a cross-sectional view of a portion of yet another embodiment of the fluid waste receiver.

FIG. 4D is a cross-sectional view of a portion of yet another embodiment of the fluid waste receiver 212D. In this embodiment, the fluid waste receiver 212D includes an antimicrobial layer 251 that thinly coats at least portions of one or more structures within the fluid waste receiver 212D. For example, in the embodiment illustrated in FIG. 4D, the antimicrobial layer 251 can be positioned on one or more surfaces of the fluid receiver body 219, the fluid distributor 264D, the absorber retainer 272, the distributor sleeve 279D, and/or any other suitable surface within the fluid waste receiver 212D. In one non-exclusive embodiment, the antimicrobial layer 251 can be formed from materials that can disrupt the ability of germs and other bacteria from adhering to or reproducing on surfaces of the fluid waste receiver 212D. However, it is recognized that any suitable antimicrobial agent known to those skilled in the art can be used to form the antimicrobial layer 251. Further, the thickness of the antimicrobial layer 251 can vary as required to suit the design requirements of the fluid waste receiver 212D based on knowledge of those skilled in the art. In one embodiment, the thickness of the antimicrobial layer 251 can be one micron or less. Alternatively, the thickness of the antimicrobial layer 251 can be within the range of 1-500 microns, or greater.

FIG. 4E is a cross-sectional view of another embodiment of a portion of the fluid waste receiver 212E, including the fluid receiver guide 262E and the fluid distributor 264E. In this embodiment, the fluid distributor 264E includes a plurality of substantially oval or elliptical distributor apertures 278E that increase in size along the length 201E of the fluid distributor 264E in the direction from the fluid receiver guide 262E toward the distributor bottom 285E. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A. Although in this embodiment, the distributor apertures 278E are shown as being substantially evenly spaced and similar in shape, it is understood that the distributor apertures 278E can be dissimilar in shape and/or unevenly spaced, and/or can have a different shape than that illustrated in FIG. 4E. In an alternative embodiment (not shown), the distributor apertures 278E can decrease in size along the length 201E of the fluid distributor 264E in the direction from the fluid receiver guide 262E toward the distributor bottom 285E.

FIG. 4F is a cross-sectional view of another embodiment of a portion of the fluid waste receiver 212F, including the fluid receiver guide 262F and the fluid distributor 264F. In this embodiment, the fluid distributor 264F includes a plurality of substantially slit-shaped distributor apertures 278F that are substantially similar in size, but are more dense, e.g., more numerous, in the direction from the fluid receiver guide 262F toward the distributor bottom 285F. Stated another way, a spacing between the distributor apertures 278F along a direction along the length 201F of the fluid distributor 264F is non-uniform. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A. In an alternative embodiment (not shown), the distributor apertures 278F are less dense, e.g., less numerous, in the direction from the fluid receiver guide 262F toward the distributor bottom 285F.

FIG. 4G is a cross-sectional view of another embodiment of a portion of the fluid waste receiver 212G, including the fluid receiver guide 262G and the fluid distributor 264G. In this embodiment, the fluid distributor 264G includes a plurality of relatively small distributor apertures 278G that are substantially uniform in size over the length 201G of the fluid distributor 264G. In this embodiment, the fluid distributor 264G can include a screen-like material that forms the distributor apertures 278G. The distributor apertures 278G can be any suitable size that can allow passage of fluid waste out of the fluid distributor 264G and into the fluid absorber 270A (illustrated in FIG. 4A, for example).

FIG. 4H is a cross-sectional view of another embodiment of a portion of the fluid waste receiver 212H, including the fluid receiver guide 262H and the fluid distributor 264H. In this embodiment, the fluid distributor 264H includes a plurality of distributor apertures 278H that increase in number along the length 201H of the fluid distributor 264H in the direction from the fluid receiver guide 262H toward the distributor bottom 285H. Stated another way, a density of the distributor apertures 278H is non-uniform in a direction along the length 201 H of the fluid distributor 264H. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A. In an alternative embodiment (not shown), the distributor apertures 278H can decrease in number along the length 201H of the fluid distributor 264H in the direction from the fluid receiver guide 262H toward the distributor bottom 285H.

FIG. 4I is a cross-sectional view of another embodiment of a portion of the fluid waste receiver 212I, including the fluid receiver guide 262I and the fluid distributor 264I. In this embodiment, the fluid distributor 264I flares out along the length 201I of the fluid distributor 264I in a direction from the fluid receiver guide 262I toward the distributor bottom 285I. Stated another way, the fluid distributor 264I has an increasingly larger cross-sectional area moving from an upper portion 265UI toward a lower portion 265LI of the fluid distributor 264I. In addition, the fluid distributor 264I can include greater number of distributor apertures 278I along the length 201I of the fluid distributor 264I moving from the upper portion 265UI toward the lower portion 265LI of the fluid distributor 264I. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A.

FIG. 4J is a cross-sectional view of another embodiment of a portion of the fluid waste receiver 212J, including the fluid receiver guide 262J and the fluid distributor 264J. In this embodiment, the fluid distributor 264J includes a plurality of distributor apertures 278J that are substantially similar to those previously described relative to FIG. 4G. However, in this embodiment, the fluid distributor 264J flares out along the length 201J of the fluid distributor 264J moving from an upper portion 265UJ toward a lower portion 265LJ of the fluid distributor 264J, somewhat similarly to the embodiment described relative to FIG. 4I. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A.

Figure 4K:
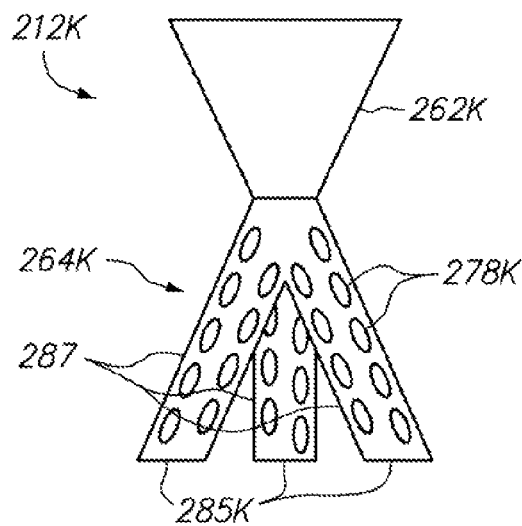
FIG. 4K is a side view of another embodiment of a portion of the fluid waste receiver.

FIG. 4K is a side view of another embodiment of a portion of the fluid waste receiver 212K, including the fluid receiver guide 262K and the fluid distributor 264K. In this embodiment, the fluid distributor 264K includes a plurality of distributor legs 287. In the embodiment illustrated in FIG. 4K, the fluid distributor 264K includes three distributor legs 287. However, in alternative embodiments, the fluid distributor 264K can include fewer than three or greater than three distributor legs 287. With this design, a greater and more evenly distributed surface area of the fluid absorber 270 (illustrated in FIG. 4A) can be directly accessible to the fluid waste exiting the fluid distributor 264K via the distributor apertures 278K. In one embodiment, fluid waste can also emanate from the fluid distributor 264K via the distributor bottom 285K of one or more of the distributor legs 287. In one embodiment, the distributor legs 287 can have a substantially similar length to one another. Alternatively, the distributor legs 287 can have different lengths from one another.

Figure 5A:
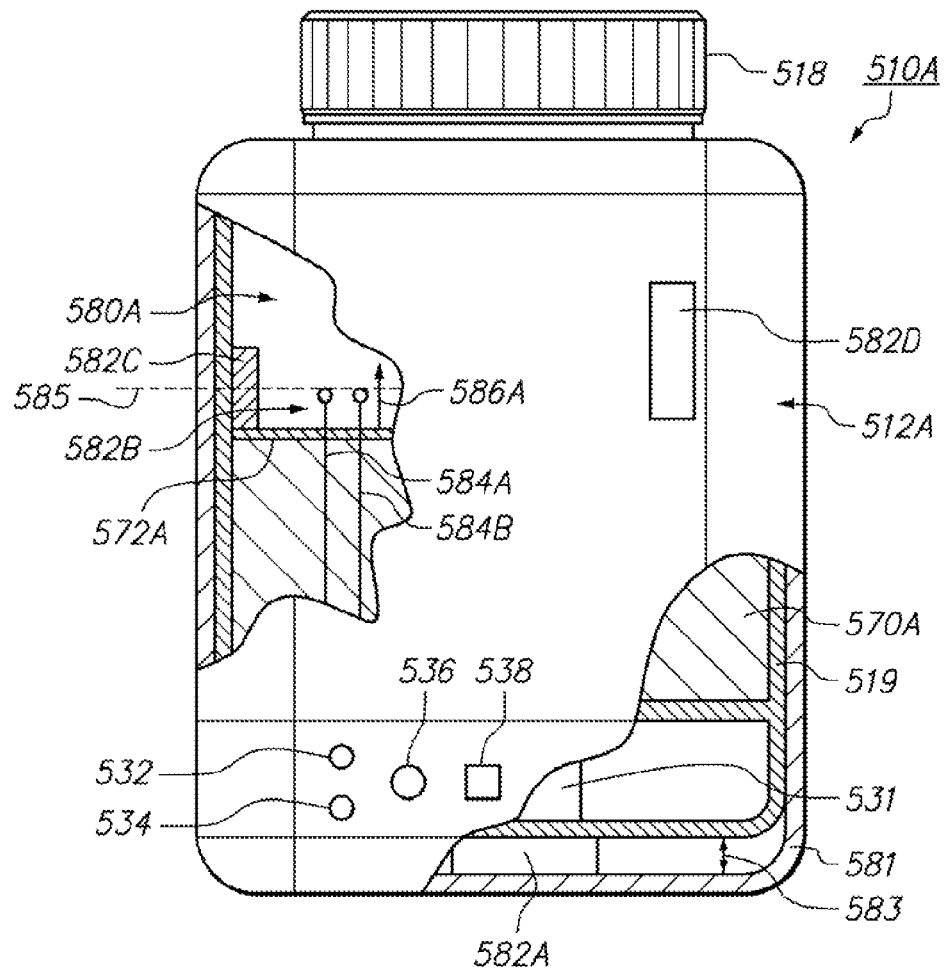
FIG. 5A is a partial cutaway view of another embodiment of the pharmaceutical waste disposal assembly having features of the present invention.

FIG. 5A is a partial cutaway view of another embodiment of a disposal assembly 510A including a fluid waste receiver 512A. In this embodiment, the fluid waste receiver 512A is fully self-contained and is not used in conjunction with a separate receiver retainer (such as receiver retainer 16 illustrated in FIG. 1A). Although not necessarily illustrated in FIG. 5A, the fluid waste receiver 512A can include some or all of the same components illustrated and described relative to FIGS. 2, 4A and 4B, including one or more of the fluid receiver guide 262, the fluid distributor 264, the fluid processor 274 and the fluid deodorizer 276, which function substantially as described previously herein.

Additionally, in the embodiment illustrated in FIG. 5A, the disposal assembly 510A includes a fluid receiver cap 518, a fluid receiver body 519, a controller 531, a charged battery indicator 532, a low battery indicator 534, a fluid waste receiver indicator 536, a fluid absorber 570A, an absorber retainer 572A, and an gap region 580A, which function substantially as previously described herein, with the exception of certain modifications provided below. Further, the disposal assembly 510A can also include a timer activator 538, a fluid receiver body retainer 581 and one or more fluid waste receiver sensors 582A, 582B, 582C, 582D.

In one embodiment, the fluid receiver body 519 is positioned within and is movable relative to the fluid receiver body retainer 581 in a direction illustrated by arrow 583. Movement of the fluid receiver body 519 relative to the fluid receiver body retainer 581 only needs to be slight, and is dependent upon the weight of the contents of the fluid receiver body 519, including any fluid waste which may be present within the fluid receiver body 519. In the embodiment illustrated in FIG. 5A, a fluid waste receiver sensor 582A is positioned between the fluid receiver body 519 and the fluid receiver body retainer 581. In one embodiment, the fluid waste receiver sensor 582A is a weight sensor, such as a load cell, for example. In this embodiment, as the weight of the fluid receiver body 519 and its contents increases, a greater force is exerted on the weight sensor 582A.

In one embodiment, the weight sensor 582A can convert a predetermined force into an electrical signal, which causes the fluid waste receiver indicator 536 to activate. Activation of the fluid waste receiver indicator 536 can alert a user that the fluid waste has reached a predetermined percentage of the capacity of the fluid receiver body 519, and the user has a certain predetermined time period to place the fluid receiver cap 518 on the fluid receiver body 519, which prepares the disposal assembly 510A for disposal. In various embodiments, the predetermined force required to activate the fluid waste receiver indicator 536 and/or the predetermined percentage of the capacity of the fluid receiver body 519 can be determined based upon various requirements of the specific regulations governing disposal of waste. Alternatively, the predetermined force required to activate the fluid waste receiver indicator 536 and/or the predetermined percentage of the capacity of the fluid receiver body 519 can be determined by the user, and can be programmed into the controller 531.

In one embodiment, the fluid waste receiver indicator 536 can be activated by the fluid waste receiver sensor 582B. In this embodiment, the fluid waste receiver sensor 582B includes two or more electrical conductors 584A, 584B that form a circuit once the liquid waste has reached a predetermined height (indicated by dashed line 585) within the fluid receiver body 519. Once the circuit has been formed, the fluid waste receiver sensor 582B sends an electrical signal to the controller 531, which then activates the fluid waste receiver indicator 536 to alert a user that the fluid waste has reached a predetermined percentage of the capacity of the fluid receiver body 519. At this point, in one embodiment, the user would have a certain predetermined time period to place the fluid receiver cap 518 on the fluid receiver body 519, which prepares the disposal assembly 510A for disposal.

In another embodiment, the fluid waste receiver indicator 536 can be activated by the fluid waste receiver sensor 582C. In this embodiment, as the fluid absorber 570A expands once a particular amount of fluid waste has been absorbed by the fluid absorber 570A, the absorber retainer 572A will move in an upward direction as indicated by arrow 586A. This upward movement generates a force against the fluid waste receiver sensor 582C. Once a predetermined force has been achieved, the fluid waste receiver sensor 582C transmits an electrical signal to the controller 531. The controller 531 then activates the fluid waste receiver indicator 536 to alert a user that the fluid waste has reached a predetermined percentage of the capacity of the fluid receiver body 519. At this point, in one embodiment, the user has a certain predetermined time period to place the fluid receiver cap 518 on the fluid receiver body 519, which prepares the disposal assembly 510A for disposal.

In this embodiment, the specific type of fluid waste receiver sensor 582C can vary. In one embodiment, the fluid waste receiver sensor 582C can be a load cell. Alternatively, the fluid waste receiver sensor 582C can include one or more piezoelectric elements. Still alternatively, other types of sensors can be used that can transmit an electrical signal based on mechanical movement of the absorber retainer 572A.

In one embodiment, the fluid waste receiver sensor 582D can be a moisture-sensitive visual indicator that changes color (e.g., white to red) once the fluid level has risen to the level of the fluid waste receiver sensor 582D. For example, in one embodiment, the fluid waste receiver sensor 582D can be positioned at a specific level that, upon a color change of the fluid waste receiver sensor 582D, would indicate the fluid waste has reached a predetermined percentage of the capacity of the fluid receiver body 519. At this point, in one embodiment, the user would have a certain predetermined time period to place the fluid receiver cap 518 on the fluid receiver body 519, which prepares the disposal assembly 510A for disposal.

The timer activator 538 activates a timer within the controller 531. The positioning of the timer activator on or within the fluid waste receiver 512A can vary to suit the design requirements of the disposal assembly 510A and/or the fluid waste receiver 512A. In one embodiment, the timer activator 538 starts a timer, such as a clock as one non-exclusive example, that tracks the time until expiration of the fluid waste receiver 512A. The timer can be included as part of and/or embedded within the controller 531. Alternatively, the timer can be separate from the controller 531, and can be maintained either within the fluid waste receiver 512A or remotely, outside of the fluid waste receiver 512A. In certain alternative embodiments, the timer can be wirelessly connected or hardwired to the timer activator 538. In one embodiment, the timer activator 538 can be manually activated by the user once usage of the disposal assembly 510A has commenced, such as by manually depressing a button, flipping a switch, or by another suitable manual method. In an alternative embodiment, the timer activator 538 can be automatically activated by some specific initiating event, such as removal of the receiver lid 518, initial addition of fluid waste or other fluid within the fluid waste receiver 512A, or some other suitable initiating event.

In one embodiment, once a predetermined period of time has elapsed following activation of the timer activator 538, the controller 531 activates the fluid waste receiver indicator 536 or a separate timer indicator (not shown), which alerts the user that a specific time period has passed, and that the useful life of the disposal assembly 510A has either expired, or that expiration is scheduled to occur in a predetermined time period. For example, if expiration of the disposal assembly 510A occurs at 90 days from activation of the timer activator 538, the controller 531 may activate the fluid waste receiver indicator 536 at 75 days to provide a 15-day lead time for the user to terminate usage of the disposal assembly 510A. It is understood that the foregoing example is provided for ease of understanding only, and is not intended to limit in any manner the time periods for which the invention may be used.

Figure 5B:
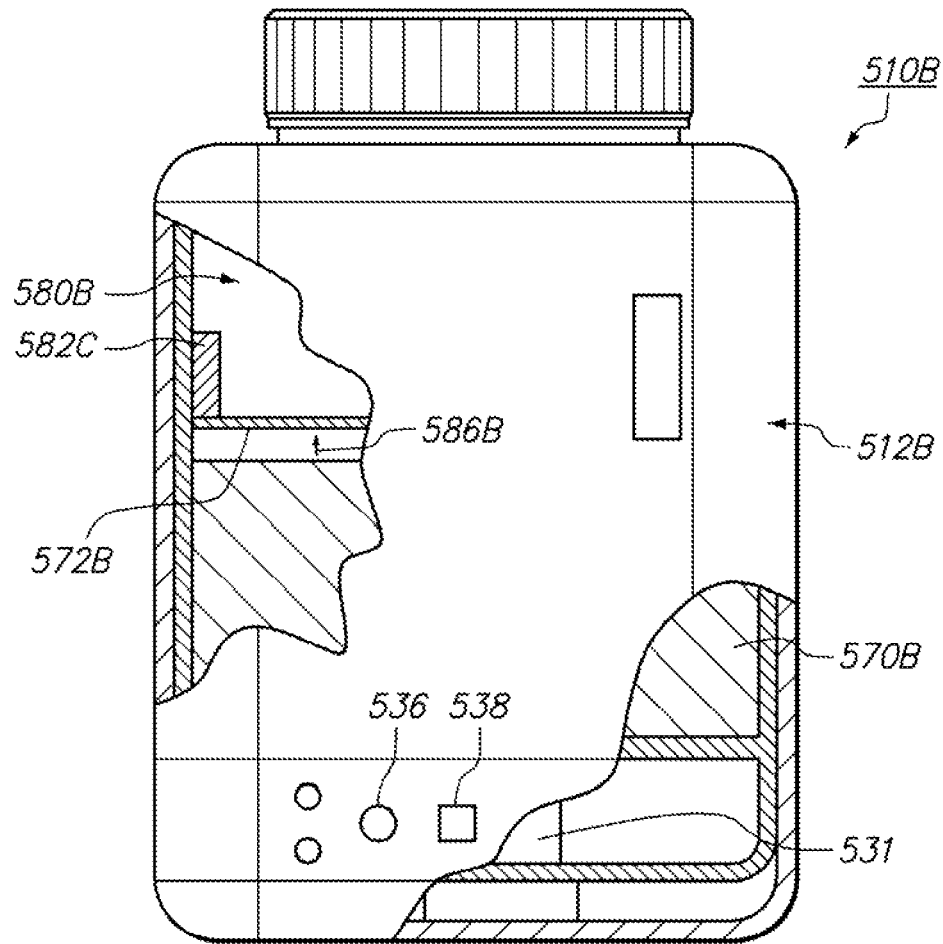
FIG. 5B is a partial cutaway view of yet another embodiment of the pharmaceutical waste disposal assembly.

FIG. 5B is a partial cutaway view of another embodiment of a disposal assembly 510B including a fluid waste receiver 512B. In this embodiment, the fluid waste receiver 512B is substantially similar to the fluid waste receiver 512A illustrated in FIG. 5A, except for certain modifications noted herein. So as not to obscure the features described relative to FIG. 5B, many of the features of the fluid waste receiver 512A illustrated in FIG. 5A have been omitted from FIG. 5B.

In the embodiment illustrated in FIG. 5B, the fluid waste receiver indicator 536 can be activated by the fluid waste receiver sensor 582C in a somewhat similar manner as that previously described. However, in this embodiment, the fluid absorber 570B is spaced apart a predetermined distance from the absorber retainer 572B to allow for a certain degree of expansion of the fluid absorber 570B as fluid waste is absorbed thereby. The specific distance that the absorber retainer 572B is spaced apart from the fluid absorber 570B can vary, but is dependent upon the specific expansion properties of the fluid absorber 570B.

Thus, once a particular amount of fluid waste has been introduced into the fluid absorber 570B, the fluid absorber 570B expands sufficiently toward the absorber retainer 572B so that the fluid absorber 570B eventually contacts the absorber retainer 572B. Therefore, in this embodiment, the fluid absorber 570B will move in an upward direction as indicated by arrow 586A as the fluid absorber 570B absorbs fluid waste. This upward movement generates a force against the fluid waste receiver sensor 582C, which in this embodiment is positioned in the gap region 580B. Once a predetermined force has been achieved, the fluid waste receiver sensor 582C transmits an electrical signal to the controller 531. The controller 531 then activates the fluid waste receiver indicator 536 to alert a user that the fluid waste has reached a predetermined percentage of the capacity of the fluid receiver body 519. At this point, in one embodiment, the user has a certain predetermined time period to place and/or lock the fluid receiver cap 518 on the fluid receiver body 519, which prepares the disposal assembly 510A for permanent disposal.

FIG. 6 is a perspective view of one embodiment of the solid waste receiver 614 including the solid receiver cap 620 and the solid receiver body 621. The specific configuration of the solid receiver body 621 of the solid waste receiver 614 can vary depending upon the design requirements of the disposal assembly 10. In the embodiment illustrated in FIG. 6, the solid receiver body 621 has a somewhat rectangular shape. Alternatively, the solid receiver body 621 can be conical, frustoconical, cubical, spherical, pyramidal, or can have any other suitable configuration.

FIG. 7 is a front elevation view of the solid waste receiver 614 illustrated in FIG. 6. In FIG. 7, the solid waste receiver 614 has curved, e.g., radiused, corners and edges.

FIG. 8 is a cross-sectional view of the solid waste receiver 614 taken on line 8-8 in FIG. 6, with the solid receiver cap 620 (illustrated in FIG. 6) removed for clarity. In the embodiment illustrated in FIG. 8, the solid waste receiver 614 can include one or more of a solid receiver body 621, a solid receiver guide 667, a fluid absorber 670, a reaction agent 687 and an adherer 688.

In one embodiment, the solid receiver guide 667 can include one or more solid waste diverters 658 that divert the direction of the solid waste while the solid waste is entering an interior of the solid waste receiver 614. In one embodiment, the solid waste diverters 658 can cause the solid waste to move in a back and forth or zigzag manner as the solid waste moves downward into the solid receiver body 621. In another embodiment, the solid waste diverter 658 can be in the shape of a spiral, e.g., similar to a snail shell, so that the solid waste spirals into the solid receiver body 621. Still alternatively, the one or more solid waste diverters 658 can have a different configuration. In certain embodiments, the solid waste diverters 658 can inhibit or prevent wrongful, illegal or unwanted removal of solid waste from inside solid receiver body 621 by inhibiting or impeding hands or other objects from entering the solid receiver body 621.

In one embodiment, the solid receiver guide 667 includes a guide flap 689 at or near the bottom of the solid receiver guide 667. In one such embodiment, the guide flap 689 is hinged so that the guide flap 689 can move between an open position and a closed position as indicated by arrow 690. In FIG. 8, the guide flap 689 is shown in the open position. In one embodiment, the guide flap 689 can include a flap weight 691 that maintains the guide flap 689 in the open position when the solid waste receiver 614 is in an upright position, such as that illustrated in FIG. 8. In the event the solid waste receiver 614 is moved to an inverted position, the flap weight 691 will cause the guide flap 689 to move to the closed position so that solid waste will be inhibited from exiting the solid receiver body 621. The solid receiver guide 667 can also include a flap stop 692 that inhibits movement of the guide flap 689 beyond the open position illustrated in FIG. 8.

The fluid absorber 670 can be included inside the solid receiver body 621 to absorb any fluid waste that may inadvertently be deposited into the solid receiver body 621 and/or that may be a by-product of the breakdown of any solid waste.

The reaction agent 687 can react with water or other fluids in order to chemically and/or physically break down any solid waste inside the solid receiver body 621, and/or make the solid waste undesirable and/or indigestible, once the solid receiver body 621 is determined to be ready for capping (i.e. at or near capacity, or at or near expiration). Stated another way, prior to capping the solid receiver body 621, a liquid is added to the solid receiver body 621, which catalyzes a reaction with the reaction agent 687 to destroy or otherwise chemically and/or physically change the solid waste to an unusable and/or unrecoverable form. Alternatively, a liquid is added that solidifies the reaction agent 687 to encapsulate or otherwise surround the solid waste in the solid receiver body 621. The solid receiver body 621 can then be capped, and is then ready for permanent disposal.

In one embodiment, the adherer 688 is positioned at least along a portion of the inside of the solid receiver body 621. The adherer 688 can be an adhesive material or any other suitable material that promotes adherence of the solid waste to the inside of the solid receiver body 621. The adherer 688 adds another layer of protection to inhibit solid waste from being removed from the solid receiver body 621.

Figure 9:
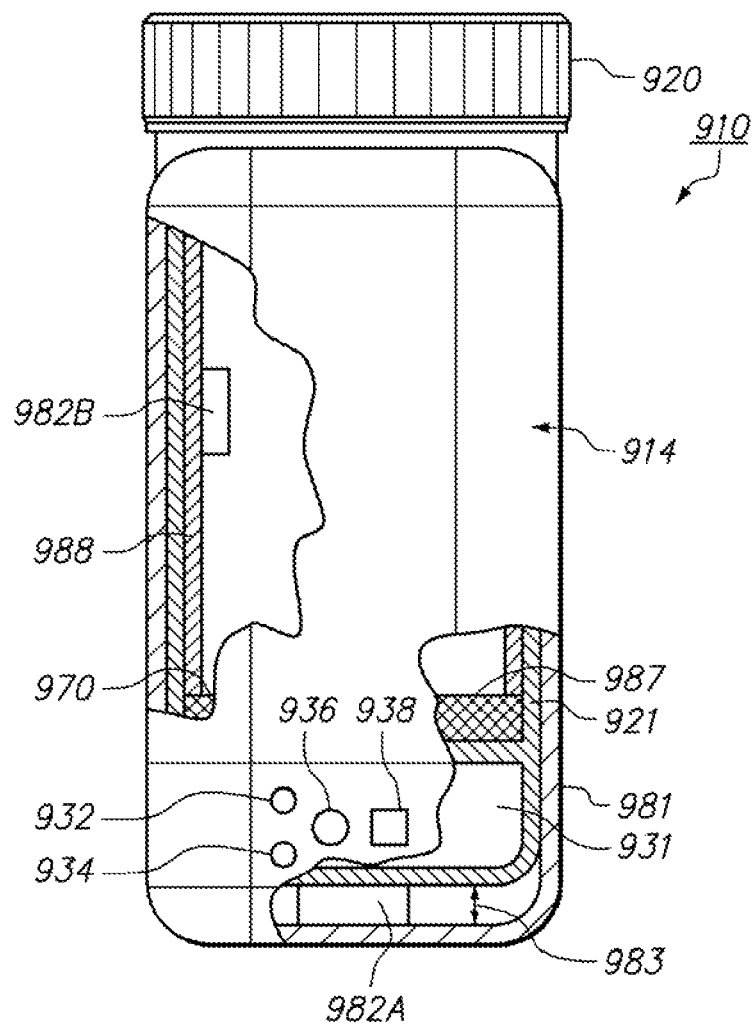
FIG. 9 is a partial cutaway view of yet another embodiment of the pharmaceutical waste disposal assembly.

FIG. 9 is a partial cutaway view of yet another embodiment of the disposal assembly 910. FIG. 9 is a partial cutaway view of another embodiment of a disposal assembly 910 including a solid waste receiver 914. In this embodiment, the solid waste receiver 914 is fully self-contained and is not used in conjunction with a separate receiver retainer (such as receiver retainer 16 illustrated in FIG. 1A). Although not necessarily illustrated in FIG. 9, the solid waste receiver 914 can include the same components illustrated and described relative to FIGS. 6 and 8, including the solid receiver guide 667, which functions substantially as described previously herein.

Additionally, in the embodiment illustrated in FIG. 9, the disposal assembly 910 includes a solid receiver cap 920, a solid receiver body 921, a controller 931, a charged battery indicator 932, a low battery indicator 934, a solid waste receiver indicator 936, a fluid absorber 970, a reaction agent 987 and an adherer 988, which function substantially as previously described herein, with the exception of certain modifications provided below. Further, the disposal assembly 910 can also include a timer activator 938, a solid receiver body retainer 981 and one or more solid waste receiver sensors 982A, 982B.

In one embodiment, the solid receiver body 921 is positioned within and is movable relative to the solid receiver body retainer 981 in a direction illustrated by arrow 983. Movement of the solid receiver body 921 relative to the solid receiver body retainer 981 only needs to be slight, and is dependent upon the weight of the contents of the solid receiver body 921, including any solid waste which may be present within the solid receiver body 921. In the embodiment illustrated in FIG. 9, a solid waste receiver sensor 982A is positioned between the solid receiver body 921 and the solid receiver body retainer 981. In one embodiment, the solid waste receiver sensor 982A is a weight sensor, such as a load cell, for example. In this embodiment, as the weight of the solid receiver body 921 and its contents increases, a greater force is exerted on the weight sensor 982A.

In one embodiment, the weight sensor 982A can convert a predetermined force into an electrical signal, which causes the solid waste receiver indicator 936 to activate. Activation of the solid waste receiver indicator 936 can alert a user that the solid waste has reached a predetermined percentage of the capacity of the solid receiver body 921, and the user has a certain predetermined time period to place the solid receiver cap 920 on the solid receiver body 921, which prepares the disposal assembly 910 for disposal. In various embodiments, the predetermined force required to activate the solid waste receiver indicator 936 and/or the predetermined percentage of the capacity of the solid receiver body 921 can be determined based upon various requirements of the specific regulations governing disposal of waste. Alternatively, the predetermined force required to activate the solid waste receiver indicator 936 and/or the predetermined percentage of the capacity of the solid receiver body 921 can be determined by the user, and can be programmed into the controller 931.

In another embodiment, the solid waste receiver indicator 936 can be activated by the solid waste receiver sensor 982B. In this embodiment, as the level of solid waste rises in the solid receiver body 921, the solid waste generates a force against the solid waste receiver sensor 982B. Once a predetermined force has been achieved, the solid waste receiver sensor 982B transmits an electrical signal to the controller 931. The controller 931 then activates the solid waste receiver indicator 936 to alert a user that the solid waste has reached a predetermined percentage of the capacity of the solid receiver body 921. At this point, in one embodiment, the user has a certain predetermined time period to place the solid receiver cap 920 on the solid receiver body 921, which prepares the disposal assembly 910 for permanent disposal.

In this embodiment, the specific type of solid waste receiver sensor 982B can vary. In one embodiment, the solid waste receiver sensor 982B can be a load cell. Alternatively, the solid waste receiver sensor 982B can include one or more piezoelectric elements. Still alternatively, other types of sensors can be used that can transmit an electrical signal based on mechanical movement of the solid waste receiver sensor 982B caused by pressure or force exerted by the rising level of solid waste in the solid receiver body 921.

In certain embodiments, the timer activator 938 can manually be activated by the user once usage of the disposal assembly 910 has commenced. In one embodiment, the timer activator 938 notifies the controller 931 to start a clock or other timekeeping device. Once a predetermined period of time has elapsed, the controller 931 can activate the solid waste receiver indicator 936, which alerts the user that a specific time period has passed, and that the useful life of the disposal assembly 910 has either expired, or that expiration is imminent or within a predetermined time period of expiration. For example, if expiration of the disposal assembly 910 occurs at 90 days from activation of the timer activator, the controller 931 may activate the solid waste receiver indicator 936 at 75 days to provide a 15-day lead time for the user to terminate usage of the disposal assembly 910. It is understood that the foregoing example is provided for ease of understanding only, and is not intended to limit in any manner the time periods for which the invention may be used.

Figure 10:
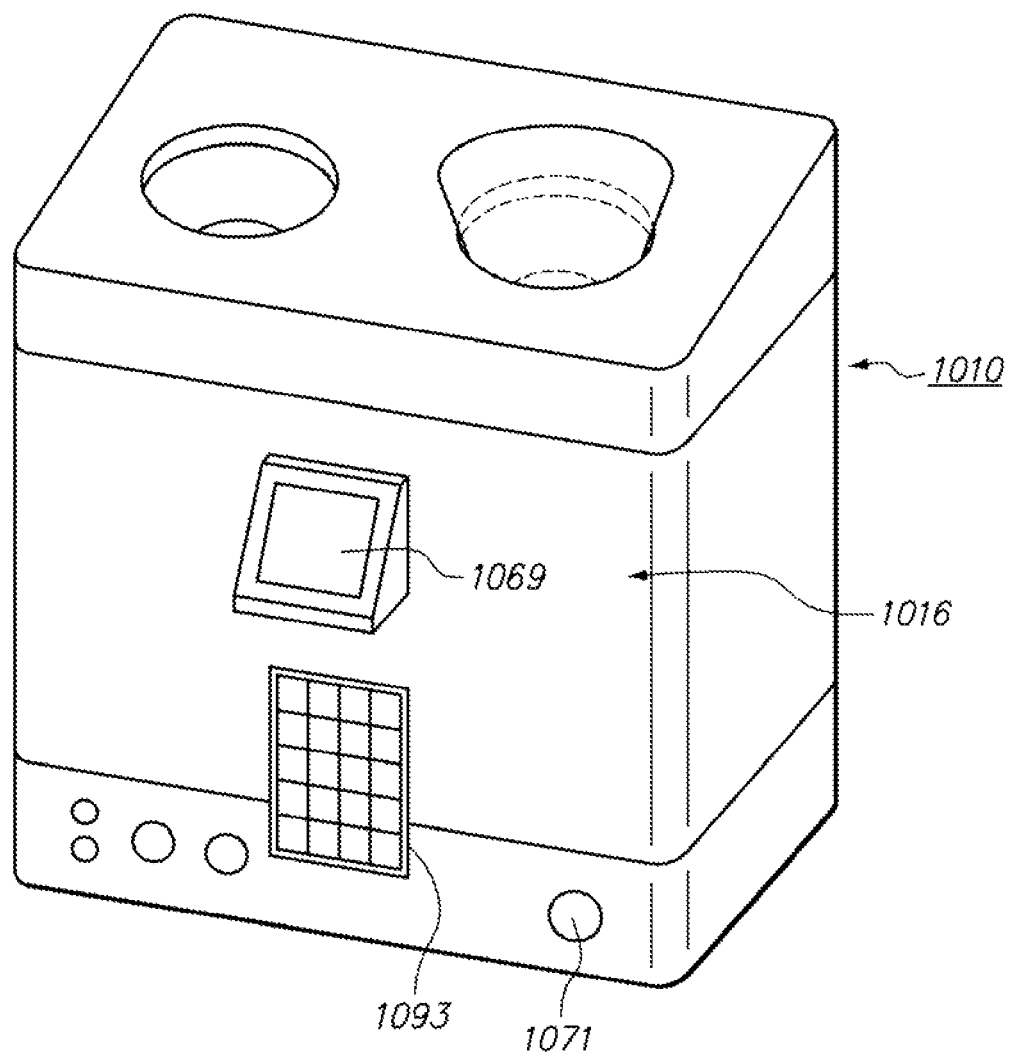
FIG. 10 is a front perspective view of one embodiment of the receiver retainer.

FIG. 10 is a front perspective view of one embodiment of a disposal assembly 1010, including a receiver retainer 1016. Although not necessarily illustrated in FIG. 10, the disposal assembly 1010 can include some or all of the same features illustrated and described previously herein. In the embodiment illustrated in FIG. 10, the receiver retainer 1016 includes an input device 1093, such as a keypad or a touch-screen as non-exclusive examples. The input device 1093 is utilized by a user to input certain relevant information, such as drug classification (as one non-exclusive example), that can be communicated to the controller 31 (illustrated in FIG. 1C, for example) for further processing. Additionally, or alternatively, the input device 1093 can be used to identify and/or authenticate a user for access to the disposal assembly 1010. In one embodiment, the user can type a passcode or other authentication information into the input device 1093. Alternatively, other types of authentication methods can be included, such as a badge scanner or barcode reader, as non-exclusive alternative examples. The design of the input device 1093 can be varied to suit the design requirements of the disposal assembly 1010. In one embodiment, the input device 1093 can receive, store and/or transmit, information regarding the type of waste that is being deposited into the disposal assembly 1010.

Additionally, or in the alternative, the disposal assembly 1010 can include an output device 1069 that can display certain relevant information to the user. By way of example and not by way of limitation, the output device 1069 can display information such as current fill level(s) of the waste receivers, expiration dates of the waste receivers, time remaining prior to expiration, the types of waste that have previously been deposited into the waste receivers, user input information, drug classifications, remaining battery life, alert information, and any other relevant information that could possibly be utilized by a user of the disposal assembly 1010.

In the embodiment illustrated in FIG. 10, the disposal assembly 1010 also includes a monitoring device 1071. In this embodiment, the monitoring device 1071 can include a video and/or audio recorder, such as a video camera or a sound recorder, as non-exclusive examples. The monitoring device 1071 can be utilized to monitor and/or record video and/or audio of the usage of the disposal assembly 1010 by the user(s). A real-time and/or previously recorded video and/or audio feed can be stored in the disposal assembly 1010, such as in a memory of the controller (not illustrated in FIG. 10), for example, or in some other location within the disposal assembly 1010. Alternatively, the video and/or audio feed can be transmitted to another location not within the disposal assembly, such as a separate monitor or screen (not shown), a video recording device (not shown), or any other suitable location for storage and/or viewing of the recorded video data.

Figure 11A:
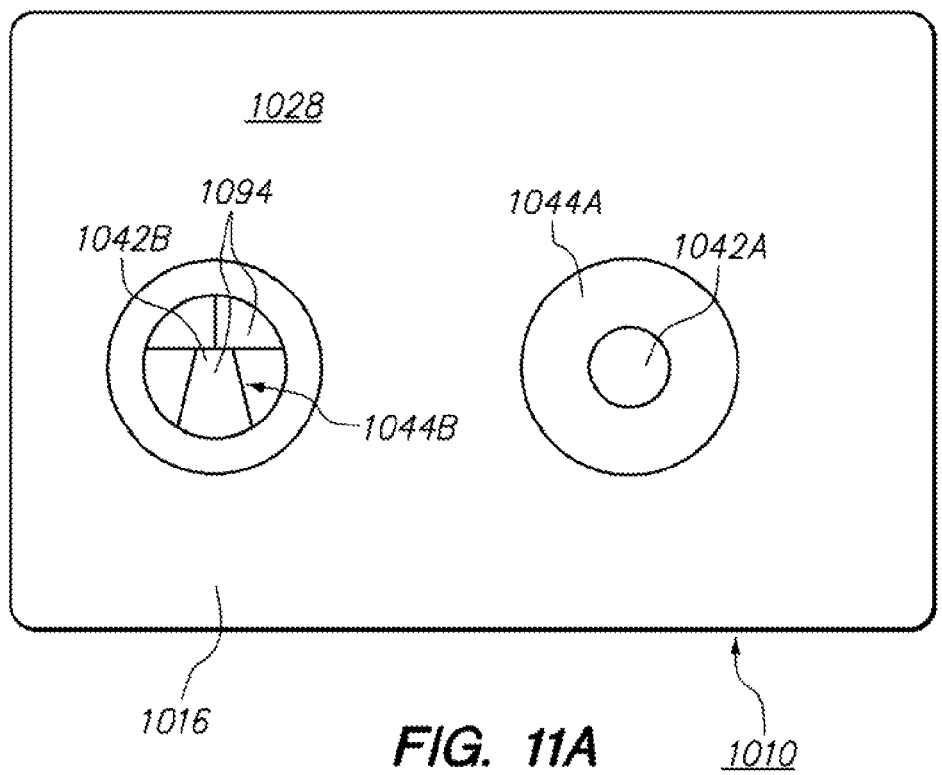
FIG. 11A is a simplified top view of the pharmaceutical waste disposal assembly, including the receiver retainer shown in FIG. 10, illustrated in the closed position.

FIG. 11A is a simplified top view of the disposal assembly 1010, including the receiver retainer 1016 illustrated in FIG. 10, with the input device 1093 omitted. In this embodiment, the receiver retainer 1016 is shown in the closed position. In one embodiment, the receiver retainer 1016 includes a retainer lid 1028 having one or more lid apertures (a fluid lid aperture 1042A and a solid lid aperture 1042B are illustrated in FIG. 11A). The lid apertures 1042A, 1042B function substantially in the same manner as those previously described herein, allowing fluid waste and/or solid waste to be deposited into one of the waste receivers (not shown in FIG. 11A) from outside of the receiver retainer 1016. In this embodiment, the lid apertures 1042A, 1042B are positioned in, and extend through, the retainer lid 1028.

In the embodiment illustrated in FIG. 11A, the fluid lid aperture 1042A includes a fluid waste guide 1044A, and the solid lid aperture 1042B includes a solid waste guide 1044B. Each waste guide 1044A, 1044B assists in directing the specific phase of waste (solid, liquid or gas) to the appropriate waste receiver. In this embodiment, the fluid waste guide 1044A includes a funnel-type device. Further, the solid waste guide 1044B includes a funnel-type device in combination with one or more diverters 1094 that guide or otherwise direct the waste to the appropriate waste receiver, in a manner substantially similar or identical to that previously described herein. It is understood that either of the lid apertures 1042A, 1042B can include any type of waste guide 1044A, 1044B, and that the specific combinations of lid apertures 1042A, 1042B and waste guides 1044A, 1044B illustrated in FIG. 11A are provided for ease of understanding only, and are not intended to be limiting in any manner.

Figure 11B:
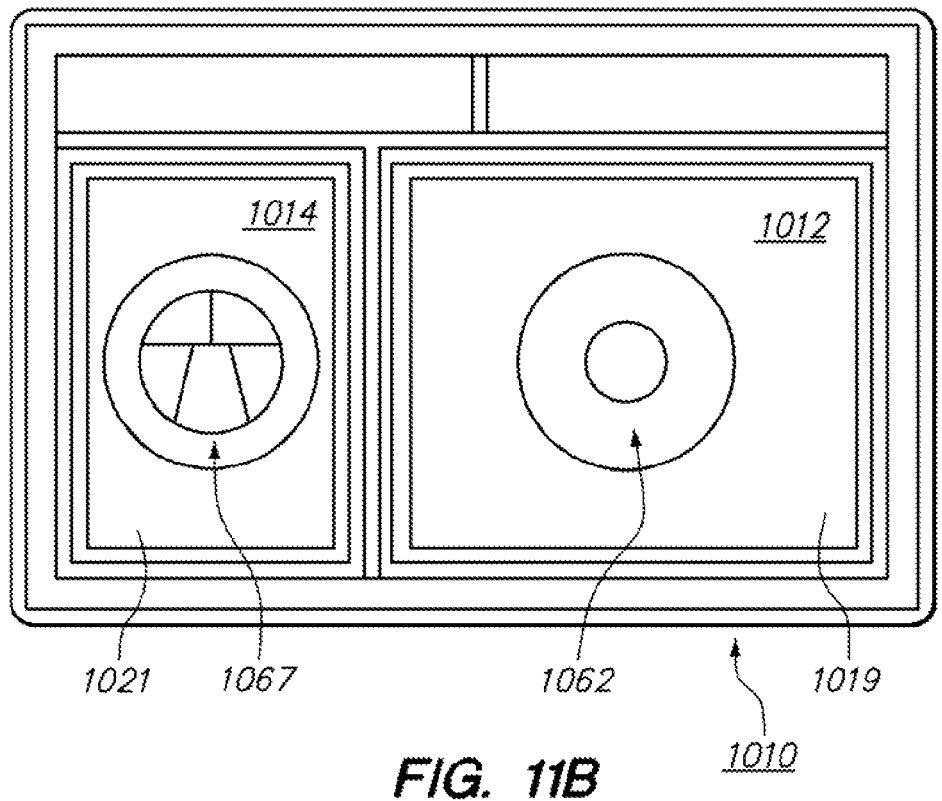
FIG. 11B is a simplified top view of a portion of one embodiment of the pharmaceutical waste disposal assembly illustrated in FIG. 10, illustrated in the open position.

FIG. 11B is a simplified top view of a portion of the disposal assembly 1010 illustrated in FIG. 10, illustrated in the open position, with the retainer lid 1028 and the input device 1093 removed for clarity. In this embodiment, the disposal assembly 1010 includes the fluid waste receiver 1012 and the solid waste receiver 1014. The fluid waste receiver 1012 includes a fluid receiver guide 1062 that guides the fluid waste into the fluid receiver body 1019. The fluid receiver guide 1062 can include a standard funnel-type device (as illustrated in FIG. 11B) a spiral funnel, or a series of diverters.

In this embodiment, the solid waste receiver 1014 includes a solid receiver guide 1067 that guides the solid waste into the solid receiver body 1021. The solid receiver guide 1067 can include a standard funnel-type device, a spiral funnel, or a series of diverters (as illustrated in FIG. 11B).

When the disposal assembly 1010 illustrated in FIG. 11B is combined with the retainer lid 1028 illustrated in FIG. 11A, both a corresponding waste guide 1044A, 1044B and a corresponding receiver guide 1062, 1067 serve to guide the specific phase of waste into the appropriate receiver body 1019, 1021. With this design, the likelihood of improper removal of waste from the receiver bodies 1019, 1021 is decreased.

Figure 12:
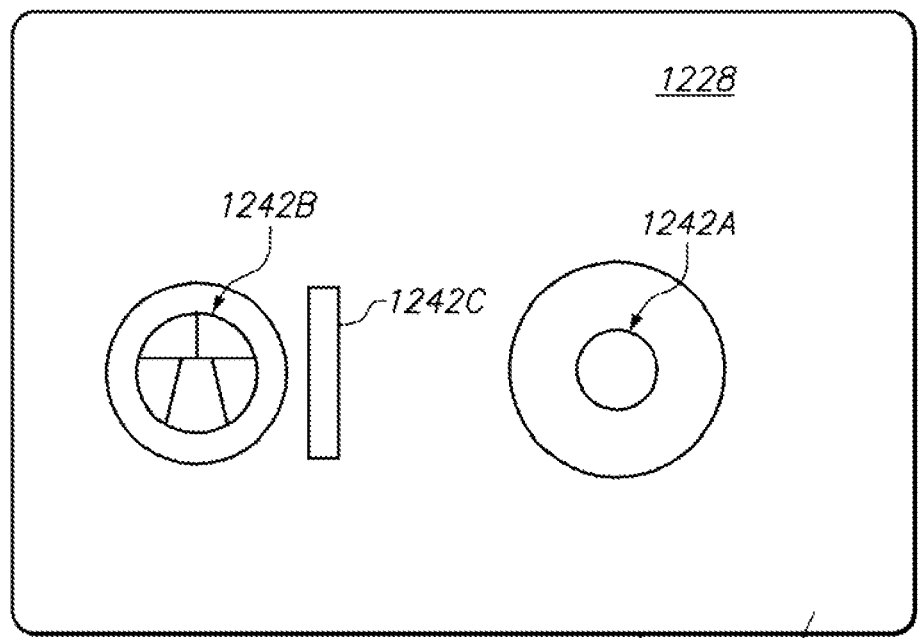
FIG. 12 is a simplified top view of another embodiment of the pharmaceutical waste disposal assembly including the receiver retainer, illustrated in the closed position.

FIG. 12 is a simplified top view of another embodiment of the disposal assembly 1210 including the receiver retainer 1216, illustrated in the closed position. In this embodiment, the receiver retainer 1216 includes a retainer lid 1228 that is substantially similar to the retainer lid 1028 illustrated and described relative to FIG. 11A, with certain noted exceptions. In the embodiment illustrated in FIG. 12, in addition to a fluid lid aperture 1242A, the receiver retainer 1216 also includes a first solid lid aperture 1242B and a second solid lid aperture 1242C. The first solid lid aperture 1242B is substantially similar to the solid lid aperture 1042B illustrated and described relative to FIG. 11A.

The second solid lid aperture 1242C is designed to receive solid waste in the form of pharmaceutical and/or medical patches and the like. The size and configuration of the second solid lid aperture 1242C can vary. In one embodiment, the second solid lid aperture 1242C can have a somewhat rectangular, slot-like configuration. Alternatively, the second solid lid aperture 1242C can have another suitable configuration that is consistent with accepting pharmaceutical and/or medical patches. The solid waste that is deposited into the second solid lid aperture 1242C can be received by the same solid waste receiver (not illustrated in FIG. 12) that receives solid waste via the first solid lid aperture 1242B. Alternatively, the solid waste that is deposited into the second solid lid aperture 1242C can be received by a different solid waste receiver than the solid waste receiver that receives solid waste via the first solid lid aperture 1242B.

Figure 13:
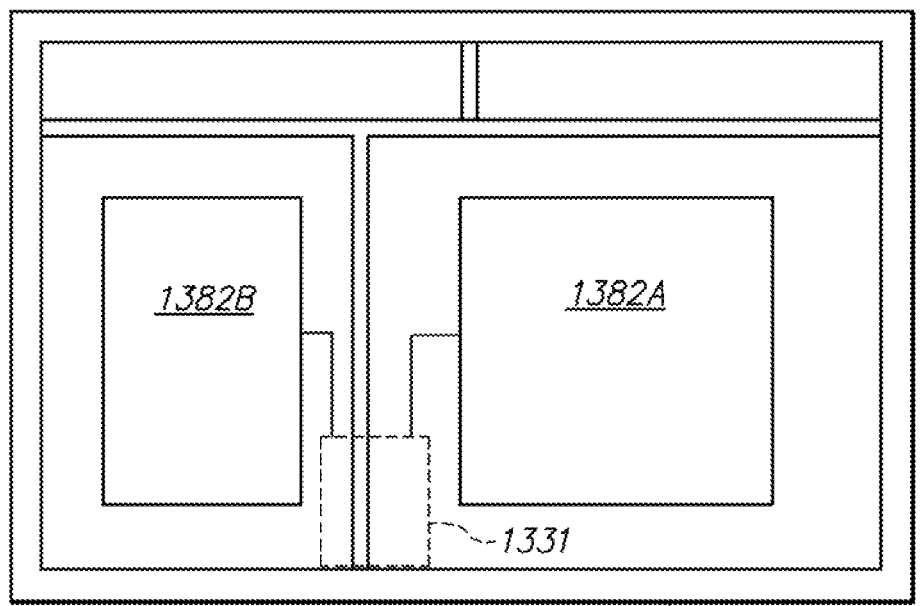
FIG. 13 is a simplified top view of one embodiment of a portion of the receiver retainer, illustrated in the open position.

FIG. 13 is a simplified top view of one embodiment of a portion of a receiver retainer 1316, illustrated in the open position, with the retainer lid omitted for clarity. In this embodiment, the receiver retainer 1316 includes a controller 1331 (illustrated in phantom), a fluid waste receiver sensor 1382A and a solid waste receiver sensor 1382B. In one embodiment, the waste receiver sensors 1382A, 1382B are weight sensors, such as a load cell, for example, and function in a substantially similar or identical manner as those previously described herein. In this embodiment, once the weight of the contents of one or both of the receiver bodies (not shown in FIG. 13) increases to a predetermined level, the weight sensor 1382A, 1382B will send an electrical signal to the controller 1331, which can then activate the appropriate waste receiver indicator 36, 38 (illustrated in FIG. 1A, for example), as necessary.

Figure 14:
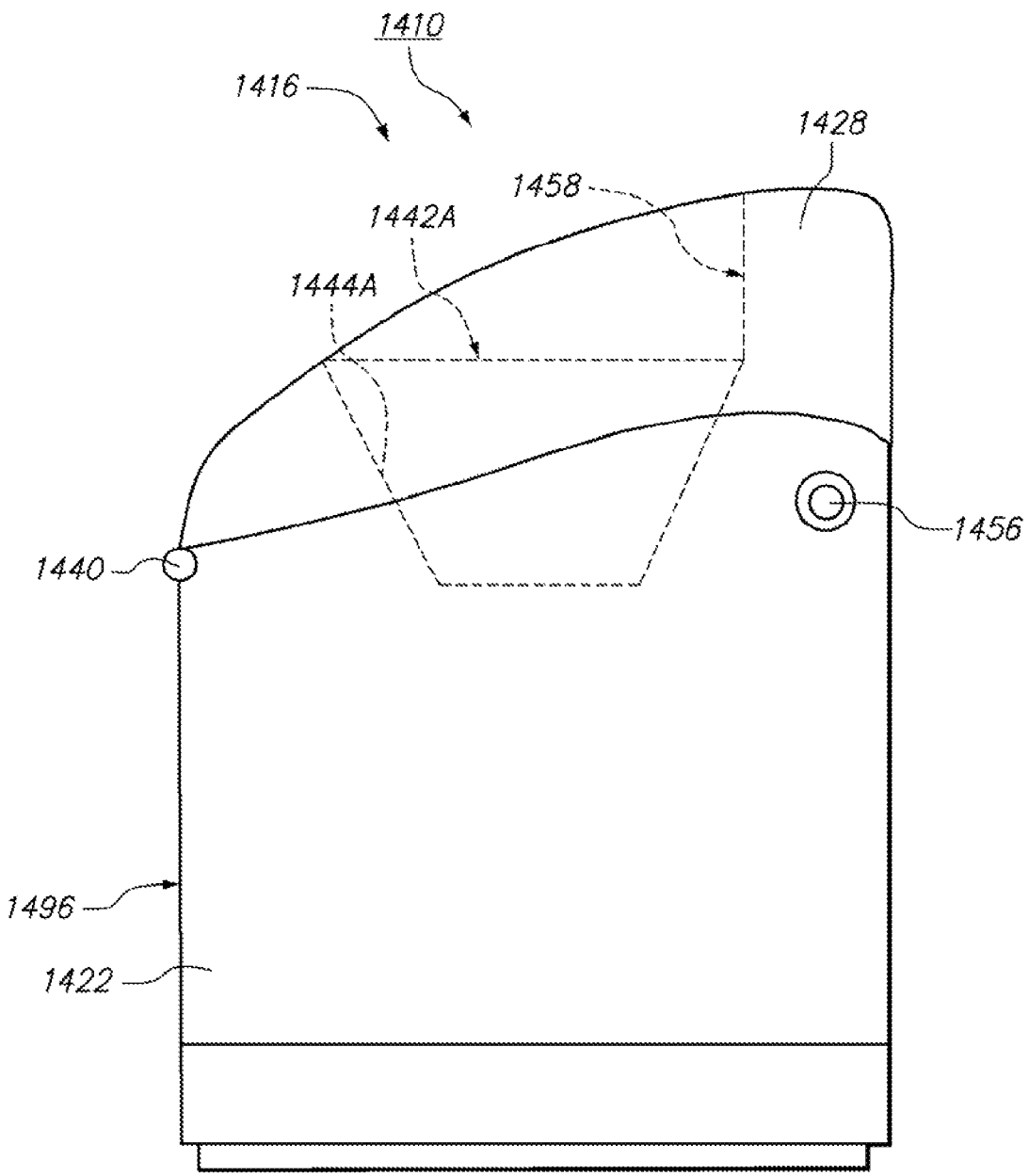
FIG. 14 is a side elevation of another embodiment of the receiver retainer.

FIG. 14 is a side elevation of another embodiment of a receiver retainer 1416. In this embodiment, the configuration of the retainer lid 1428 is such that a fluid waste diverter 1458 (illustrated in phantom) is built directly into the retainer lid 1428 so that a separate fluid waste diverter is unnecessary. The fluid waste diverter 1458 diverts and/or directs fluid waste to the fluid lid aperture 1442A (illustrated in phantom) and the fluid waste guide 1444A (illustrated in phantom).

Additionally, in this embodiment, the retainer lid 1428 is movably secured to the retainer housing 1422 by one or more hinges 1440. In this embodiment, the one or more hinges 1440 are secured to a retainer front 1496 so that in the event the disposal assembly 1410 is backed up against a wall or other surface, opening of the retainer lid 1428 will not be impeded.

In the embodiment illustrated in FIG. 14, the receiver retainer 1416 also includes a locking mechanism 1456 for locking the retainer lid 1428 in a closed position, as illustrated in FIG. 14. The locking mechanism 1456 can include any suitable type of locking mechanism known to those skilled in the art, including but not limited to a combination lock or a lock requiring one or more of a key, passcode, fingerprint reader, voice recognition, or any other suitable type of lock.

Figure 15:
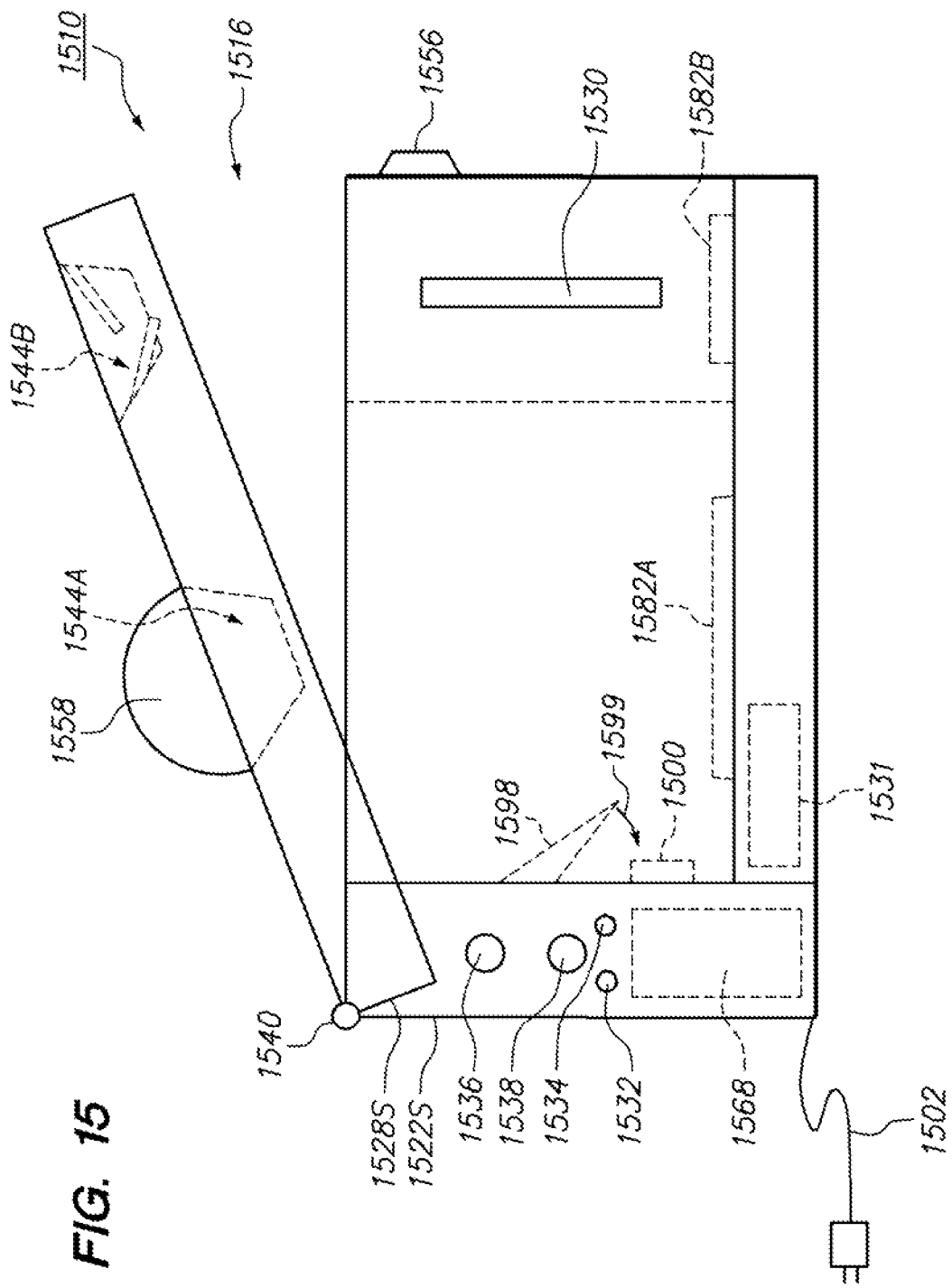
FIG. 15 is a front elevation of yet another embodiment of the receiver retainer, with various internal components illustrated in phantom.

FIG. 15 is a front elevation of yet another embodiment of a receiver retainer 1516, illustrated in an open position. The receiver retainer 1516 can include various features previously described herein, although not specifically illustrated in FIG. 15. Additionally, the receiver retainer 1516 can include one or more viewing windows 1530, a controller 1531, a charged battery indicator 1532, a low battery indicator 1534, a fluid waste receiver indicator 1536, a solid waste receiver indicator 1538, one or more hinges 1540, a fluid waste guide 1544A, a solid waste guide 1544B, a locking mechanism 1556, a fluid waste diverter 1558, an electrochemical cell structure 1568, and one or more waste receiver sensors 1582A, 1582B, each of which function substantially as previously described herein, with the exception of certain modifications noted herein. Further, the receiver retainer 1516 can also include a timer activator 1598, an identification reader 1500, and an AC power supply cord 1502.

In this embodiment, the hinges 1540 are secured to a housing side panel 1522S and a lid side panel 1528S so that the retainer lid 1528 opens to one side, as illustrated in FIG. 15. With this design, the retainer lid 1528 of the receiver retainer 1516 will not be impeded and can still be opened even when the receiver retainer 1516 is backed against a wall or is mounted to a wall, for example.

In one embodiment, at any time that the retainer lid 1528 is in the open position, an audible and/or visual indicator or alert is activated. With this design, users can be notified in the event of unauthorized (or authorized) access to the interior of the receiver retainer 1516 occurs.

In the embodiment illustrated in FIG. 15, the timer activator 1598 operates substantially similarly to the timer activator 538 illustrated in FIG. 5, except the timer activator 1598 in FIG. 15 is automatically activated when a waste receiver (not shown in FIG. 15) is initially placed into the receiver retainer 1516. In one embodiment, the timer activator 1598 is moved by the waste receiver in a direction as indicated by arrow 1599 when the waste receiver is placed into the receiver retainer 1516. When the timer activator 1598 is activated, the timer activator 1598 notifies the controller 1531 to start a clock or other timekeeping device. Once a predetermined period of time has elapsed, the controller 1531 can activate the fluid waste receiver indicator 1536, which alerts the user that a specific time period has passed, and that the useful life of the disposal assembly 1510 has either expired, or that expiration is imminent or within a predetermined time period of expiration.

The identification reader 1500 can detect and/or read an identification tag 200 (illustrated in FIG. 2, for example) positioned on one or more waste receivers (not shown in FIG. 15). Although only one identification reader 1500 is illustrated in FIG. 15, it is understood that additional identification readers can be positioned in different locations on or within the receiver retainer 1510. For example, the identification reader 1500 illustrated in FIG. 15 is positioned to read an identification tag that is positioned on a fluid waste receiver. However, the identification reader 1500 can equally be positioned in another location for reading an identification tag positioned on a solid waste receiver, for example.

In one embodiment, the identification reader 1500 can read an RFID tag, an integrated circuit, a barcode label, or any other suitable type of identifying tag that is included in either or both the fluid waste receiver and the solid waste receiver (not shown in FIG. 15). The identification reader 1500 can serve one or more purposes. In one embodiment, the identification reader 1500 can transmit a signal to the controller 1531 to activate a clock or other timer once the fluid waste receiver and/or solid waste receiver are properly positioned within the receiver retainer 1516. As provided hereinabove, the timer can be used to determine when the waste receiver is expired or will soon expire as of a predetermined number of hours, days, etc. from the time the clock is activated. Data from the identification reader 1500 can be transmitted to and/or stored within the controller 1531.

In another embodiment, the identification reader 1500 can alternatively, or in addition, store information from the identification tag on the waste receiver so that a particular waste receiver cannot be used twice. For example, the identification reader 1500 can read unique information from a specific identification tag, and store this information in the controller 1531 or in memory outside of the receiver retainer 1516. Once the waste receiver is removed from the receiver retainer 1516, if the same waste receiver is ever placed back into the receiver retainer 1516, the identification reader 1500, in conjunction with the controller 1531, will recognize the waste receiver as being the same waste receiver that was previously utilized with the receiver retainer 1516. In one embodiment, the appropriate receiver indicator 1536, 1538 will be activated to alert a user of the reuse of the waste receiver.

In another embodiment, the identification reader 1500 can alternatively, or in addition, store information from the identification tag on the waste receiver in a centralized database that can be accessed by others to track location, shipment or delivery of the waste receiver to a permanent disposal site, to locations within a hospital or other health care facility, or another suitable locations.

The AC power supply cord 1502 can be used to transmit AC power to the disposal assembly 1510 to charge the electrochemical cell structure 1568, or to power the entire disposal assembly 1510 in embodiments that do not include a electrochemical cell structure 1568, or in the event the electrochemical cell structure 1568 is low or dead.

Figure 16:
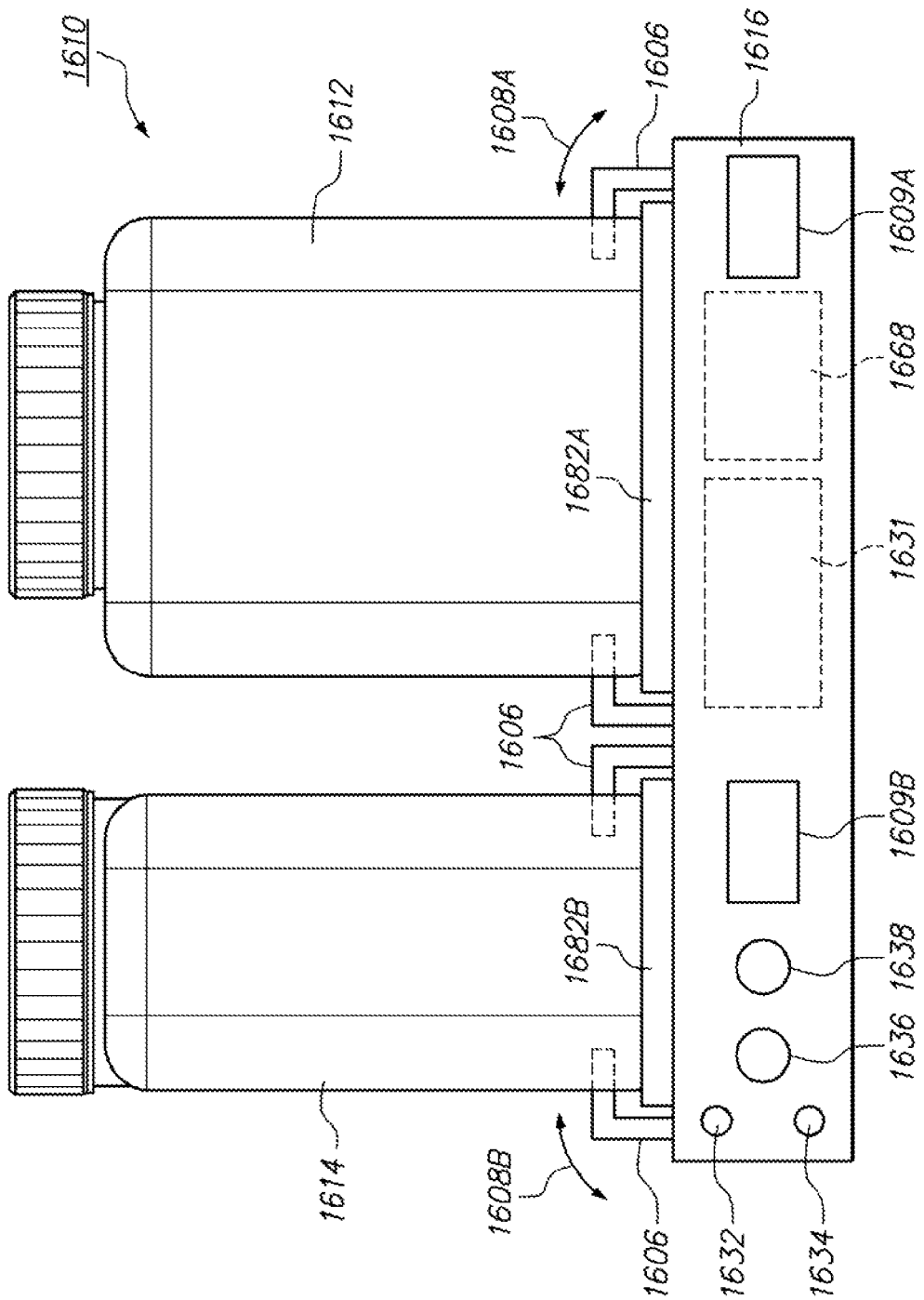
FIG. 16 is a front elevation of yet another embodiment of a pharmaceutical waste disposal assembly having features of the present invention.

FIG. 16 is a front elevation of yet another embodiment of a disposal assembly 1610. In this embodiment, the disposal assembly 1610 includes one or both of a fluid waste receiver 1612 and a solid waste receiver 1614. Further, the disposal assembly 1610 includes a receiver retainer 1616. In this embodiment, the receiver retainer 1616 has a platform configuration. The receiver retainer 1616 can include various features previously described herein, although not specifically illustrated in FIG. 16. Additionally, the receiver retainer 1616 can include a controller 1631 (illustrated in phantom), a charged battery indicator 1632, a low battery indicator 1634, a fluid waste receiver indicator 1636, a solid waste receiver indicator 1638, an electrochemical cell structure 1668, and one or more waste receiver sensors 1682A, 1682B, each of which function substantially as previously described herein, with the exception of certain modifications noted herein. Further, the receiver retainer 1616 can also include one or more receiver securers 1606 (shown partially in phantom where inserted into waste receivers 1612, 1614), a fluid digital readout 1609A and/or a solid digital readout 1609B.

The waste receivers 1612, 1614 are positioned on the receiver retainer 1616, and are held in place by the receiver securers 1606. The receiver securers 1606 can be movably positioned to secure the waste receivers 1612, 1614 to the receiver retainer 1616. In one embodiment, the receiver securers 1606 can be manually moved into place to secure the waste receivers 1612, 1614 to the receiver retainer 1616. Alternatively, the receiver securers 1606 can automatically move into place to secure the waste receivers 1612, 1614 to the receiver retainer 1616. In one such embodiment, the receiver securers 1606 can electromechanically move toward and/or away from the waste receivers 1612, 1614 in the direction of arrows 1608A, 1608B. In an alternative embodiment, the receiver securers 1606 can move toward and/or away from the waste receivers 1612, 1614 by another suitable means.

The digital readouts 1609A, 1609B can provide specific information regarding the status of the waste receivers 1612, 1614. For example, in certain embodiments, the digital readouts 1609A, 1609B can indicate one or more of the length of time the waste receivers 1612, 1614 have been positioned on the receiver retainer 1616, the weight of the waste receivers 1612, 1614, the weight of the contents of the waste receivers 1612, 1614, the expiration date for each of the waste receivers 1612, 1614 based on when they were positioned on the receiver retainer 1616, or any other useful information depending upon the design requirements of the disposal assembly 1610.

Figure 17A:
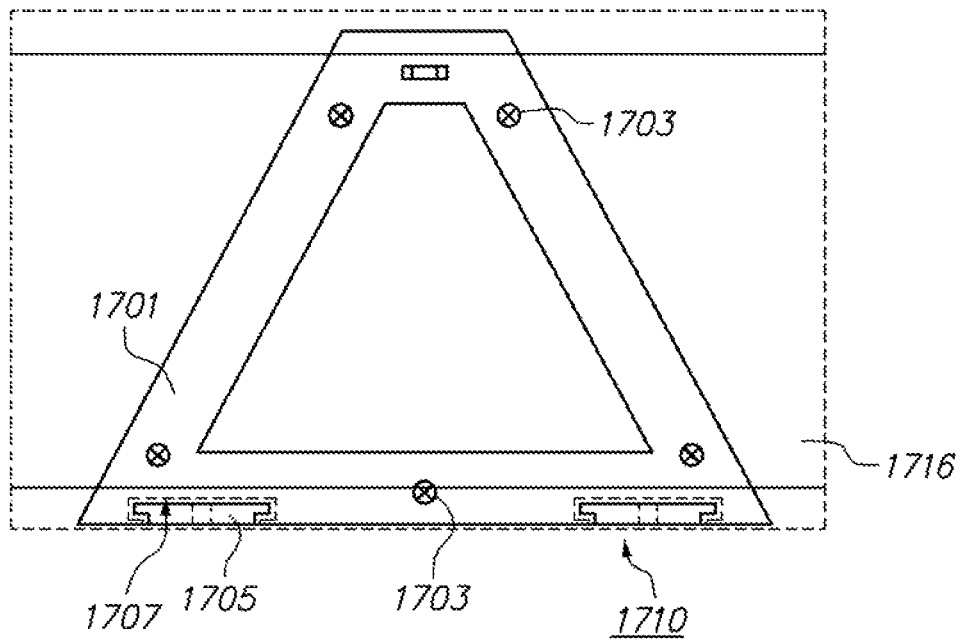
FIG. 17A is a front view of one embodiment of the pharmaceutical waste disposal assembly including a mounting apparatus, and a simplified representation of the receiver retainer (illustrated in phantom) engaged with the mounting apparatus.

FIG. 17A is a front view of one embodiment of the disposal assembly 1710 including a mounting apparatus 1701, and a simplified representation of the receiver retainer 1716 (illustrated in phantom) engaged with the mounting apparatus 1701. In this embodiment, the mounting apparatus 1701 can be secured to a vertical or non-vertical surface with one or more fasteners 1703, such as screws, nails, etc. The specific configuration of the mounting apparatus 1701 can vary. In one embodiment, the mounting apparatus 1701 can have a somewhat triangular configuration. However, in alternative embodiments, the mounting apparatus 1701 can have a square, curved, circular, elliptical, polygonal or another suitable configuration.

In this embodiment, the mounting apparatus 1701 includes one or more support rails 1705 (two support rails are illustrated in FIG. 17A) that support the receiver retainer 1716. The support rails 1705 slidingly interlock with corresponding complementary rail receivers 1707 on the receiver retainer 1716. As provided in greater detail herein, the receiver retainer 1716 can slide onto the support rails 1705, and then be lockingly secured to the mounting apparatus 1701 for stability and security.

Figure 17B:
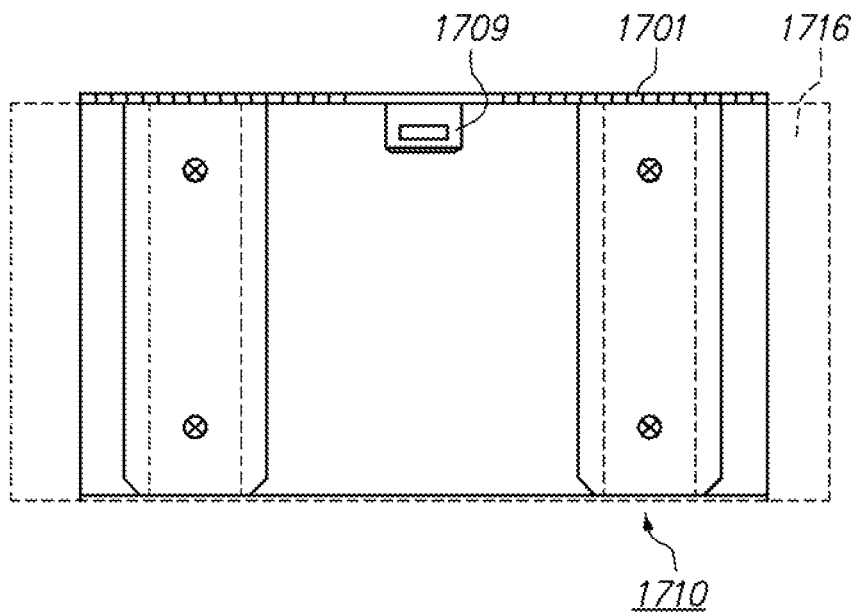
FIG. 17B is a top view of the mounting apparatus illustrated in FIG. 17A.

FIG. 17B is a top view of the disposal assembly 1710 including the mounting apparatus 1701 illustrated in FIG. 17A, and the receiver retainer 1716 illustrated in phantom for differentiation. In this embodiment, the mounting apparatus 1701 includes a locking tab 1709 that extends into the receiver retainer 1716 as provided in greater detail herein.

Figure 17C:
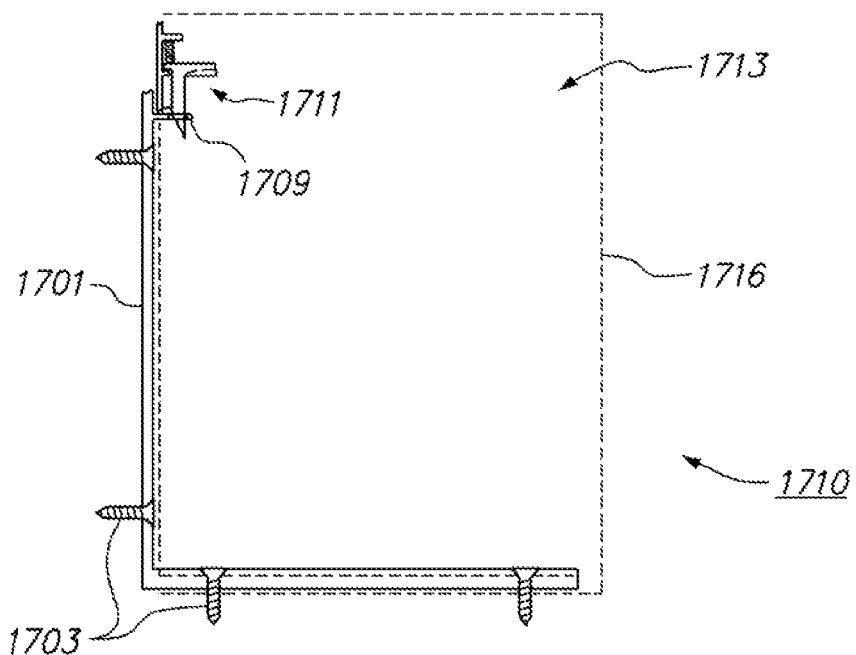
FIG. 17C is a side elevation of the mounting apparatus illustrated in FIG. 17A, and one simplified embodiment of the receiver retainer (illustrated in phantom) engaged with the mounting apparatus.

FIG. 17C is a side elevation of disposal assembly 1710 including the mounting apparatus 1701 illustrated in FIG. 17A, and the receiver retainer 1716 (illustrated in phantom) engaged with the mounting apparatus 1701. In this embodiment, it is evident that the mounting apparatus 1701 can be secured with fasteners 1703 to one or both of two surfaces that are substantially perpendicular to one another. Further, in this embodiment, the receiver retainer 1716 includes a locking pin assembly 1711 that is positioned in a retainer interior 1713 of the receiver retainer 1716. The locking pin assembly 1711 lockingly engages the locking tab 1709 of the mounting apparatus 1701 to secure the receiver retainer 1716 to the mounting apparatus 1701. In certain embodiments of the receiver retainer 1716 that include a locking mechanism (as previously described herein), the locking pin assembly 1711 cannot be unlocked from the locking tab 1709 unless the receiver retainer 1716 can be opened to access the locking pin assembly 1711. With this design, unauthorized persons will be inhibited from disengaging the receiver retainer 1716 from the mounting apparatus 1701.

Figure 17D:
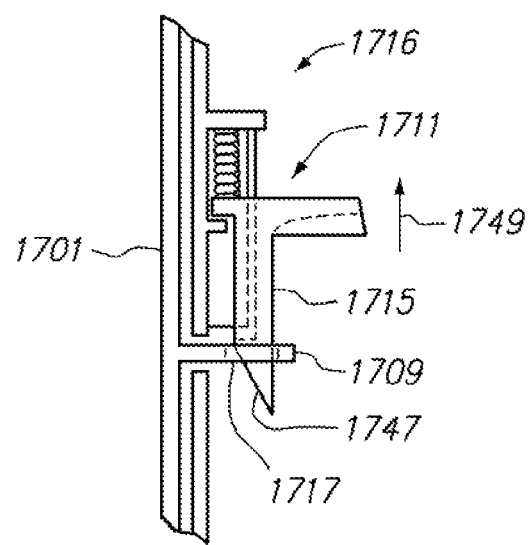
FIG. 17D is a detailed side view of a portion of the mounting apparatus engaged with a portion of the receiver retainer.

FIG. 17D is a detailed side view of a portion of the mounting apparatus 1701 including the locking tab 1709, and a portion of the receiver retainer 1716, including the locking pin assembly 1711, illustrated in an engaged position. In this embodiment, the locking pin assembly 1711 is spring loaded so that a locking pin 1715 is biased to extend through a tab aperture 1717 in the locking tab 1709. The locking pin 1715 can have an angled tip 1747 to allow the locking pin 1715 to enter the tab aperture 1717 without the need to manually lift the locking pin 1715 in an upwardly direction (indicated by arrow 1749). However, to remove the locking pin 1715 from the tab aperture 1717, it is necessary to manually lift the locking pin 1715 in the upwardly direction 1749, which in one embodiment, can only be accomplished from the retainer interior 1713 (illustrated in FIG. 17C).

Figure 18A:
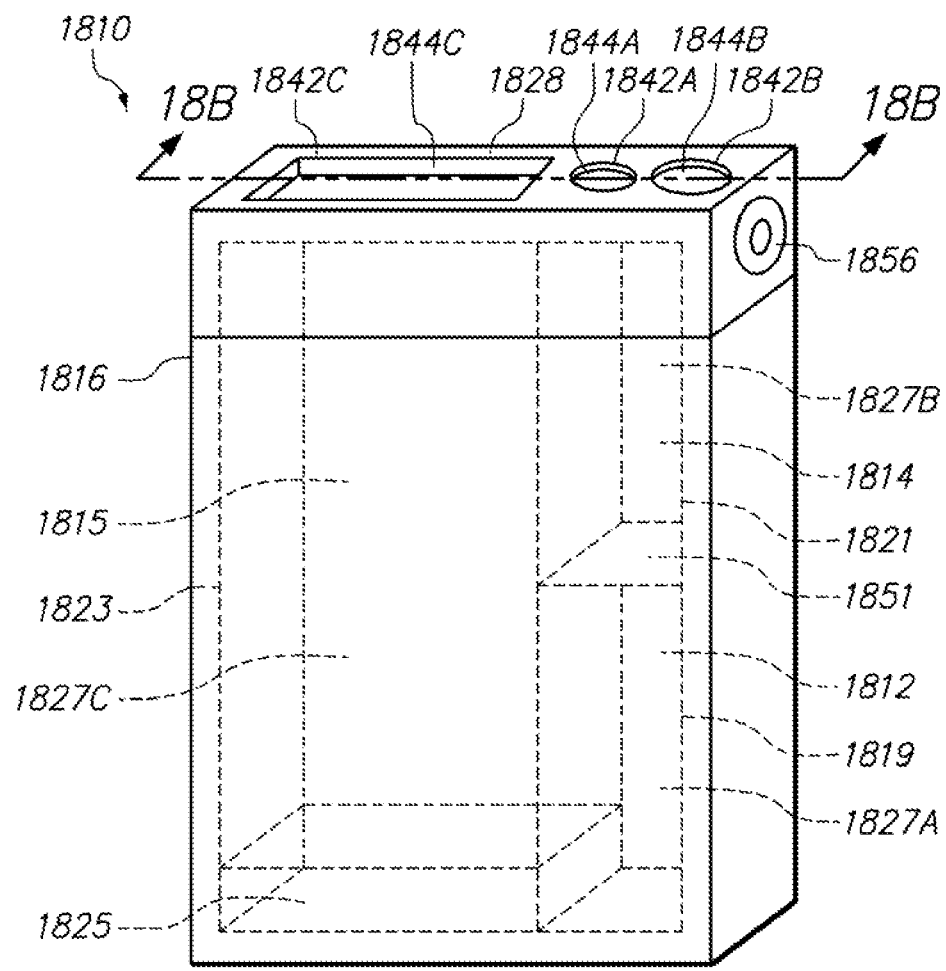
FIG. 18A is a front perspective view of still another embodiment of a pharmaceutical waste disposal assembly having features of the present invention, including a receiver assembly.

FIG. 18A is a front perspective view of still another embodiment of a pharmaceutical waste disposal assembly 1810 having features of the present invention. In this embodiment, the pharmaceutical waste disposal assembly 1810 includes a receiver assembly 1851 including a fluid waste receiver 1812 (illustrated in phantom), a solid waste receiver 1814 (illustrated in phantom), a sharps receiver 1815 (illustrated in phantom), a receiver retainer 1816, and an absorption pad 1825 (illustrated in phantom). It should be noted that either the fluid waste receiver 1812 or the solid waste receiver 1814 can be referred to generically herein as a "waste receiver". In one non-exclusive alternative embodiment, the absorption pad 1825 can be omitted from the pharmaceutical waste disposal assembly 1810.

The receiver retainer 1816 is adapted to receive and selectively retain the fluid waste receiver 1812, the solid waste receiver 1814 and the sharps receiver 1815. In certain non-exclusive alternative embodiments, the pharmaceutical waste disposal assembly 1810 can omit either the fluid waste receiver 1812 or the solid waste receiver 1814. In such embodiments, the receiver retainer 1816 can receive and selectively retain the sharps receiver 1815 and one or the other of the fluid waste receiver 1812 and the solid waste receiver 1814.

In the embodiment illustrated in FIG. 18A, the fluid waste receiver 1812 includes a fluid receiver body 1819 (illustrated in phantom), the solid waste receiver 1814 includes a solid receiver body 1821 (illustrated in phantom), and the sharps receiver 1815 includes a sharps receiver body 1823 (illustrated in phantom). It should be noted that either the fluid receiver body 1819 or the solid receiver body 1821 can be referred to generically herein as a "waste receiver body". In certain embodiments, the fluid receiver body 1819 and/or the solid receiver body 1821 can individually or both be positioned adjacent to the sharps receiver body 1823 within the receiver retainer 1816.

Moreover, in various embodiments, each of the fluid receiver body 1819, the solid receiver body 1821 and the sharps receiver body 1823 define regions, i.e. a fluid waste region 1827A, a solid waste region 1827B and a sharps region 1827C, respectively, that are separate and independent from one another. Stated another way, the waste contents that are placed within one region 1827A, 1827B, 1827C do not intermingle with the waste contents that are placed within any of the other regions 1827A, 1827B, 1827C. It should be noted that either the fluid waste region 1827A or the solid waste region 1827B can be referred to generically herein as a "waste region".

As illustrated in FIG. 18A, the volume of the fluid waste region 1827A can be somewhat similar to the volume of the solid waste region 1827B. Alternatively, the volume of the fluid waste region 1827A can be precisely the same as the volume of the solid waste region 1827B or the volume of the fluid waste region 1827A can be different than the volume of the solid waste region 1827B. In certain non-exclusive examples, the volume of the fluid waste region 1827A can be approximately 25 percent, 50 percent, 75 percent, 100 percent, 150 percent or 200 percent larger or smaller than the volume of the solid waste region 1827B.

Further, as illustrated in FIG. 18A, the volume of the sharps region 1827C is larger than each of the fluid waste region 1827A and the solid waste region 1827B. Alternatively, the volume of the sharps region 1827C can be smaller than or approximately the same as the volume of one or more of the fluid waste region 1827A and the solid waste region 1827B.

Additionally, in this embodiment, the solid receiver body 1821 is positioned substantially directly above the fluid receiver body 1819. Alternatively, the fluid receiver body 1819, the solid receiver body 1821 and the sharps receiver body 1823 can have a different orientation relative to one another within the retainer receiver 1816. For example, in one non-exclusive alternative embodiment, the fluid receiver body 1819 can be positioned substantially directly above the solid receiver body 1821 and/or the sharps receiver body 1823. It is recognized that the foregoing examples are provided for ease of understanding only, and are not intended to limit the various configurations and relative positioning of the receiver bodies 1819, 1821, 1823, in any manner.

Further, in certain embodiments, one or more of the fluid waste receiver 1812, the solid waste receiver 1814 and the sharps receiver 1815 can be formed together as an integrated unit. Stated another way, one or more of the fluid waste receiver 1812, the solid waste receiver 1814 and the sharps receiver 1815 can be formed as a unitary structure. In such embodiments, one or more of the fluid waste receiver 1812, the solid waste receiver 1814 and the sharps receiver 1815 can be inserted into and/or removed from the receiver retainer 1816 together as an integrated unit. For example, in one embodiment, the fluid waste receiver 1812 and the sharps receiver 1815 are formed together as an integrated unit and can be inserted into and/or removed from the receiver retainer 1816 simultaneously as a unitary structure. In another alternative embodiment, all three of the of the fluid waste receiver 1812, the solid waste receiver 1814 and the sharps receiver 1815 can be formed together as an integrated unit and can be inserted into and/or removed from the receiver retainer 1816 together as an integrated unit. As used herein, the terms "integrated unit" and "unitary structure" do not necessary require the receivers 1812, 1814, 1815, to be permanently fused or formed from a single piece of material, although they may be so formed. For example, in one embodiment, two or more of the receivers 1812, 1814, 1815, may be formed separately, and connected, secured or otherwise attached to one another so that they do not substantially move relative to one another.

Although not necessarily illustrated in FIG. 18A, the fluid waste receiver 1812 can include some or all of the same components illustrated and described relative to FIGS. 2, 4A and 4B, including for example, one or more of the fluid receiver guide 262, the fluid distributor 264, the fluid processor 274 and the fluid deodorizer 276, which function substantially as described previously herein.

Additionally, although not necessarily illustrated in FIG. 18A, the solid waste receiver 1814 can include some or all of the same components illustrated and described relative to FIG. 8, including for example, one or more of the solid receiver guide 667, the fluid absorber 670, the reaction agent 687, and the adherer 688, which function substantially as described previously herein.

Further, the receiver retainer 1816 can include various features previously described herein, although not specifically illustrated in FIG. 18A. For example, the receiver retainer 1816 can include a controller, a charged battery indicator, a low battery indicator, a fluid waste receiver indicator, a solid waste receiver indicator, an electrochemical cell structure, a timer activator, and one or more waste receiver sensors, each of which function substantially as previously described herein.

As shown in FIG. 18A, the absorption pad 1825 can be positioned substantially at a bottom and/or along an interior of the sharps receiver 1815. In one embodiment, the absorption pad 1825 can be included within the sharps receiver 1815 to absorb any fluid waste that may inadvertently be deposited into the sharps receiver 1815 along with the sharps. For example, when the fluid waste within a syringe is emptied into the fluid waste receiver 1812 prior to the syringe being placed into the sharps receiver 1815, all of the fluid waste may not necessarily be fully drained from within the syringe. In this instance, any remaining fluid waste that is present within the syringe can be absorbed by the absorption pad 1825 when and if the fluid waste drains out of the syringe when the syringe is positioned within the sharps retainer body 1823.

As illustrated in this embodiment, the receiver retainer 1816 includes a retainer lid 1828 that includes a fluid lid aperture 1842A, a solid lid aperture 1842B and a sharps lid aperture 1842C. The fluid lid aperture 1842A allows fluid pharmaceutical waste to be deposited into the fluid waste receiver 1812 from outside of the receiver retainer 1816. The solid lid aperture 1842B allows solid pharmaceutical waste to be deposited into the solid waste receiver 1814 from outside of the receiver retainer 1816. The sharps lid aperture 1842C allows sharps waste to be deposited into the sharps receiver 1815 from outside of the receiver retainer 1816. In this embodiment, the lid apertures 1842A, 1842B, 1842C and positioned within and/or extend through the retainer lid 1828.

In the embodiment illustrated in FIG. 18A, the fluid lid aperture 1842A includes a fluid waste guide 1844A, the solid lid aperture 1842B includes a solid waste guide 1844B, and the sharps lid aperture 1842C includes a sharps waste guide 1844C. It should be noted that either the fluid waste guide 1844A or the solid waste guide 1844B can be referred to generically herein as a "raw waste guide". As illustrated, the waste guides 1844A, 1844B, 1844C can each be positioned substantially within and/or extend through the retainer lid 1828. Each waste guide 1844A, 1844B, 1844C assists in directing the specific waste (liquid, solid or sharps) to the appropriate waste receiver 1812, 1814, 1815, in a manner substantially similar or identical to that previously described herein.

In the embodiment illustrated in FIG. 18A, the receiver retainer 1816 also includes a locking mechanism 1856 for locking the retainer lid 1828 in a closed position, as illustrated in FIG. 18A. The locking mechanism 1856 can include any suitable type of locking mechanism known to those skilled in the art, including but not limited to a combination lock or a lock requiring one or more of a key, passcode, fingerprint reader, voice recognition, or any other suitable type of lock.

Figure 18B:
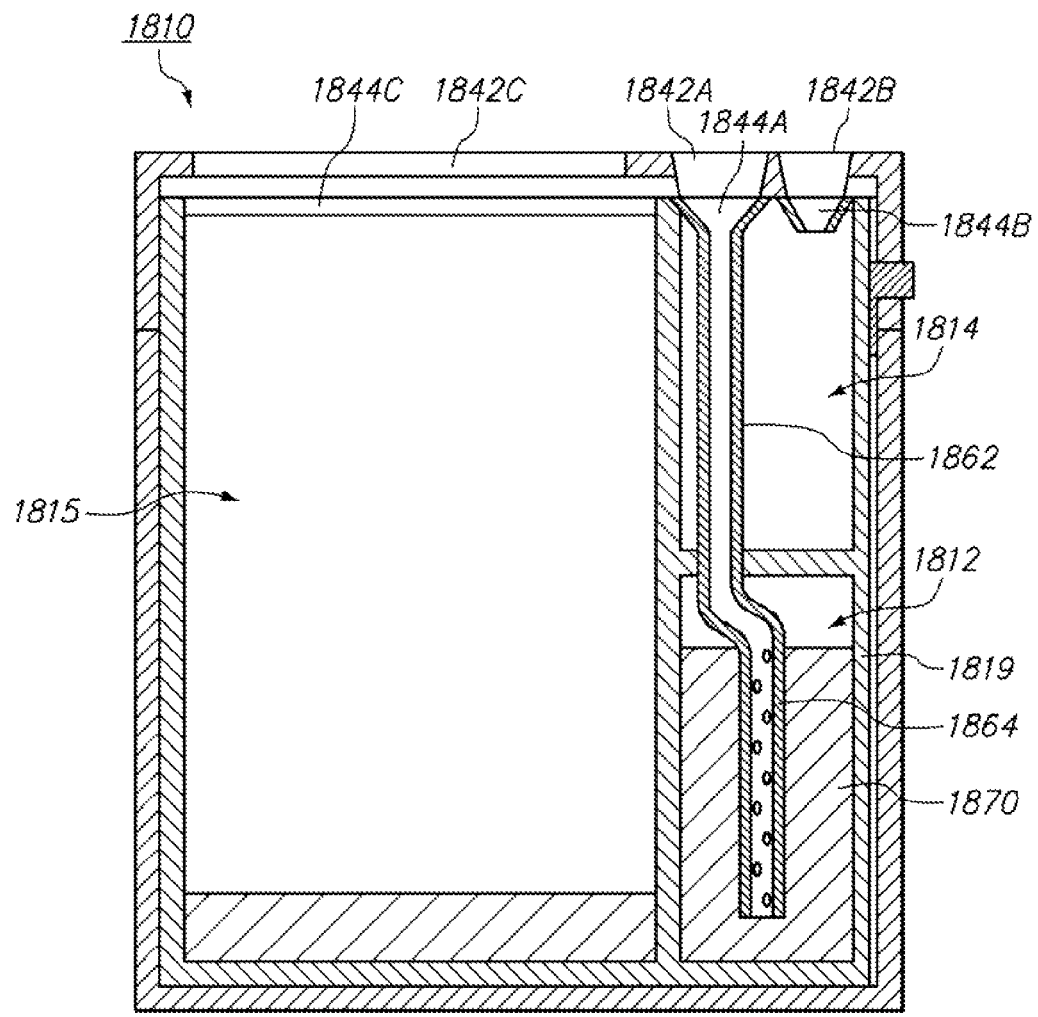
FIG. 18B is a cross-sectional view of the pharmaceutical waste disposal assembly taken on line B-B in FIG. 18A.

FIG. 18B is a cross-sectional view of the pharmaceutical waste disposal assembly 1810 illustrated in FIG. 18A taken along line B-B. As illustrated, the fluid waste guide 1844A can include a standard funnel-type device that guides the fluid waste into the fluid waste receiver 1812. In certain non-exclusive alternative embodiments, the fluid waste guide 1844A can include a spiral funnel, and/or a series of diverters. Further, as illustrated in FIG. 18B, the solid waste guide 1844B can include a standard funnel-type device that guides the solid waste into the solid waste receiver 1814. In certain non-exclusive alternative embodiments, the solid waste guide 1844B can include a spiral funnel, and/or a series of diverters. It is understood that either of the lid apertures 1842A, 1842B can include any type of waste guide 1844A, 1844B, and that the specific combinations of lid apertures 1842A, 1842B and waste guides 1844A, 1844B illustrated in FIG. 18B are provided for ease of understanding only, and are not intended to be limiting in any manner.

Additionally, as shown in this embodiment, the sharps waste guide 1844C guides the sharps into the sharps receiver 1815. In certain non-exclusive alternative embodiments, the sharps waste guide 1844C can include a one-way mail slot-type of guide. As used herein, a "one-way" guide is any guide that inhibits sharps from exiting the sharps receiver 1815 once the sharps have been inserted into the sharps receiver 1815. In non-exclusive alternative embodiments, the sharps waste guide 1844C can include a trap door-type of guide, or any other one-way door or slot known to those skilled in the art. Still alternatively, the sharps waste guide 1844C can include an opening with no one-way device. It is understood that the sharps lid aperture 1842C can include any type of sharps waste guide 1844C, and that the specific combination of sharps lid aperture 1842C and sharps waste guide 1844C illustrated in FIG. 18B is provided for ease of understanding only, and is not intended to be limiting in any manner. With the designs provided herein, the likelihood of improper removal of waste from any of the fluid waste receiver 1812, the solid waste receiver 1814, and the sharps receiver 1815, is decreased.

Further, as illustrated in FIG. 18B, the fluid waste receiver 1812 can further include a fluid receiver guide 1862, a fluid distributor 1864 and a fluid absorber 1870. The fluid receiver guide 1862 is substantially similar or identical to the fluid receiver guide 62 previously described herein. In particular, the fluid receiver guide 1862 guides the fluid waste into the fluid receiver body 1819.

Additionally, the fluid distributor 1864 can be substantially similar to and/or can include one or more of the features of any of the embodiments illustrated and described in detail above in FIGS. 4A-4K. In the embodiment illustrated in FIG. 18A, the fluid distributor 1864 receives fluid waste via the fluid receiver guide 1862 and can directly distribute and/or allow the fluid waste to flow to one or more levels of the fluid absorber 1870 in a more even (e.g., non-random) manner. With this design, the fluid waste can more rapidly be absorbed by the fluid absorber 1870, which inhibits puddling or ponding of fluid waste within the fluid waste receiver 1812.

Figure 18C:
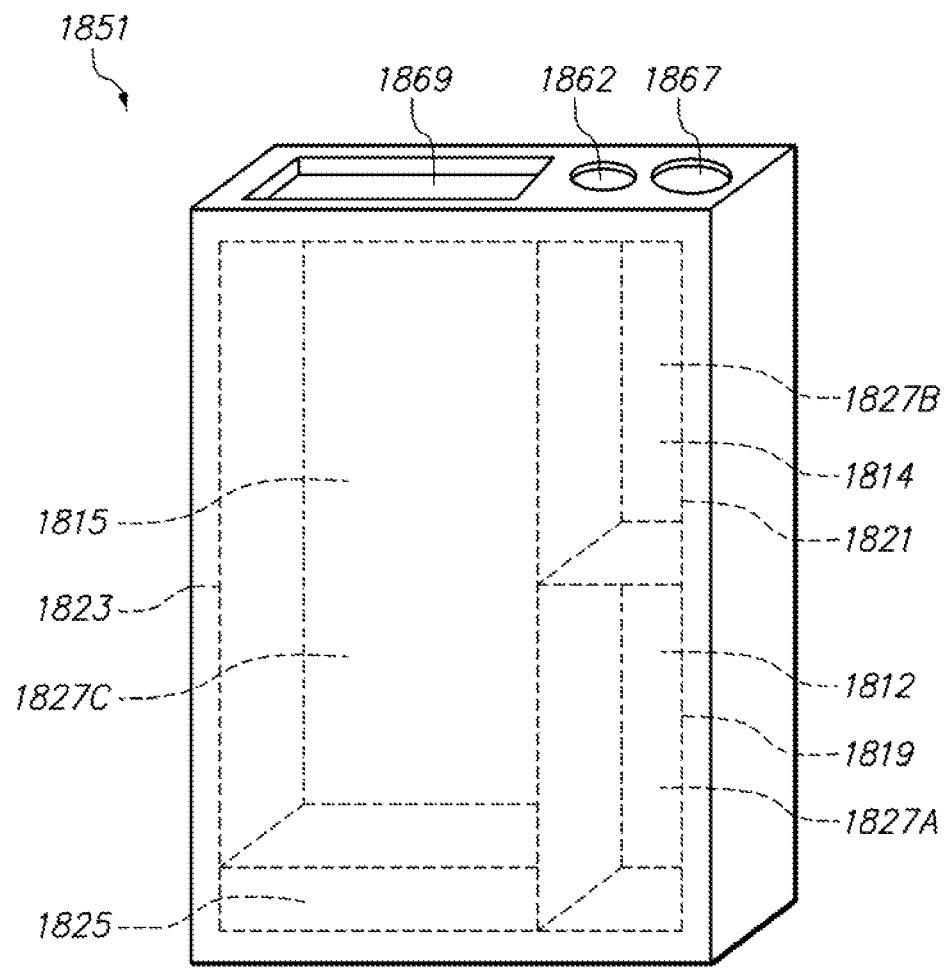
FIG. 18C is a front perspective view of one embodiment of the receiver assembly.

FIG. 18C is a front perspective view of one embodiment of the receiver assembly 1851 illustrated in FIG. 18A, with the receiver retainer omitted for clarity. In this embodiment, the receiver assembly 1851 includes the fluid waste receiver 1812, the solid waste receiver 1814, the sharps receiver 1815 and the absorption pad 1825.

As illustrated in FIG. 18C, the fluid waste receiver 1812 includes the fluid receiver body 1819 that defines the fluid waste region 1827A, and a fluid receiver guide 1862 that guides the fluid waste into the fluid receiver body 1819. The size, shape and positioning of the fluid receiver guide 1862 can be varied to suit the design requirements of the pharmaceutical waste disposal assembly 1810 (illustrated in FIG. 18A) and the receiver retainer 1816 (illustrated in FIG. 18A). In this embodiment, the fluid receiver guide 1862 is positioned to substantially coincide with the fluid lid aperture 1842A (illustrated in FIG. 18A) and the fluid waste guide 1844A (illustrated in FIG. 18A). Stated another way, fluid waste that is directed through the fluid lid aperture 1842A and the fluid waste guide 1844A is further directed into the fluid receiver guide 1862 before being guided into and retained within the fluid receiver body 1819.

Additionally, as illustrated in FIG. 18C, the solid waste receiver 1814 includes the solid receiver body 1821 that defines the solid waste region 1827B, and a solid receiver guide 1867 that guides the solid waste into the solid receiver body 1821. The size, shape and positioning of the solid receiver guide 1867 can be varied to suit the design requirements of the pharmaceutical waste disposal assembly 1810 and the receiver retainer 1816. In this embodiment, the solid receiver guide 1867 is positioned to substantially coincide with the solid lid aperture 1842B (illustrated in FIG. 18A) and the solid waste guide 1844B (illustrated in FIG. 18A). Stated another way, solid waste that is directed through the solid lid aperture 1842B and the solid waste guide 1844B is further directed into the solid receiver guide 1867 before being guided into and retained within the solid receiver body 1821.

Further, as illustrated in FIG. 18C, the sharps receiver 1815 includes the sharps receiver body 1823 that defines the sharps region 1827C, and a sharps receiver guide 1869 that guides the sharps into the sharps receiver body 1823. The size, shape and positioning of the sharps receiver guide 1869 can be varied to suit the design requirements of the pharmaceutical waste disposal assembly 1810 and the receiver retainer 1816. In this embodiment, the sharps receiver guide 1869 is positioned to substantially coincide with the sharps lid aperture 1842C (illustrated in FIG. 18A) and the sharps waste guide 1844C (illustrated in FIG. 18A). Stated another way, sharps that are directed through the sharps lid aperture 1842C and the sharps waste guide 1844C are further directed into the sharps receiver guide 1869 before being guided into and retained within the sharps receiver body 1823.

Figure 19:
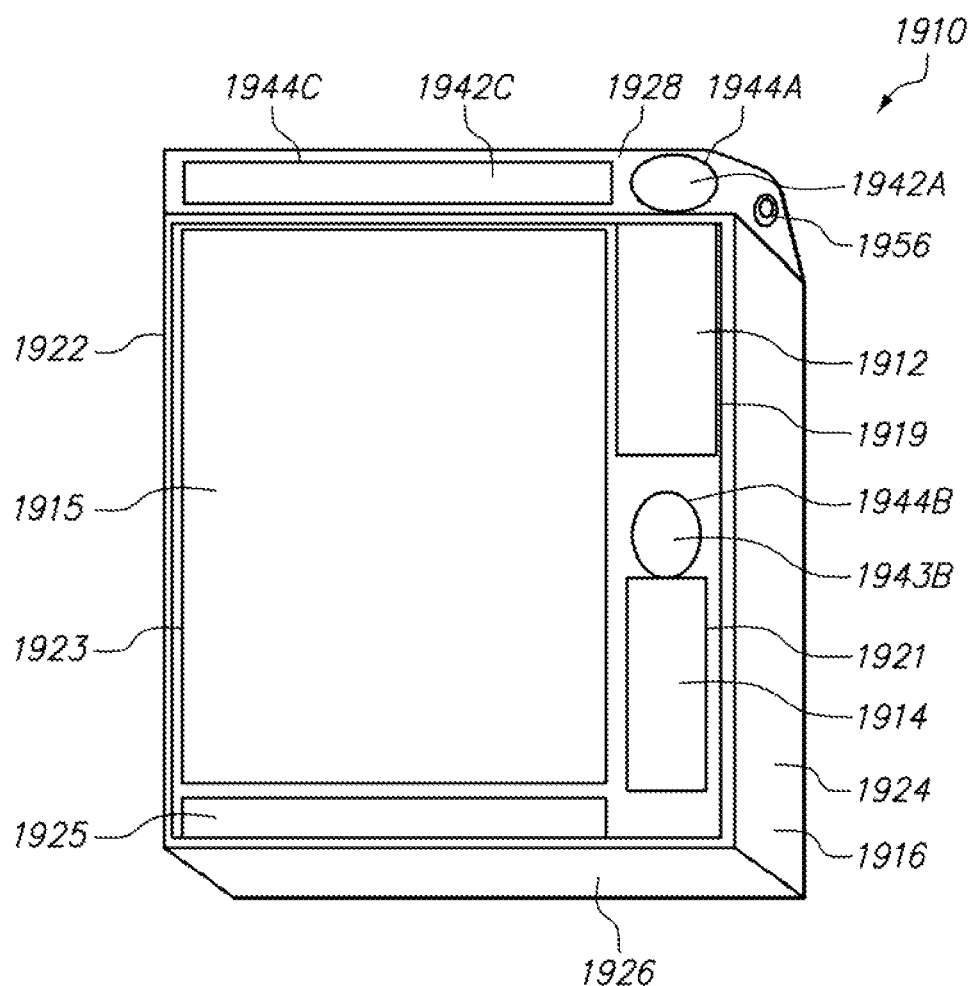
FIG. 19 is a front perspective view of yet another embodiment of a pharmaceutical waste disposal assembly having features of the present invention.

FIG. 19 is a front perspective view of yet another embodiment of a pharmaceutical waste disposal assembly 1910 having features of the present invention. Some of the features of the pharmaceutical waste disposal assembly 1910 are substantially similar to the pharmaceutical waste disposal assembly 1810 described above with regard to FIG. 18A. For example, in this embodiment, the pharmaceutical waste disposal assembly 1910 includes a receiver assembly 1951, which includes a fluid waste receiver 1912 (illustrated in phantom), a solid waste receiver 1914 (illustrated in phantom), a sharps receiver 1915 (illustrated in phantom), an absorption pad 1925 (illustrated in phantom), and a receiver retainer 1916. The receiver retainer 1916 is adapted to receive and selectively retain the fluid waste receiver 1912, the solid waste receiver 1914 and the sharps receiver 1915.

In this embodiment, the fluid waste receiver 1912 includes a fluid receiver body 1919 (illustrated in phantom), the solid waste receiver 1914 includes a solid receiver body 1921 (illustrated in phantom), and the sharps receiver 1915 includes a sharps receiver body 1923 (illustrated in phantom). As illustrated, the fluid receiver body 1919 and the solid receiver body 1921 can each be positioned adjacent to the sharps receiver body 1923 within the receiver retainer 1916. Additionally, in this embodiment, the solid receiver body 1921 is positioned substantially directly below the fluid receiver body 1919. Alternatively, the fluid receiver body 1919, the solid receiver body 1921 and the sharps receiver body 1923 can have a different orientation relative to one another within the retainer receiver 1916.

Further, in certain embodiments, one or more of the fluid waste receiver 1912, the solid waste receiver 1914 and the sharps receiver 1915 can be formed together as an integrated unit, as previously described herein. Stated another way, one or more of the fluid waste receiver 1912, the solid waste receiver 1914 and the sharps receiver 1915 can be formed as a unitary structure. In such embodiments, one or more of the fluid waste receiver 1912, the solid waste receiver 1914 and the sharps receiver 1915 can be inserted into and/or removed from the receiver retainer 1916 together as an integrated unit.

Although not necessarily illustrated in FIG. 19, the fluid waste receiver 1912, the solid waste receiver 1914, the sharps receiver 1915, the receiver retainer 1916 and the absorption pad 1925 can include some or all of the same components illustrated and described in any of the above embodiments, including in FIG. 18A, which function substantially as described previously herein. Accordingly, a detailed description of such features will not be repeated.

As illustrated in this embodiment, the receiver retainer 1916 can include a retainer housing 1922 including one or more retainer side walls 1924, a retainer base 1926 and a retainer lid 1928. In FIG. 19, a solid side aperture 1943B is positioned substantially within and extends through one of the retainer side walls 1924. The solid side aperture 1943B allows solid pharmaceutical waste to be deposited into the solid waste receiver 1914 from outside the receiver retainer 1916. Additionally, the retainer lid 1928 includes a fluid lid aperture 1942A and a sharps lid aperture 1942C that are positioned within and extend through the retainer lid 1928. The fluid lid aperture 1942A allows fluid pharmaceutical waste to be deposited into the fluid waste receiver 1912 from outside of the receiver retainer 1916. The sharps lid aperture 1942C allows sharps waste to be deposited into the sharps receiver 1915 from outside of the receiver retainer 1916. In certain non-exclusive alternative embodiments, the positioning of the apertures 1942A, 1943B, 1942C can be varied. For example, any of the apertures 1942A, 1943B, 1942C can be positioned within and extend through any of the side walls 1924, the retainer base 1926 or the retainer lid 1928 of the retainer housing 1922.

In the embodiment illustrated in FIG. 19, the fluid lid aperture 1942A includes a fluid waste guide 1944A, the solid side aperture 1943B includes a solid waste guide 1944B, and the sharps lid aperture 1942C includes a sharps waste guide 1944C. As illustrated, the fluid waste guide 1944A and the sharps waste guide 1944C can be positioned substantially within and extend through the retainer lid 1828, and the solid waste guide 1944B can be positioned substantially within and extend through one of the retainer side walls 1924. Each waste guide 1944A, 1944B, 1944C assists in directing the specific waste (liquid, solid or sharps) to the appropriate waste receiver 1912, 1914, 1915, in a manner substantially similar or identical to that previously described herein.

In the embodiment illustrated in FIG. 19, the receiver retainer 1916 also includes a locking mechanism 1956 for locking the retainer lid 1928 in a closed position, as illustrated in FIG. 19.

Figure 20:
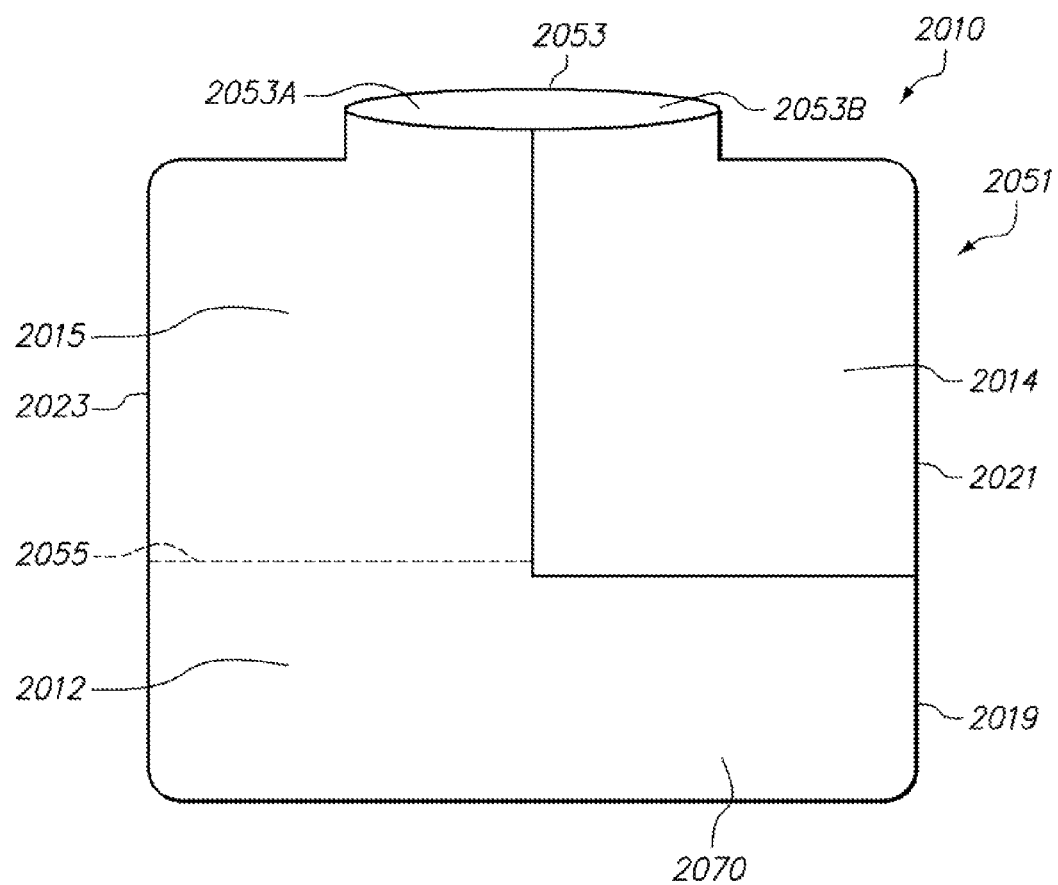
FIG. 20 is a front elevation of another embodiment of a portion of a pharmaceutical waste disposal assembly having features of the present invention.

FIG. 20 is a front elevation of an embodiment of a portion of a pharmaceutical waste disposal assembly 2010 having features of the present invention. In particular, FIG. 20 illustrates a receiver assembly 2051 that is usable as part of the pharmaceutical waste disposal assembly 2010. In one embodiment, the receiver assembly 2051 can be positioned and received within a receiver retainer, such as any of the receiver retainers illustrated and described herein. Alternatively, the receiver assembly 2051 can function as a stand-alone waste disposal unit without the need for a separate receiver retainer.

As illustrated, the receiver assembly 2051 includes a fluid waste receiver 2012, a solid waste receiver 2014 and a sharps receiver 2015. The fluid waste receiver 2012 includes a fluid receiver body 2019, the solid waste receiver 2014 includes a solid receiver body 2021, and the sharps receiver 2015 includes a sharps receiver body 2023. As illustrated, the fluid receiver body 2019 and the solid receiver body 2021 can each be positioned adjacent to the sharps receiver body 2023 within the receiver assembly 2051. Additionally, in this embodiment, the solid receiver body 2021 is positioned laterally adjacent to the sharps receiver body 2023, and the fluid receiver body 2019 is positioned substantially directly below the solid receiver body 2021 and the sharps receiver body 2023. Alternatively, the fluid receiver body 2019, the solid receiver body 2021 and the sharps receiver body 2023 can have a different orientation relative to one another within the receiver assembly 2051.

In this embodiment, the receiver assembly 2051 further includes a unit aperture 2053. The unit aperture 2053 allows fluid pharmaceutical waste, solid pharmaceutical waste and sharps waste to be deposited into the receiver assembly 2051 from outside of the receiver assembly 2051. As illustrated, the unit aperture 2053 is substantially circular shaped and is positioned substantially centrally located along the top of the receiver assembly 2051. In certain non-exclusive alternative embodiments, the unit aperture 2053 can have a different shape and/or be positioned along a different portion of the receiver assembly 2051. Still alternatively, the receiver assembly 2051 can include more than one unit aperture 2053.

In FIG. 20, the unit aperture 2053 includes a first side 2053A and a second side 2053B. As illustrated, the first side 2053A allows fluid pharmaceutical waste and sharps waste to be deposited into the receiver assembly 2051 from outside of the receiver assembly 2051. More particularly, the first side 2053A allows fluid pharmaceutical waste to be deposited into the fluid receiver body 2019, and allows sharps waste to be deposited into the sharps receiver body 2023. The second side 2053B allows solid pharmaceutical waste to be deposited into the receiver assembly 2051 from outside of the receiver assembly 2051. More particularly, the second side 2053B allows solid pharmaceutical waste to be deposited into the solid receiver body 2021.

As illustrated in FIG. 20, the receiver assembly 2051 can further include a receiver divider 2055. The receiver divider 2055 is positioned substantially between the fluid receiver body 2019 and the sharps receiver body 2023. The receiver divider 2055 can be made from a fluid-permeable material such that the fluid pharmaceutical waste can pass through the receiver divider 2055 into the fluid receiver body 2019. Additionally, the receiver divider 2055 inhibits sharps waste from passing through into the fluid receiver body 2019 and helps to retain the sharps waste within the sharps receiver body 2023.

Additionally, the receiver assembly 2051 includes a fluid absorber 2070 that is positioned substantially within the fluid receiver body 2019. The fluid absorber 2070 absorbs fluid waste that enters the fluid receiver body 2019. In one embodiment, the fluid absorber 2070 includes a solid material such as a super absorbent polymer (SAP), which can also be combined with additional fluff or fibrous materials, for example. Alternatively, the fluid absorber 2070 can include other suitable, relatively absorbent materials. The material that forms the fluid absorber 2070 can also include antibacterial, antimicrobial, and/or anti-odor characteristics. For example, in one embodiment, the fluid absorber 2070 can be impregnated with a silver or copper type of antibacterial and/or antimicrobial agent to reduce or eliminate the possibility of bacterial or fungal growth. Moreover, in one embodiment, the fluid absorber 2070 can convert the fluid waste to a gelatinous or solid material that is less likely to spill or leak from the fluid receiver body 2019.

Figure 21:
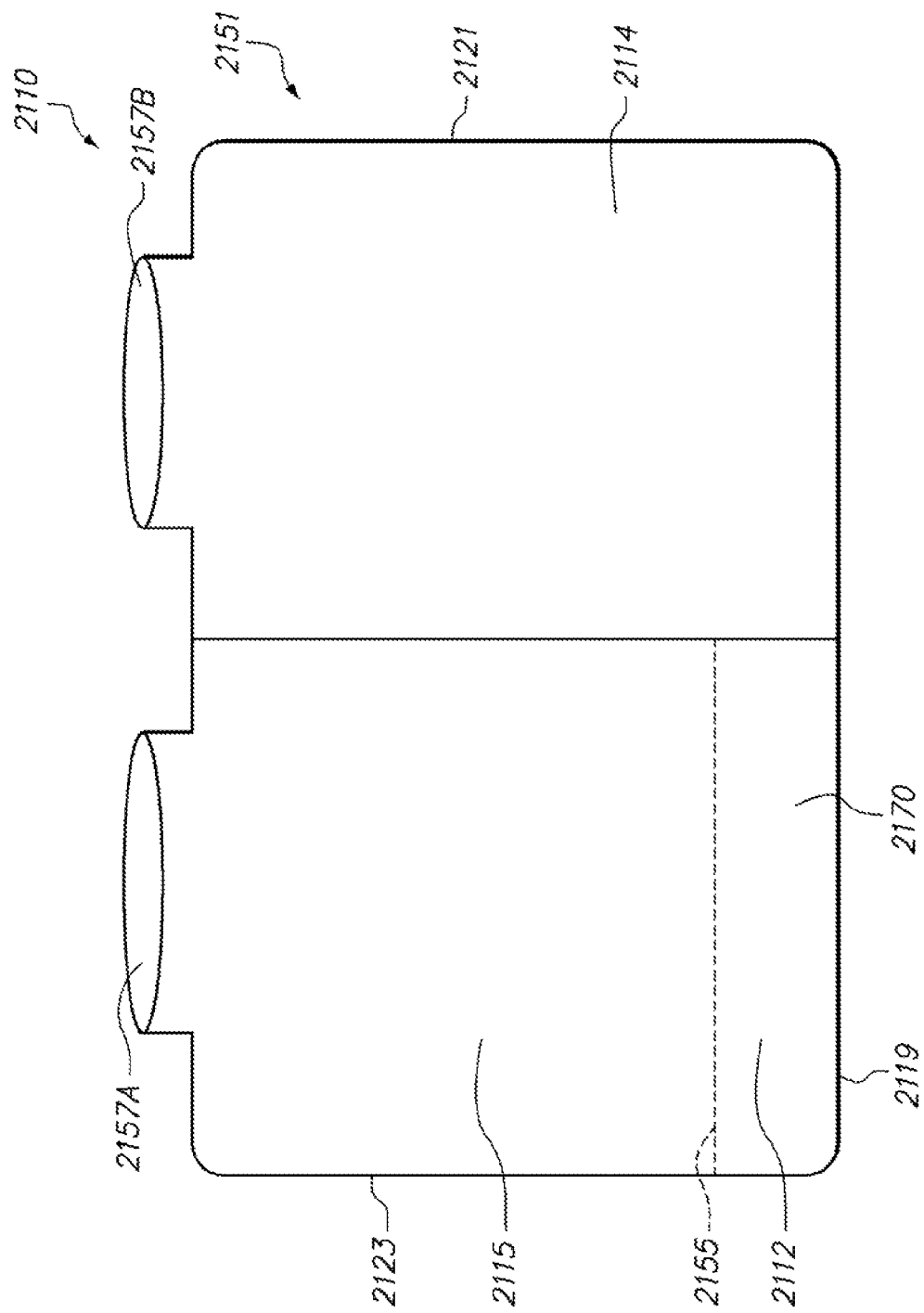
FIG. 21 is a front elevation of still another embodiment of a portion of a pharmaceutical waste disposal assembly having features of the present invention.

FIG. 21 is a front elevation of another embodiment of a portion of a pharmaceutical waste disposal assembly 2110 having features of the present invention. In particular, FIG. 21 illustrates a receiver assembly 2151 that is usable as part of the pharmaceutical waste disposal assembly 2110. In one embodiment, the receiver assembly 2151 can be positioned and received within a receiver retainer, such as any of the receiver retainers illustrated and described herein. Alternatively, the receiver assembly 2151 can function as a stand-alone waste disposal unit without the need for a separate receiver retainer.

As illustrated, the receiver assembly 2151 includes a fluid waste receiver 2112, a solid waste receiver 2114 and a sharps receiver 2115. The fluid waste receiver 2112 includes a fluid receiver body 2119, the solid waste receiver 2114 includes a solid receiver body 2121, and the sharps receiver 2115 includes a sharps receiver body 2123. As illustrated, the fluid receiver body 2119 and the solid receiver body 2121 can each be positioned adjacent to the sharps receiver body 2123 within the receiver assembly 2151. Additionally, in this embodiment, the fluid receiver body 2119 is positioned substantially directly below the solid receiver body 2121, and the solid receiver body 2121 is positioned laterally adjacent to the sharps receiver body 2123 and the fluid receiver body 2119. Alternatively, the fluid receiver body 2119, the solid receiver body 2121 and the sharps receiver body 2123 can have a different orientation relative to one another within the receiver assembly 2151.

In this embodiment, the receiver assembly 2151 further includes a first unit aperture 2157A and a second unit aperture 2157B. Alternatively, the receiver assembly 2151 can include greater or fewer than two unit apertures.

The first unit aperture 2157A allows fluid pharmaceutical waste and sharps waste to be deposited into the receiver assembly 2151 from outside of the receiver assembly 2151. More particularly, the first unit aperture 2157A allows fluid pharmaceutical waste to be deposited into the fluid receiver body 2119, and allows sharps waste to be deposited into the sharps receiver body 2123. As illustrated, the first unit aperture 2157A is substantially circular shaped and is positioned nearer to one side along the top of the receiver assembly 2151. In certain non-exclusive alternative embodiments, the first unit aperture 2157A can have a different shape and/or be positioned along a different portion of the receiver assembly 2151.

The second unit aperture 2157B allows solid pharmaceutical waste to be deposited into the receiver assembly 2151 from outside of the receiver assembly 2151. More particularly, the second unit aperture 2157B allows solid pharmaceutical waste to be deposited into the solid receiver body 2121. As illustrated, the second unit aperture 2157B is substantially circular shaped and is positioned nearer to the other side from the first unit aperture 2157A along the top of the receiver assembly 2151. In certain non-exclusive alternative embodiments, the second unit aperture 2157B can have a different shape and/or be positioned along a different portion of the receiver assembly 2151.

As illustrated in FIG. 21, the receiver assembly 2151 can further include a receiver divider 2155. The receiver divider 2155 is positioned substantially between the fluid receiver body 2119 and the sharps receiver body 2123. The receiver divider 2155 can be made from a fluid-permeable material such that the fluid pharmaceutical waste can pass through the receiver divider 2155 into the fluid receiver body 2119. Additionally, the receiver divider 2155 inhibits sharps waste from passing through into the fluid receiver body 2119 and helps to retain the sharps waste within the sharps receiver body 2123.

Additionally, the receiver assembly 2151 includes a fluid absorber 2170 that is positioned substantially within the fluid receiver body 2119. The fluid absorber 2170 absorbs fluid waste that enters the fluid receiver body 2119. In one embodiment, the fluid absorber 2170 includes a solid material such as a super absorbent polymer (SAP), which can also be combined with additional fluff or fibrous materials, for example. Alternatively, the fluid absorber 2170 can include other suitable, relatively absorbent materials. The material that forms the fluid absorber 2170 can also include antibacterial, antimicrobial, and/or anti-odor characteristics. For example, in one embodiment, the fluid absorber 2170 can be impregnated with a silver or copper type of antibacterial and/or antimicrobial agent to reduce or eliminate the possibility of bacterial or fungal growth. Moreover, in one embodiment, the fluid absorber 2170 can convert the fluid waste to a gelatinous or solid material that is less likely to spill or leak from the fluid receiver body 2119.

Figure 22A:
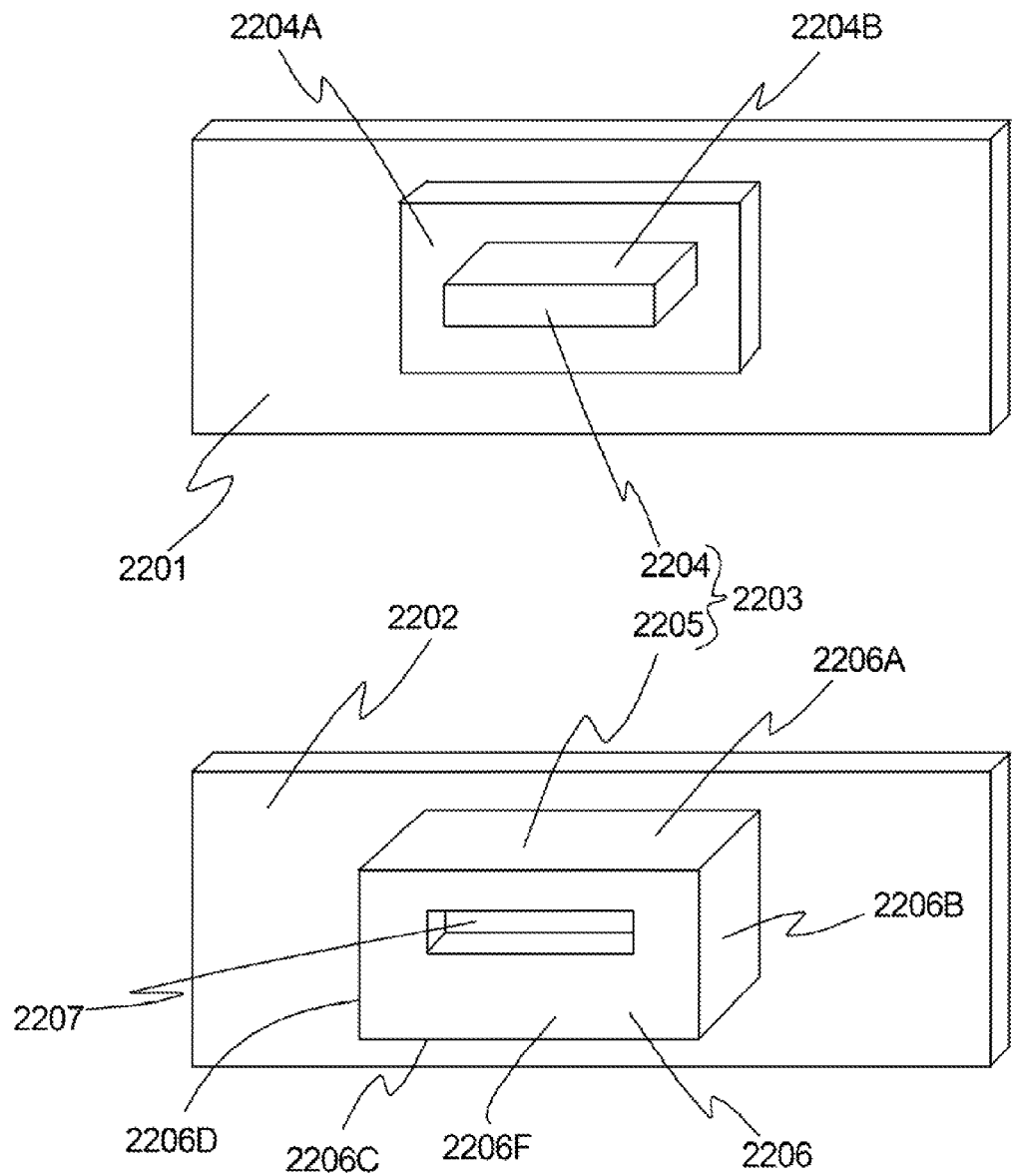
FIG. 22A is a perspective view of a first surface, a second surface, and an embodiment of a cancellation feature usable as part of the present invention.

FIG. 22A is a perspective view of a first surface 2201, a second surface 2202, and an embodiment of a cancellation feature 2203 that is usable between the first surface 2201 and the second surface 2202 as part of the present invention. More particularly, FIG. 22A illustrates that the cancellation feature 2203 includes a first cancellation member 2204 that is secured to the first surface 2201 and a second cancellation member 2205 that is secured to the second surface 2202. Alternatively, the first cancellation member 2204 can be integrally formed with the first surface 2201 and/or the second cancellation member 2205 can be integrally formed with the second surface 2202. As illustrated in FIG. 22A, the second cancellation member 2205 of the cancellation feature 2203 is shown in a pre-engaged configuration.

It should be noted that the use of the terms "first cancellation member", and "second cancellation member" is merely for ease of discussion and is not intended to be limiting in any manner, and either cancellation member can be equally referred to as the first cancellation member and/or the second cancellation member.

In some embodiments, the first surface 2201 forms a portion of a receiver or receiver assembly, e.g., one of the receivers or receiver assemblies previously illustrated and described herein, and the second surface 2202 forms a portion of a receiver retainer, e.g., one of the receiver retainers previously illustrated and described herein. For example, in one such embodiment, the first surface 2201 can form an outer surface of a bottom of a receiver body of the receiver or receiver assembly (e.g. the first surface 2201 can form an outer surface of the receiver bottom 283 of the fluid receiver 212C illustrated in FIG. 4C) and the second surface 2202 can form an inner surface of a retainer base of the receiver retainer (e.g. the first surface 2202 can form an inner surface of the retainer base 26 of the receiver retainer 16 illustrated in FIG. 1A). Alternatively, the first surface 2201 can form a different portion of the receiver or receiver assembly and/or the second surface 2202 can form a different portion of the receiver retainer. Still alternatively, the first surface 2201 can form a portion of the receiver retainer e.g., the first surface 2201 can form an inner surface of the retainer base 26 of the receiver retainer 16 illustrated in FIG. 1A) and the second surface 2202 can form a portion of the receiver or receiver assembly (e.g., the second surface 2202 can form an outer surface of the receiver bottom 283 of the fluid receiver 212C illustrated in FIG. 4C). Yet alternatively, in embodiments that do not utilize a receiver retainer, one of the surfaces 2201, 2202 can be any surface upon which the receiver or receiver assembly is mounted.

Figure 22C:
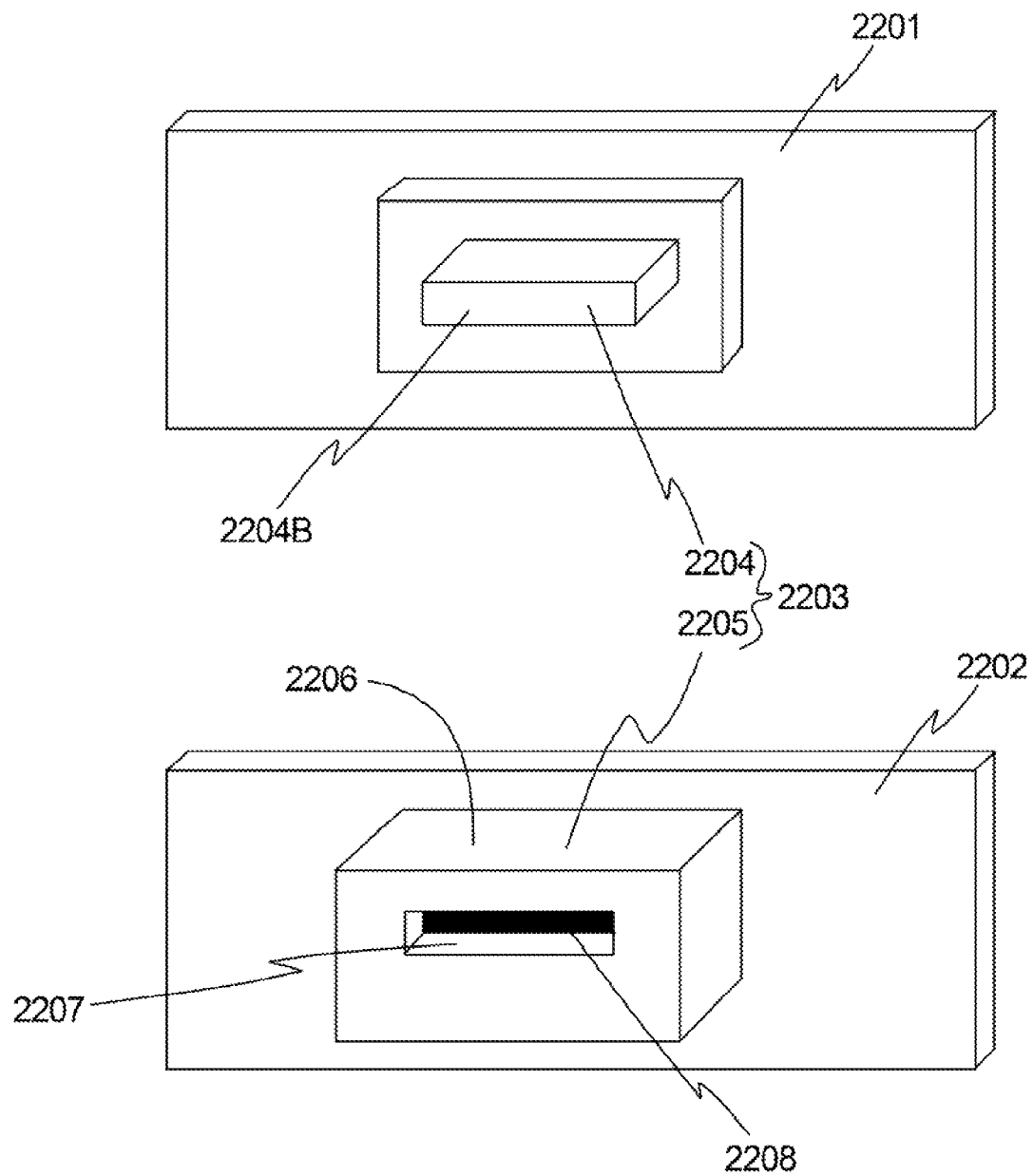
FIG. 22C is a another perspective view of the first surface, the second surface and the cancellation feature illustrated in FIG. 22A.

The cancellation feature 2203 as illustrated and described in detail herein inhibits the reuse of the receiver or receiver assembly, e.g., within the receiver retainer. More specifically, through use, the second cancellation member 2205 moves from a pre-engaged configuration (as illustrated in FIG. 22A) to a post-engaged configuration (as illustrated in FIG. 22C) that is different from the pre-engaged configuration. Stated in another fashion, the second cancellation member 2205 moves from the pre-engaged configuration to an engaged configuration (as illustrated in FIG. 22B) that is different from the pre-engaged configuration, and subsequently to the post-engaged configuration that is different than the pre-engaged configuration and the engaged configuration. As described in detail herein, the second cancellation member 2205 moves from the ere-engaged configuration to the engaged configuration due to the selective engagement between the first cancellation member 2204 and the second cancellation member 2205. Moreover, the second cancellation member 2205 automatically moves from the engaged configuration to the post-engaged configuration after the second cancellation member and the first cancellation member have been selectively disengaged from one another.

When in the pre-engaged configuration, the second cancellation member 2205 is configured to engage the first cancellation member 2204. Accordingly, in such configuration, the receiver or receiver assembly can be effectively seated and used within the receiver retainer. Conversely, when in the post-engaged configuration, the second cancellation member 2205 is inhibited from engaging the first cancellation member 2204. Accordingly, in such configuration, the receiver or receiver assembly is inhibited from being effectively seated and used within the receiver retainer.

Additionally, it should be noted that although the cancellation feature 2203 is described herein as being useful as part of the pharmaceutical waste disposal assembly, such description is not intended to be limiting in any fashion, and the cancellation feature can be usable in other disciplines or industries. For example, the cancellation feature 2203 can be used with a medical waste disposal assembly, an industrial waste disposal assembly, or another suitable assembly, where there is a desire to limit reuse of one or more of the assembly elements.

The design of the first cancellation member 2204 can be varied to suit the specific design requirements of the cancellation feature 2203 and/or the pharmaceutical waste disposal assembly. As illustrated in this embodiment, the first cancellation member 2204 can include a first member base 2204A and a first member node 2204B.

As illustrated in FIG. 22A, the first member base 2204A is secured to and/or is integrally formed with the first surface 2201. Additionally, the first member base 2204A has a substantially flat, planar, rectangular shape that can be substantially centrally positioned along the first surface 2201. Alternatively, the first member base 2204A can have another suitable shape and/or orientation, and/or the first member base 2204A can be positioned along a different portion of the first surface 2201.

Additionally, as illustrated in FIG. 22A, the first member node 2204B is secured to and/or is integrally formed with the first member base 2204A, and the first member node 2204B can cantilever away from the first member base 2204A and/or away from the first surface 2201. Alternatively, in one embodiment, the first cancellation member 2204 can omit the first member base 2204A. In such embodiment, the first member node 2204B can be secured to and/or be integrally formed with the first surface 2201 and the first member node 2204B can cantilever away from the first surface 2201.

Further, in this embodiment, the first member node 2204B has a generally rectangular-shape cross-section that is received by a portion of the second cancellation member 2205. Alternatively, the first member node 2204B can have a different shape.

Still further, the first cancellation member 2204 can be formed from any suitably durable materials. In one embodiment, the first cancellation member 2204 can be formed from a durable injection-molded plastic material. Alternatively, the first cancellation member 2204 can be formed from fiberglass, glass, ceramic, various metals, a composite material, or a combination thereof, as non-exclusive examples.

The design of the second cancellation member 2205 can be varied to suit the specific design requirements of the cancellation feature 2203. As illustrated in FIG. 22A, the second cancellation member 2205 can include a second member body 2206 having a second member aperture 2207.

Further, as illustrated in FIG. 22A, the second member body 2206 is secured to and/or is integrally formed with the second surface 2202. Additionally, in this embodiment, the second member body 2206 has a generally rectangular shape and includes a front 2206F and a plurality of sides, e.g., a first side 2206A, a second side 2206B, a third side 2206C and a fourth side 2206D, although the second member body 2206 can have greater than or fewer than four sides. Moreover, as shown, the second member body 2206 can be substantially centrally positioned along the second surface 2202. Alternatively, the second member body 2206 can have another suitable shape and/or orientation, and/or the second member body 2206 can be positioned along a different portion of the second surface 2202.

It should be noted that the use of the terms "first side", "second side", "third side" and "fourth side" is merely for ease of discussion and is not intended to be limiting in any manner, and any sides can be equally referred to as the first side, the second side, the third side and/or the fourth side.

The second member aperture 2207 extends through the front 2206F of the second member body 2206. When the second cancellation member 2205 is in the pre-engaged configuration, the second member aperture 2207 is adapted to receive a portion of the first cancellation member 2204. In particular, as shown, the second member aperture 2207 can be generally rectangular-shaped to effectively receive the first member node 2204B of the first cancellation member 2204. Moreover, when the second cancellation member 2205 is in the pre-engaged configuration, the first member node 2204B can extend partially or fully through the second member aperture 2207 and can extend into a body recess 2309 (illustrated in FIG. 23B) that is formed in the second member body 2206. Accordingly, in this configuration, the second cancellation member 2205 can selectively engage the first cancellation member 2204, and, thus, the receiver can be effectively seated and used within the receiver retainer. In alternative embodiments, the second member aperture 2207 can have another suitable shape.

Additionally, the second cancellation member 2205 can be formed from any suitably durable materials. In one embodiment, the second cancellation member 2205 can be formed from a durable injection-molded plastic material. Alternatively, the second cancellation member 2205 can be formed from fiberglass, glass, ceramic, various metals, a composite material, or a combination thereof, as non-exclusive examples.

FIG. 22B is a side view of the first surface 2201, the second surface 2202 and the cancellation feature 2203 illustrated in FIG. 22A. Further, as illustrated in FIG. 22B, the second cancellation member 2205 of the cancellation feature 2203 is in an engaged configuration. Stated another way, as shown in FIG. 22B, the second cancellation member 2205 is engaged with the first cancellation member 2204 with the first member node 2204B (illustrated in phantom) extending partially or fully through the second member aperture 2207 (illustrated in FIG. 22A) and extending into the body recess 2309 (illustrated in FIG. 23B) that is formed by the second member body 2206. Additionally, in one embodiment, in the engaged configuration the first member base 2204A contacts the second member body 2206.

As utilized herein, the term "engaged", "engaging" or "engagement" is defined as enabling the first member node 2204B to extend through the second member aperture 2207 and into the body recess 2309 such that the first surface 2201 is stably and sturdily positioned substantially adjacent to the second surface 2202. In such a configuration, the receiver or receiver assembly can be effectively and stably seated and used within the receiver retainer. Accordingly, if the second cancellation member 2205 is inhibited from engaging the first cancellation member 2204, the first member node 2204B cannot extend through the second member aperture 2207 and into the body recess 2309, and the first surface 2201 cannot be stably and sturdily positioned substantially adjacent to the second surface 2202.

FIG. 22C is another perspective view of the first surface 2201, the second surface 2202 and the cancellation feature 2203 illustrated in FIG. 22A. As illustrated in FIG. 22C, the second cancellation member 2205 of the cancellation feature 2203 is in a post-engaged configuration.

As shown in FIG. 22C, the second cancellation member 2205 includes a valve 2208. In one embodiment, when the second cancellation member 2205 is in the post-engaged configuration, the valve 2208 is positioned to inhibit the first member node 2204B from extending fully through the second member aperture 2207. Moreover, when the second cancellation member 2205 is in the post-engaged configuration, the valve 2208 inhibits the first member node 2204B from extending into the body recess 2309 (illustrated in FIG. 23B) that is formed in the second member body 2206. Accordingly, in this configuration, the second cancellation member 2205 is inhibited such that it can no longer effectively engage the first cancellation member 2204. Thus, the receiver or receiver assembly is inhibited from being effectively seated and used within the receiver retainer and the user is inhibited from reusing the receiver or receiver assembly within the receiver retainer because the retainer can wobble or otherwise be unstable relative to the receiver retainer. In one embodiment, the valve 2208 can be relatively dark in color, e.g., black, such that it is easily visible to the user when the second cancellation member 2205 is in the post-engaged configuration. With this design, the user can easily identify that the receiver or receiver assembly has previously been used and should not be reused. Alternatively, the valve 2208 can have another suitable distinguishing color or indicia.

FIG. 23A is a front elevation view of the second cancellation member 2205 illustrated in FIG. 22A, with the second cancellation member 2205 in the pre-engaged configuration. More specifically, FIG. 23A illustrates the second member body 2206 and the second member aperture 2207 of the second cancellation member 2205, with the second member aperture 2207 extending through the front 2206F of the second member body 2206. In this embodiment, in the pre-engaged configuration, the second member aperture 2207 can effectively receive the first member node 2204B (illustrated in FIG. 22A) of the first cancellation member 2204 (illustrated in FIG. 22A). Accordingly, the second cancellation member 2205 can engage the first cancellation member 2204 so that the receiver or receiver assembly can be effectively seated and used within the receiver retainer.

FIG. 23B is a rear elevation view of the second cancellation member 2205 illustrated in FIG. 22A, with the second cancellation member 2205 in the pre-engaged configuration. In the embodiment illustrated in FIG. 23B, the second member body 2206 includes the first side 2206A, the second side 2206B, the third side 2206C and the fourth side 2206D that cooperate with the front 2206F (illustrated in FIG. 23A) to form the body recess 2309 or cavity. FIG. 23B illustrates that the second cancellation member 2205 can further include a blocker 2311, the valve 2208, and a resilient member 2313.

In this embodiment, the body recess 2309 is generally rectangular-shaped and is somewhat smaller than the outer dimensions of the second member body 2206. Alternatively, the body recess 2309 can have another suitable shape. In the embodiment illustrated in FIG. 23B, the body recess 2309 is sized and shaped so that the blocker 2311, the valve 2208 and the resilient member 2313 are positioned substantially within the body recess 2309. Moreover, as shown in FIG. 23B, the second member body 2206 can basically have a substantially rectangular shaped shell that can be partially or fully open along the back edge. Alternatively, the second member body 2206 can further include a back side such that the blocker 2311, the valve 2208 and/or the resilient member 2313 can be positioned substantially within the second member body 2206.

In one embodiment, the blocker 2311 can be a substantially rectangular shaped block that is positioned within the body recess 2309 adjacent to the first side 2206A, the second side 2206B and the fourth side 2206D of the second member body 2206. When the second cancellation member 2205 is in the pre-engaged configuration, the blocker 2311 can be positioned substantially between the valve 2208 and the first side 2206A of the second member body 2206. Thus blocker 2311 can block the valve 2208 from moving toward the first side 2206A of the second body member 2206, where the valve 2208 would otherwise function to inhibit access to the body recess 2309 by the first member node 2204B (illustrated in FIG. 22A). In certain alternative embodiments, the blocker 2311 can have another suitable shape, and/or the blocker 2311 can have a different relative positioning within the body recess 2309 from that illustrated in FIG. 23B.

In one embodiment, the valve 2208 is a substantially rectangular shaped block that is secured to the resilient member 2313 and positioned within the body recess 2309 substantially between the blocker 2311 and the resilient member 2313. The valve 2208 can extend substantially fully between the second side 2206B and the fourth side 2206D of the second member body 2206. In certain alternative embodiments, the valve 2208 can have another suitable shape and/or the valve 2208 can have a different relative positioning within the body recess 2309.

In the embodiment illustrated in FIG. 23B, the resilient member 2313 can be secured to and can extend between the valve 2208 and the third side 2206C of the second member body 2206. Further, when the second cancellation member 2205 is in the pre-engaged configuration, the resilient member 2313 can be compressed to maintain the valve 2208 in contact with the blocker 2311.

FIG. 23C is a cross-sectional view of the second cancellation member 2205 taken on line 23C-23C in FIG. 23A. In particular, in the embodiment illustrated in FIG. 23C, when the second cancellation member 2205 is in the pre-engaged configuration, the blocker 2311 is positioned adjacent to the front 2206F of the second member body 2206 and the second member aperture 2207.

In one embodiment, the blocker 2311 can move away from the front 2206F and the second member aperture 2207 via contact between the blocker 2311 and the first member node 2204B. Accordingly, engagement between the first cancellation member 2204 (illustrated in FIG. 22A) and the second cancellation member 2205, i.e. extending of the first member node 2204B through the second member aperture 2207 and into the body recess 2309, initiates contact between the first member node 2204B and the blocker 2311. This contact results in movement of the blocker 2311 away from the front 2206F and the second member aperture 2207. In FIG. 23C, movement of the blocker 2311 is illustrated by arrow 2311A. Following this movement, of the blocker 2311, the blocker 2311 is no longer positioned to block the valve 2208 from moving toward the first side 2206A of the second body member 2206. Further, when the blocker 2311 no longer blocks movement of the valve 2208, the resilient member 2313 pushes the valve 2208 in the direction of arrow 2208A, i.e. away from the third side 2206C and toward the first side 2206A of the second member body 2206, as illustrated in FIG. 23C. Moreover, when the blocker 2311 has been moved away from the front 2206F and the second member aperture 2207 (as shown by arrow 2311A) such that the blocker 2311 is no longer blocking the valve 2208 from being toward the first side 2206A of the second member body 2206, and when the resilient member 2313 initially pushes the valve 2208 away from the third side 2206C and toward the first side 2206A of the second member body 2206 (as shown by arrow 2208A), the second cancellation member 2205 is now in the engaged configuration.

In one embodiment, when the first cancellation member 2204 is engaged with the second cancellation member 2205 so that the first member node 2204B extends through the second member aperture 2207 and into the body recess 2309, i.e. when the second cancellation member is in the engaged configuration, the resilient member 2313 pushes the valve 2208 a small distance so that the valve 2208 is in contact with the first member node 2204B. Moreover, this small movement of the valve 2208 inhibits the blocker 2311 from returning toward the front 2206F of the second member body 2206 when the first member node 2204B is removed from the second member aperture 2207. Thus, when the first member node 2204B is removed from the body recess 2309 and/or from the second member aperture 2207, i.e. when the first cancellation member 2204 and the second cancellation member 2205 are disengaged from one another, the resilient member 2313 pushes the valve 2208 more fully toward the first side 2206A of the second member body 2206 so that the valve 2208 is positioned adjacent to the second member aperture 2207. Stated in another fashion when the first cancellation member 2204 and the second cancellation member 2205 are disengaged from one another, the second cancellation member automatically moves from the engaged configuration to the post-engaged configuration.

FIG. 24A is a front elevation view of the second cancellation member 2205 illustrated in FIG. 22A, with the second cancellation member 2205 in the post-engaged configuration. More specifically, FIG. 24A illustrates the second member body 2206 and the second member aperture 2207 of the second cancellation member 2205. In the post-engaged configuration, the valve 2208 is positioned to inhibit the first member node 2204B (illustrated in FIG. 22A) from extending through the second member aperture 2207 and extending into the body recess 2309 (illustrated in FIG. 24B). In this configuration, the second cancellation member 2205 is inhibited from engaging the first cancellation member 2204. Thus, the receiver or receiver assembly is inhibited from being effectively seated and used within the receiver retainer.

FIG. 24B is a rear elevation view of the second cancellation member 2205 illustrated in FIG. 22A, with the second cancellation member 2205 in the post-engaged configuration. As illustrated in FIG. 24B, when the second cancellation member 2205 is in the post-engaged configuration, the blocker 2311 has been moved so that the blocker 2311 is no longer positioned between the valve 2208 and the first side 2206A of the second member body 2206. Thus, the resilient member 2313 moves the valve 2208 toward the first side 2206A of the second member body 2206 as illustrated in FIG. 24C.

FIG. 24C is a cross-sectional view of the second cancellation member 2205 taken on line C-C in FIG. 24A. In particular, as illustrated in FIG. 24C, when the second cancellation member 2205 is in the post-engaged configuration, the blocker 2311 has been moved along the first side 2206A of the second member body 2206 and the valve 2208 has been moved along the front 2206F of the second member body 2206 so that the valve 2208 is positioned adjacent to the second member aperture 2207.

With the valve 2208 positioned adjacent to the second member aperture 2207, and the valve 2208 effectively held in that position due to the pressure exerted on the valve 2208 by the resilient member 2313, the first member node 2204B is inhibited from extending fully through the second member aperture 2207 and extending into the body recess 2309. Accordingly, as noted above, the second cancellation member 2205 is inhibited from engaging the first cancellation member 2204 (illustrated in FIG. 22A). Thus, the receiver or receiver assembly is inhibited from being effectively seated and used within the receiver retainer.

It is understood that although a number of different embodiments of the pharmaceutical waste disposal assembly 10 have been illustrated and described herein, one or more features of any one embodiment can be combined with one or more features of one or more of the other embodiment, provided that such combination satisfies the intent of the present invention.

While a number of exemplary aspects and embodiments of a pharmaceutical waste disposal assembly 10 have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A cancellation feature for a pharmaceutical waste disposal assembly, the pharmaceutical waste disposal assembly having a first surface and a second surface, the cancellation feature comprising:

a first cancellation member that is secured to the first surface, the first cancellation member including a first member node that cantilevers away from the first surface; and a second cancellation member that is secured to the second surface, the second cancellation member automatically moving from (i) an engaged configuration wherein the second cancellation member is engaged with the first cancellation member to (ii) a post-engaged configuration that inhibits engagement with the first cancellation member, the automatic movement occurring when the second cancellation member and the first cancellation member are disengaged from one another, the second cancellation member including a second member body having a second member aperture that receives the first member node, the second member body forming a body recess, and wherein when the second cancellation member is in the engaged configuration, the first member node extends fully through the second member aperture and into the body recess, wherein the second cancellation member is inhibited from being moved from the post-engaged configuration to the engaged configuration, and wherein when the second cancellation member is in the post-engaged configuration, the first member node is inhibited from extending fully through the second member aperture and into the body recess.

2. The cancellation feature of claim 1, wherein the second cancellation member further includes a blocker and a valve, wherein when the second cancellation member is in a pre-engaged configuration the blocker is positioned adjacent to the second member aperture, and wherein when the second cancellation member is in the post-engaged configuration the valve is positioned adjacent to the second member aperture.

3. A cancellation feature for a pharmaceutical waste disposal assembly, the pharmaceutical waste disposal assembly having a first surface and a second surface, the cancellation feature comprising:
 a first cancellation member that is secured to the first surface, the first cancellation member including a first member node that cantilevers away from the first surface; and
 a second cancellation member that is secured to the second surface, the second cancellation member including (a) a second member body, (b) a blocker, (c) a valve, and (d) a resilient member, the second member body having a second member aperture that receives the first member node, the second member body forming a body recess wherein the blocker, the valve and the resilient member are positioned substantially within the body recess; the second cancellation member automatically moving from (i) a pre-engaged configuration that allows engagement with the first cancellation member to (ii) a post-engaged configuration that inhibits engagement with the first cancellation member due to engagement and subsequent disengagement between the second cancellation member and the first cancellation member, wherein the second cancellation member is inhibited from being moved from the post-engaged configuration to the pre-engaged configuration, wherein when the second cancellation member is in the pre-engaged configuration the blocker is positioned adjacent to the second member aperture and the first member node can extend fully through the second member aperture and into the body recess, and wherein when the first member node extends fully through the second member aperture and into the body recess, the first member node contacts the blocker and moves the blocker away from the second member aperture and the resilient member moves the valve so that when the second cancellation member is in the post-engaged configuration the valve is positioned adjacent to the second member aperture; and
 wherein one of the first surface and the second surface forms a portion of a receiver that receives pharmaceutical waste, and wherein the other of the first surface and the second surface forms a portion of a receiver retainer that retains the receiver.

4. The cancellation feature of claim 3 wherein when the second cancellation member is in the pre-engaged configuration, the first member node can extend fully through the second member aperture and into the body recess; and wherein when the second cancellation member is in the post-engaged configuration, the first member node is inhibited from extending fully through the second member aperture and into the body recess.

5. A pharmaceutical waste disposal assembly comprising a receiver that receives pharmaceutical waste, a receiver retainer that retains the receiver, and the cancellation feature of claim 3.

6. A cancellation feature for a pharmaceutical waste disposal assembly, the pharmaceutical waste disposal assembly having a first surface and a second surface, the cancellation feature comprising:
 a first cancellation member that is secured to the first surface, the first cancellation member including a first member node that cantilevers away from the first surface; and
 a second cancellation member that is secured to the second surface, the second cancellation member automatically moving from (i) an engaged configuration wherein the second cancellation member is engaged with the first cancellation member to (ii) a post-engaged configuration that inhibits engagement with the first cancellation member, the automatic movement occurring when the second cancellation member and the first cancellation member are disengaged from one another, the second cancellation member including (a) a blocker, (b) a valve, and (c) a second member body having a second member aperture that receives the first member node, the second member body forming a body recess, wherein when the second cancellation member is in a pre-engaged configuration the blocker is positioned adjacent to the second member aperture, and when the second cancellation member is in the post-engaged configuration the valve is positioned adjacent to the second member aperture, and wherein the second cancellation member is inhibited from being moved from the post-engaged configuration to the engaged configuration.

7. The cancellation feature of claim 6 wherein when the second cancellation member is in the pre-engaged configuration, the first member node can extend fully through the second member aperture and into the body recess, and wherein when the first member node extends fully through the second member aperture and into the body recess, the first member node contacts the blocker and moves the blocker away from the second member aperture.

8. The cancellation feature of claim 7 wherein the second cancellation member further includes a resilient member that moves the valve to be positioned adjacent to the second member aperture subsequent to the first member node moving the blocker away from the second member aperture.

9. The cancellation feature of claim 6 wherein the first surface forms a portion of a receiver that receives pharmaceutical waste.

10. The cancellation feature of claim 9 wherein the second surface forms a portion of a receiver retainer that retains the receiver.

11. The cancellation feature of claim 6 wherein the second surface forms a portion of a receiver that receives pharmaceutical waste.

12. The cancellation feature of claim 11 wherein the first surface forms a portion of a receiver retainer that retains the receiver.

13. The cancellation feature of claim 6 wherein the first cancellation member further includes a first member base that is secured to the first surface, and wherein the first member node cantilevers away from the first member base.

14. The cancellation feature of claim 13 wherein the first member node is secured to the first member base.

15. The cancellation feature of claim 13 wherein the first member node is integrally formed with the first member base.

16. The cancellation feature of claim 6 wherein the second member body includes a front that is positioned spaced apart from the second surface, and wherein the second member aperture extends through the front of the second member body.

17. The cancellation feature of claim 8 wherein the blocker, the valve and the resilient member are positioned substantially within the body recess.

18. The cancellation feature of claim 6 wherein when the second cancellation member is in the engaged configuration, the first member node extends fully through the second member aperture and into the body recess.

19. The cancellation feature of claim 18 wherein when the second cancellation member is in the post-engaged configuration, the first member node is inhibited from extending fully through the second member aperture and into the body recess.

20. A pharmaceutical waste disposal assembly comprising a receiver that receives pharmaceutical waste, a receiver retainer that retains the receiver, and the cancellation feature of claim 6.

* * * * *